United States Patent
Shahabi et al.

(10) Patent No.: US 9,017,660 B2
(45) Date of Patent: Apr. 28, 2015

(54) COMPOSITIONS AND METHODS FOR PREVENTION OF ESCAPE MUTATION IN THE TREATMENT OF HER2/NEU OVER-EXPRESSING TUMORS

(75) Inventors: Vafa Shahabi, Valley Forge, PA (US); Anu Wallecha, Yardley, PA (US); Paulo C. Maciag, Long Grove, IL (US); Yvonne Paterson, Philadelphia, PA (US); Nicola Mason, Philadelphia, PA (US); Matthew Seavey, Secane, PA (US)

(73) Assignees: Advaxis, Inc., Princeton, NJ (US); The Trustees of the University of Pennsylvania, Philadelphia, PA (US)

( * ) Notice: Subject to any disclaimer, the term of this patent is extended or adjusted under 35 U.S.C. 154(b) by 63 days.

(21) Appl. No.: 13/210,696

(22) Filed: Aug. 16, 2011

(65) Prior Publication Data

US 2012/0014984 A1  Jan. 19, 2012

Related U.S. Application Data

(63) Continuation-in-part of application No. 12/945,386, filed on Nov. 12, 2010.

(60) Provisional application No. 61/260,277, filed on Nov. 11, 2009.

(51) Int. Cl.
| | |
|---|---|
| *A61K 35/74* | (2006.01) |
| *A61K 39/00* | (2006.01) |
| *C12N 1/21* | (2006.01) |
| *C07K 19/00* | (2006.01) |

(52) U.S. Cl.
CPC ....... *A61K 39/0011* (2013.01); *A61K 2039/522* (2013.01); *A61K 2039/523* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 5,922,583 A | 7/1999 | Morsey et al. | |
| 6,099,848 A | 8/2000 | Frankel et al. | |
| 6,773,900 B2 | 8/2004 | Short et al. | |
| 6,855,320 B2 | 2/2005 | Paterson et al. | |
| 7,375,091 B2 * | 5/2008 | Cheever et al. | 514/44 R |
| 7,794,729 B2 | 9/2010 | Paterson et al. | |
| 7,820,180 B2 | 10/2010 | Paterson et al. | |
| 7,855,064 B2 | 12/2010 | Paterson et al. | |
| 2002/0025323 A1 | 2/2002 | Paterson et al. | |
| 2004/0013690 A1 | 1/2004 | Portnoy et al. | |
| 2005/0281783 A1* | 12/2005 | Kinch et al. | 424/93.2 |
| 2006/0104991 A1 | 5/2006 | Paterson et al. | |
| 2006/0210540 A1 | 9/2006 | Paterson et al. | |
| 2006/0233835 A1 | 10/2006 | Paterson et al. | |
| 2007/0154953 A1 | 7/2007 | Brunner et al. | |
| 2007/0207171 A1 | 9/2007 | Dubensky et al. | |
| 2009/0202587 A1 | 8/2009 | Paterson et al. | |
| 2011/0129499 A1 | 6/2011 | Maciag et al. | |
| 2011/0142791 A1 | 6/2011 | Shahabi | |
| 2011/0223187 A1 | 9/2011 | Shahabi et al. | |
| 2012/0014984 A1 | 1/2012 | Shahabi et al. | |

FOREIGN PATENT DOCUMENTS

| | | | |
|---|---|---|---|
| EP | 1408048 | 4/2004 | |
| WO | WO 96/39154 | 12/1996 | |
| WO | WO 97/03211 | 1/1997 | |
| WO | WO 99/25376 | 5/1999 | |
| WO | WO 2006/017856 | 2/2006 | |
| WO | WO 2007/061848 | 5/2007 | |
| WO | WO 2008/109155 | 9/2008 | |
| WO | WO 2008/130551 | 10/2008 | |
| WO | WO 2009/143167 | * 11/2009 | ............... C12N 1/21 |

OTHER PUBLICATIONS

Bargmann et al. "The neu oncogene encodes an epidermal growth factor receptor-related protein" Nature 319, 226-230, Jan. 16, 1986.
King et al. "Amplification of a novel v-erbB-related gene in a human mammary carcinoma" Science. 229:974-976, (1985).
Rechsteiner et al. "PEST sequences and regulation by proteolysis" Trends Biochem Sci.21 (7):267-271, Jul. 1996.
Brundage et al. "Expression and phosphorylation of the *Listeria monocytogenes* ActA protein in mammalian cells" Proc Natl Acad Sci USA. 90:11890-11894, (1993).
Camilli et al. "*Listeria monocytogenes* mutants lacking phosphatidylinositol-specific phospholipase C area virulent" J Exp Med 173:751-754, (1991).
Brockstedt et al. "*Listeria*-based cancer vaccines that segregate immunogenicity from toxicity" Proc. Natl. Acad. Sci. U. S. A. 101:13832-13837, (2004).
De Boer et al. "A division inhibitor and a topological specificity factor coded for by the minicell locus determine proper placement of the division septum in *E. coli*" Cell. 56(4):641-9, Feb. 24, 1989.
Miller et al. "Targeted vectors for gene therapy" FASEB J.; 9:190-199. (1995).
Nikodinovic et al. "A second generation snp-derived *Escherichia coli-Streptomyces* shuttle expression vector that is generally transferable by conjugation"Plasmid. 56(3):223-7.Nov. 2006.
Auchtung et al. "Regulation of a *Bacillus subtilis* mobile genetic element by intercellular signaling and the global DNA damage response" Proc. Natl. Acad. Sci. USA 102: 12554-12559, (2005).
Ulmanen et al. "Transcription and translation of foreign genes in *Bacillus subtilis* by the aid of a secretion vector" J. Bacteriol. 162:176-182. (1985).
Gilman et al. "Isolation of sigma-28-specific promoters from *Bacillus subtilis* DNA" Gene 32:11-20. (1984).
Ward et al. "Construction and characterisation of a series of multi-copy promoter-probe plasmid vectors for *Streptomyces* using the aminoglycoside phosphotransferase gene from Tn5 as indicator" Mol Gen Genet. ; 203(3):468-478. Jun. 1986.

(Continued)

*Primary Examiner* — Misook Yu
*Assistant Examiner* — Nelson B Moseley, II
(74) *Attorney, Agent, or Firm* — Mark S. Cohen; Pearl Cohen Zedek Latzer Baratz LLP

(57) ABSTRACT

This invention provides compositions and methods for treating and vaccinating against an Her2/neu antigen-expressing tumor and inducing an immune response against dominant in a non-human animal.

61 Claims, 6 Drawing Sheets

(56) References Cited

OTHER PUBLICATIONS

Glick et al. "Factors affecting the expression of foreign proteins in *Escherichia coli*" J Ind Microbiol; 1:277-282, (1987).
Centiempo et al. "Prokaryotic gene expression in vitro: transcription-translation coupled systems" Biochimie 68:505-515 (1986).
Gottesman. "Bacterial regulation: global regulatory networks" Annu Rev Genet. ; 18:415-41. (1984).
Narang et al. "Improved Phosphotriester Method for the Synthesis of Gene Fragments", Meth. Enzyrnol., 68:90-99. (1979).
Brown et al. "Chemical Synthesis and Cloning of a Tyrosine Trna Gene" Meth Enzymol. 68:109-151, (1979).
Beaucage et al. "Deoxynucleoside phosphoramidites—a new class of key intermediates for deoxypolynucleotide synthesis" Tetra. Lett. 22:1859-1862, (1981).
Nielsen PE "Peptide nucleic acids as therapeutic agents" Curr. Opin. Struct Biol. 9:353.57, (1999).
Naz RK et al. "Novel human prostate-specific cDNA: molecular cloning, expression, and immunobiology of the recombinant protein" Biochem Biophys Res Commun. ; 297(5):1075-84.Oct. 11, 2002.
Wood et al. "Cancer immunotherapy using *Listeria monocytogenes* and listerial virulence factors" Immunol Res. ; 42(1-3):233-45. (2008).
Wallecha et al. "Construction and characterization of an attenuated *Listeria monocytogenes* strain for clinical use in cancer immunotherapy" Clin Vaccine Immunol. 16(1):96-103, Jan. 2009.
Seavey MM. "A novel human Her-2/neu chimeric molecule expressed by *Listeria monocytogenes* can elicit potent HLA-A2 restricted CD8-positive T cell responses and impact the growth and spread of Her-2/neu-positive breast tumors" Clin Cancer Res. 15(3):924-32, Feb. 1, 2009.
Lenz LL. "Stable integration vector for nutrient broth-based selection of attenuated *Listeria monocytogenes* strains with recombinant antigen expression" Clin Vaccine Immunol. 15(9):1414-1419. Sep. 2008.
Disis ML. "Generation of immunity to the Her-2/neu oncogenic protein in patients with breast and ovarian cancer using a peptide-based vaccine" Clin Cancer Res. 5(6):1289-97, Jun. 1999.
International Search report Application No. PCT/US2012/051187 Date of Mailing Jan. 23, 2013.
International Search report Application No. PCT/US 10/56534 Date of Mailing Jun. 27, 2011.
Alexander et al. "Characterization of an Aromatic Amino Acid-Dependent *Listeria monocytogenes* Mutant: Attenuation, Persistence, and Ability to Induce Protective Immunity in Mice" Infection and Immunity, vol. 61, No. 5, p. 2245-2248. May 1993.
Abachin et al. "Formation of D-alanyl-lipoteichoic acid is required for adhesion and virulence of *Listeria monocytogenes*" Molecular Microbiology 43(1), 1-14, (2002).
Singh et al. "Immunoediting sculpts tumor epitopes during immunotherapy" Cancer Res.67(5):1887-92. Mar. 1, 2007.
Lauer et al. "Construction, Characterization, and Use of Two *Listeria monocytogenes* Site-Specific Phage Integration Vectors" Journal of Bacteriology, vol. 184, No. 15, p. 4177-4186. Aug. 2002.
Baloglu et al. "Immune responses of mice to vaccinia virus recombinants expressing either *Listeria monocytogenes* partial listeriolysin or *Brucella abortus* ribosomal L7/L12 protein" Vet Microbiol.; 109(1-2) m, Aug. 10, 2005.
Jiang et al. "Characterization of a mutant *Listeria monocytogenes* strain expressing green fluorescent protein" Acta. Biochim. Biophys Sin (Shanghai), 37(1): 19-24, (2005).
Sun et al. "Isolation of *Listeria monocytogenes* small-plaque mutants defective for intracellular growth and cell-to-cell spread" Infect Immun.; 58(11):3770-3778, Nov. 1990.
Caudy et al. "Fragile X-related protein and VIG associate with the RNA interference machinery" Genes Dev. 16:2491-96, (2002).
Shahabi et al. "Development of a live and highly attenuated *Listeria monocytogenes*-based vaccine for the treatment of Her2/neu-overexpressing cancers in human", Cancer Gene Therapy, 2010, pp. 1-10.
Flint et al., "Overexpression of the erbB-2 proto-oncogene in canine osteosarcoma cell lines and tumors", Vet. Pathol. 41: 291-296, 2004.

Shahabi et al., "Live, attenuated strains of *Listeria* and *Salmonella* as vaccine vectors in cancer treatment", Bioeng. Bugs, 2010, vol. 1, No. 4, pp. 235-243.
Singh et al., "Cancer immunotherapy using recombinant *Listeria monocytogenes* transition from bench to clinic", Human Vaccines, 2011, vol. 7(5), pp. 497-505.
Sewell et al., "Recombinant *Listeria* Vaccines containing PEST sequences are potent immune adjuvants for the tumor-associates antigen human papillomavirus-16 E7", Cancer Res. 2004, vol. 64, pp. 8821-8825.
Kucera et al., "Prostate specific antigen (PSA) in breat and ovarian cancer", Anticancer Res. 1997, vol. 17, No. 6D, pp. 4735-4737.
Dell'Erba et al., "Immunohistochemical reactivity of anti-melanoma monoclonal antibody 225.28S in human breast cancer biopsies", Anticancer Res. 2001, vol. 21, No. 2A, pp. 925-930.
Hjortland et al., "Immunotoxin treatment targeted to the high-molecular weight melanoma-associated antigen prolonging the survival of immunodeficient rats with invasive intracranial human gliobastoma multiforme", J. Neurosurg. 2004, vol. 100, No. 2, pp. 320-327.
Kim et al., "Coexpression of BiP increased antithrombotic hirudin production in recombinant *Saccharomyces cerevisiae*", Journal of Biotechnology, 2003, vol. 101, No. 1, pp. 81-87.
Paterson et al., :*Listeria* based vaccines for cancer treatment, Current opinion in molecular therapeutics, current drugs 2005, vol. 7, No. 5, pp. 454-460.
Gunn et al., "Two *Listeria monocytogenes* vaccine vectors that express different molecular forms of human papilloma virus-16 (HPV-16) E7 induce qualitatively different T cell immunity that correlates with their ability to induce regression of established tumors immortalized by HOV-16", Journal of Immunology 2001, vol. 167, No. 11, pp. 6471-6479.
Parsa Saba et al., "Engineering bacterial vectors for delivery of genes and proteins to antigen-presenting cells", Molecular Pharmaceutics 2007, vol. 4, No. 1, pp. 4-17.
Soussi et al., "Effect of intragastric and intraperitoneal immunization with attenuated and wild-type LACK-expressing *Listeria monocytogenes* on control of murine *Leishmania major* infection", Vaccine 2002, vol. 20, No. 21-22, pp. 2702-2712.
Soussi et al., "*Listeria monocytogenes* as a short-lived delivery system for the induction of type 1 cell-mediated immunity against the p36/LACK antigen of *Leishmania major*", Infection and Immunity 2000, vol. 68, No. 3, pp. 1498-1506.
Frankel et al., "Induction of a cell-mediated immune response to HIV gag using *Listeria monocytogenes* as a live vaccine vector", J. Immunol. 155: 4766-4774. 1995.
Mata et al., "Evaluation of a recombinant *Listeria monocytogenes* expressing an HIV protein that protects mice against viral challenge", Vaccine 19:1435-45, 2001.
Boyer et al., "DNA prime *Listeria* boost induces a cellular immune response to SIV antigens in the Rhesus Macaque model that is capable of limited suppression of SIV239 viral replication", Virology. 333: 88-101, 2005.
Loessner et al., "Structural proteins and DNA characteristics of 14 *Listeria* typing bacteriophages", J. Gen. Virol.1994 75:701-710.
Rogers et al., "Amino acid sequences common to rapidly degraded proteins: the PEST hypothesis", Science 1986; 234(4774):364-8.
Kyte et al. (Kyte, J and Dootlittle, RF. J. Mol. Biol. 157, 105 (1982).
Garay-Malpardita et al. Bioinformatics. Jun. 2005;21 Suppl 1:i169-76.
Pucci et al, "*Staphylococcus haemolyticus* Contains Two D-Glutamic Acid Biosynthetic Activities, a Glutamate Racemase and a D-Amino Acid Transaminase" 1995, J Bacteriol. 177: 336-342.
Sizemore et al, 1995, Science 270: 299-302.
Strych et al, "Mutant Analysis Shows that Alanine Racemases from *Pseudomonas aeruginosa* and *Escherichia coli* Are Dimeric" 2002, J. Bacteriol. 184:4321-4325.
Tauch et al, 2002, J. Biotechnol 99:79-91.
Bron et al, "Use of the alr Gene as a Food-Grade Selection Marker in Lactic Acid Bacteria" 2002, Appl Environ Microbiol, 68: 5663-70.
Dzojic H et al (Adenovirus-mediated CD40 ligand therapy induces tumor cell apoptosis and systemic immunity in the Tramp-C2 mouse prostate cancer model. Prostate. Jun. 1, 2006;66(8):831-8).

(56) References Cited

OTHER PUBLICATIONS

Naruishi K et al (Adenoviral vector-mediated RTVP-1 gene-modified tumor cell-based vaccine suppresses the development of experimental prostate cancer. Cancer Gene Ther. Jul. 2006;13(7):658-63).
Sehgal I et al "Prostate cancer cells show elevated urokinase receptor in a mouse model of metastasis " Cancer Cell Int. Aug. 23, 2006;6:21.
Heinrich JE et al (Vaccination against prostate cancer using a live tissue factor deficient cell line in Lobund-Wistar rats. Cancer Immunol Immunother 2007;56(5):725-30).
Uenaka A et al (T cell immunomonitoring and tumor responses in patients immunized with a complex of cholesterol-bearing hydrophobized pullulan (CHP) and NY-ESO-1 protein. Cancer Immun. Apr. 19, 2007;7:9).
Thomas-Kaskel AK et al (Vaccination of advanced prostate cancer patients with PSCA and PSA peptide-loaded dendritic cells induces DTH responses that correlate with superior overall survival. Int J Cancer. Nov. 15, 2006;119(10):2428-34).
Milligan (1993) "Current concepts in antisense drug design", J. Med. Chem. 36:1923-1937; Antisense Research and Applications (1993, CRC Press).
Mata (1997), "A hexameric phosphorothioate oligonucleotide telomerase inhibitor arrests growth of Burkitt's lymphoma cells in vitro and in vivo", Toxicol. Appi. Pharmacol. 144:189-197.
Strauss-Soukup, "Effects of Neutralization Pattern and Stereochemistry on DNA Bending by Methylphosphonate Substitutions ",(1997) Biochemistry 36:8692-8698.
Samstag, "Synthesis and properties of new antisense oligodeoxynucleotides containing benzylphosphonate linkages", (1996) Antisense Nucleic Acid Drug Dev. 6:153-156.
Landy, A., "Mechanistic and structural complexity in the site-specific recombination pathways of Int and FLP", Current Opinion in Genetics & Development, 3:699-707; 1993).
Belt et al., "Efficient cDNA cloning by direct phenotypic correction of a mutant human cell line (HPRT2) using an Epstein-Barr virus-derived cDNA expression vector", Nucleic Acids Res. 1991, 19, 4861-4866.
Mazda et al. "Extremely efficient gene transfection into lymphohematopoietic cell lines by Epstein-Barr virus-based vectors", J. Immunol. Methods 1997, 204, 143-151.
Ogasawara et al., "A strategy for making synthetic peptide vaccines", Proc. Nati. Acad. Sci. USA 1992, vol. 89, pp. 8995-8999.
Verch et al., "*Listeria monocytogenes*-Based Antibiotic Resistance Gene-Free Antigen Delivery System Applicable to Other Bacterial Vectors and DNA Vaccines" Infect Immun, 2004. 72(11):6418-25.
Smith and Youngman, "Use of a new integrational vector to investigate comparement-specific expression of the *Bacillus subtilis* spoIIM gene", Biochimie. 1992; 74 (7-8) p. 705-711.
Clifton et al., "Overcoming cancer immune tolerance and escape", Clinical Cancer Research: an Official Journal of the American Association for Cancer, vol. 15, No. 3, 2009, pp. 749-751.
Singh et al., "Fusion to listeriolysin O and delivery by *Listeria monocytogenes* enhances the immunogenicity of Her-2/neu and reveals subdominant epitopes in the FVB/N mouse", The Journal of Immunology, vol. 175, No. 6, 2005, pp. 3663-3673.
Shahabi et al., "Development of a *Listeria monocytogenes* based vaccine against prostate cancer", Cancer Immunology, vol. 57, No. 9, 2008, pp. 1301-1313.
Wallecha et al., "Multiple effector mechanisms induced by recombinant *Listeria monocytogenes* anticancer immunotherapeutics", Advances in Applied Microbiology, vol. 66, 2009, pp. 1-27.
Angelakopoulos et al., "Safety and shedding of an attenuated strain of *Listeria monocytogenes* with a delection of actA/plcB in adult volunteers: a dose escalation study of oral innoculation", Infection and Immunity 2002, 70(7): 3592-3601.
Li et al., "Conditional lethality yields a new vaccine strain of *Listeria monocytogenes* for the induction of cell-mediated immunity", Infection and Immunity, 2005, 73(8): 5065-5073.
Shahabi et al. "A live, attenuated Listeria-based immunotherapeutic for the treatment of breast cancer", 2009 ASCO Breast cancer Symposium, Oct. 8, 2009, abstract only.
European Search Report for European Application No. 10830785.1 mailed on Dec. 10, 2013.

* cited by examiner

A

B

1- Negative *Lm*-control
2- *Lm*-LLO-ChHer2
3- ADXS31-164

Spleens

SEQUENCE LISTING

```
<160> NUMBER OF SEQ ID NOS: 68

<210> SEQ ID NO 1
<211> LENGTH: 1263
<212> TYPE: DNA
<213> ORGANISM: Artificial Sequence
<220> FEATURE:
<223> OTHER INFORMATION: Her-2 chimeric protein

<400> SEQUENCE: 1
gagacccacc tggacatgct ccgccacctc taccagggct gccaggtggt gcagggaaac      60
ctggaactca cctacctgcc caccaatgcc agcctgtcct tcctgcagga tatccaggag     120
gtgcagggct acgtgctcat cgctcacaac caagtgaggc aggtcccact gcagaggctg     180
cggattgtgc gaggcaccca gctctttgag gacaactatg ccctgccgt gctagacaat      240 ggagacccgc tgaacaatac caccctgtc acaggggcct ccccaggagg cctgcgggag      300
ctgcagcttc gaagcctcac agagatcttg aaaggagggg tcttgatcca gcggaacccc     360
cagctctgct accaggacac gattttgtgg aagaatatcc aggagtttgc tggctgcaag     420
aagatctttg ggagcctggc atttctgccg gagagctttg atggggaccc agcctccaac     480
actgccccgc tccagccaga gcagctccaa gtgtttgaga ctctggaaga gatcacaggt     540
tacctataca tctcagcatg gccggacagc ctgcctgacc tcagcgtctt ccagaacctg     600
caagtaatcc ggggacgaat tctgcacaat ggcgcctact cgctgaccct gcaagggctg     660
ggcatcagct ggctggggct gcgctcactg agggaactgg gcagtggact ggccctcatc     720
caccataaca cccacctctg cttcgtgcac acggtgcct gggaccagct cttttcggaac     780 ccgcaccaag ctctgctcca cactgccaac cggccagagg acgagtgtgt gggcgagggc     840
ctggcctgcc accagctgtg cgcccgaggg cagcagaaga tccggaagta cacgatgcgg     900
agactgctgc aggaaacgga gctggtggag ccgctgacac tagcggagc gatgcccaac      960 caggcgcaga tgcggatcct gaaagagacg gagctgagga aggtgaaggt gcttggatct    1020
ggcgcttttg gcacagtcta caagggcatc tggatccctg atggggagaa tgtgaaaatt    1080
```

```
ccagtggcca tcaaagtgtt gagggaaaac acatccccca aagccaacaa agaaatctta    1140
gacgaagcat acgtgatggc tggtgtgggc tccccatatg tctcccgcct tctgggcatc    1200
tgcctgacat ccacggtgca gctggtgaca cagcttatgc cctatggctg cctcttagac    1260
taa                                                                  1263
```

<210> SEQ ID NO 2
<211> LENGTH: 420
<212> TYPE: PRT
<213> ORGANISM: Artificial Sequence
<220> FEATURE:
<223> OTHER INFORMATION: Her-2 chimeric protein

<400> SEQUENCE: 2

```
Glu Thr His Leu Asp Met Leu Arg His Leu Tyr Gln Gly Cys Gln Val
1               5                   10                  15

Val Gln Gly Asn Leu Glu Leu Thr Tyr Leu Pro Thr Asn Ala Ser Leu
            20                  25                  30

Ser Phe Leu Gln Asp Ile Gln Glu Val Gln Gly Tyr Val Leu Ile Ala
        35                  40                  45

His Asn Gln Val Arg Gln Val Pro Leu Gln Arg Leu Arg Ile Val Arg
    50                  55                  60

Gly Thr Gln Leu Phe Glu Asp Asn Tyr Ala Leu Ala Val Leu Asp Asn
65                  70                  75                  80

Gly Asp Pro Leu Asn Asn Thr Thr Pro Val Thr Gly Ala Ser Pro Gly
                85                  90                  95

Gly Leu Arg Glu Leu Gln Leu Arg Ser Leu Thr Glu Ile Leu Lys Gly
            100                 105                 110

Gly Val Leu Ile Gln Arg Asn Pro Gln Leu Cys Tyr Gln Asp Thr Ile
        115                 120                 125

Leu Trp Lys Asn Ile Gln Glu Phe Ala Gly Cys Lys Lys Ile Phe Gly
    130                 135                 140

Ser Leu Ala Phe Leu Pro Glu Ser Phe Asp Gly Asp Pro Ala Ser Asn
145                 150                 155                 160

Thr Ala Pro Leu Gln Pro Glu Gln Leu Gln Val Phe Glu Thr Leu Glu
                165                 170                 175

Glu Ile Thr Gly Tyr Leu Tyr Ile Ser Ala Trp Pro Asp Ser Leu Pro
            180                 185                 190

Asp Leu Ser Val Phe Gln Asn Leu Gln Val Ile Arg Gly Arg Ile Leu
        195                 200                 205

His Asn Gly Ala Tyr Ser Leu Thr Leu Gln Gly Leu Gly Ile Ser Trp
    210                 215                 220

Leu Gly Leu Arg Ser Leu Arg Glu Leu Gly Ser Gly Leu Ala Leu Ile
225                 230                 235                 240

His His Asn Thr His Leu Cys Phe Val His Thr Val Pro Trp Asp Gln
                245                 250                 255

Leu Phe Arg Asn Pro His Gln Ala Leu Leu His Thr Ala Asn Arg Pro
            260                 265                 270

Glu Asp Glu Cys Val Gly Glu Gly Leu Ala Cys His Gln Leu Cys Ala
        275                 280                 285

Arg Gly Gln Gln Lys Ile Arg Lys Tyr Thr Met Arg Arg Leu Leu Gln
    290                 295                 300

Glu Thr Glu Leu Val Glu Pro Leu Thr Pro Ser Gly Ala Met Pro Asn
305                 310                 315                 320
```

Gln Ala Gln Met Arg Ile Leu Lys Glu Thr Glu Leu Arg Lys Val Lys
            325                 330                 335

Val Leu Gly Ser Gly Ala Phe Gly Thr Val Tyr Lys Gly Ile Trp Ile
        340                 345                 350

Pro Asp Gly Glu Asn Val Lys Ile Pro Val Ala Ile Lys Val Leu Arg
    355                 360                 365

Glu Asn Thr Ser Pro Lys Ala Asn Lys Glu Ile Leu Asp Glu Ala Tyr
370                 375                 380

Val Met Ala Gly Val Gly Ser Pro Tyr Val Ser Arg Leu Leu Gly Ile
385                 390                 395                 400

Cys Leu Thr Ser Thr Val Gln Leu Val Thr Gln Leu Met Pro Tyr Gly
            405                 410                 415

Cys Leu Leu Asp
            420

<210> SEQ ID NO 3
<211> LENGTH: 1323
<212> TYPE: DNA
<213> ORGANISM: Listeria monocytogenes

<400> SEQUENCE: 3
atgaaaaaaa taatgctagt tttattaca cttatattag ttagtctacc aattgcgcaa      60
caaactgaag caaggatgc atctgcattc aataaagaaa attcaatttc atccatggca     120
ccaccagcat ctccgcctgc aagtcctaag acgccaatcg aaagaaaca cgcggatgaa     180 atcgataagt atatacaagg attggattac aataaaaaca atgtattagt ataccacgga     240
gatgcagtga caaatgtgcc gccaagaaaa ggttacaaag atggaaatga atatattgtt     300
gtggagaaaa agaagaaatc catcaatcaa aataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatagttgta aaaaatgcca ctaaatcaaa cgttaacaac     540 gcagtaaaata cattagtgga agatggaat gaaaaatatg ctcaagctta tccaaatgta     600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
aatgaaccta caagaccttc cagattttc ggcaaagctg ttactaaaga gcagttgcaa     840
gcgcttggag tgaatgcaga aaatcctcct gcatatatct caagtgtggc gtatggccgt     900
caagtttatt tgaaattatc aactaattcc catagtacta agtaaaagc tgcttttgat     960 gctgccgtaa gcgaaaatc tgtctcaggt gatgtagaac taacaaatat catcaaaaat    1020
tcttccttca agccgtaat ttacggaggt tccgcaaaag atgaagttca aatcatcgac    1080 ggcaaccctcg gagacttacg cgatattttg aaaaaaggcg ctactttaa tcgagaaaca    1140 ccaggagttc ccattgctta taacaaaac ttcctaaaag acaatgaatt agctgttatt    1200
aaaaacaact cagaatatat tgaaacaact tcaaaagctt atacagatgg aaaaattaac    1260
atcgatcact ctggaggata cgttgctcaa ttcaacattt cttgggatga agtaaattat    1320
gat                                                                  1323

<210> SEQ ID NO 4
<211> LENGTH: 441
<212> TYPE: PRT

<213> ORGANISM: Listeria monocytogenes

<400> SEQUENCE: 4

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400
```

-continued

```
Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
        420                 425                 430

Ile Ser Trp Asp Glu Val Asn Tyr Asp
        435                 440

<210> SEQ ID NO 5
<211> LENGTH: 14
<212> TYPE: PRT
<213> ORGANISM: Listeria monocytogenes

<400> SEQUENCE: 5

Lys Thr Glu Glu Gln Pro Ser Glu Val Asn Thr Gly Pro Arg
1               5                   10

<210> SEQ ID NO 6
<211> LENGTH: 28
<212> TYPE: PRT
<213> ORGANISM: Listeria monocytogenes

<400> SEQUENCE: 6

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 7
<211> LENGTH: 20
<212> TYPE: PRT
<213> ORGANISM: Listeria monocytogenes

<400> SEQUENCE: 7

Lys Asn Glu Glu Val Asn Ala Ser Asp Phe Pro Pro Pro Pro Thr Asp
1               5                   10                  15

Glu Glu Leu Arg
            20

<210> SEQ ID NO 8
<211> LENGTH: 33
<212> TYPE: PRT
<213> ORGANISM: Listeria monocytogenes

<400> SEQUENCE: 8

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 9
<211> LENGTH: 17
<212> TYPE: PRT
<213> ORGANISM: Streptococcus pyogenes

<400> SEQUENCE: 9

Lys Gln Asn Thr Ala Ser Thr Glu Thr Thr Thr Thr Asn Glu Gln Pro
1               5                   10                  15

Lys

<210> SEQ ID NO 10
```

-continued

```
<211> LENGTH: 17
<212> TYPE: PRT
<213> ORGANISM: Streptococcus equisimilis

<400> SEQUENCE: 10

Lys Gln Asn Thr Ala Asn Thr Glu Thr Thr Thr Thr Asn Glu Gln Pro
1               5                   10                  15
Lys

<210> SEQ ID NO 11
<211> LENGTH: 9
<212> TYPE: PRT
<213> ORGANISM: Homo sapiens

<400> SEQUENCE: 11

His Leu Tyr Gln Gly Cys Gln Val Val
1               5

<210> SEQ ID NO 12
<211> LENGTH: 9
<212> TYPE: PRT
<213> ORGANISM: Homo sapiens

<400> SEQUENCE: 12

Lys Ile Phe Gly Ser Leu Ala Phe Leu
1               5

<210> SEQ ID NO 13
<211> LENGTH: 9
<212> TYPE: PRT
<213> ORGANISM: Homo sapiens

<400> SEQUENCE: 13

Arg Leu Leu Gln Glu Thr Glu Leu Val
1               5

<210> SEQ ID NO 14
<211> LENGTH: 55
<212> TYPE: PRT
<213> ORGANISM: Mus musculus

<400> SEQUENCE: 14

Gly Gly Thr Cys Ala Cys Ala Gly Cys Thr Gly Ala Gly Gly Ala Cys
1               5                   10                  15

Gly Gly Ala Ala Cys Ala Cys Ala Gly Cys Gly Thr Thr Gly Thr Gly
                20                  25                  30

Ala Gly Ala Ala Ala Thr Gly Cys Ala Gly Cys Ala Ala Gly Cys Cys
                35                  40                  45

Cys Thr Gly Thr Gly Cys Thr
                50                  55

<210> SEQ ID NO 15
<211> LENGTH: 60
<212> TYPE: PRT
<213> ORGANISM: Mus musculus

<400> SEQUENCE: 15

Cys Gly Ala Gly Thr Gly Thr Gly Cys Thr Ala Thr Gly Gly Thr Cys
1               5                   10                  15

Thr Gly Gly Gly Cys Ala Thr Gly Gly Ala Gly Cys Ala Cys Cys Thr
                20                  25                  30

Thr Cys Gly Ala Gly Gly Gly Cys Gly Ala Gly Gly Gly Cys Cys
```

```
                35                  40                  45
Ala Thr Cys Ala Cys Cys Ala Gly Thr Gly Ala Cys
    50                  55                  60

<210> SEQ ID NO 16
<211> LENGTH: 60
<212> TYPE: PRT
<213> ORGANISM: Mus musculus

<400> SEQUENCE: 16

Ala Ala Thr Gly Thr Cys Cys Ala Gly Gly Ala Gly Thr Thr Thr Gly
1               5                   10                  15

Ala Thr Gly Gly Cys Thr Gly Cys Ala Ala Gly Ala Ala Gly Ala Thr
                20                  25                  30

Cys Thr Thr Thr Gly Gly Gly Ala Gly Cys Cys Thr Gly Gly Cys Ala
            35                  40                  45

Thr Thr Thr Thr Thr Gly Cys Cys Gly Gly Ala Gly
    50                  55                  60

<210> SEQ ID NO 17
<211> LENGTH: 60
<212> TYPE: PRT
<213> ORGANISM: Mus musculus

<400> SEQUENCE: 17

Ala Gly Cys Thr Thr Thr Gly Ala Thr Gly Gly Gly Ala Cys Cys
1               5                   10                  15

Cys Cys Thr Cys Cys Thr Cys Cys Gly Gly Cys Ala Thr Thr Gly Cys
                20                  25                  30

Thr Cys Cys Gly Cys Thr Gly Ala Gly Cys Cys Thr Gly Ala Gly
            35                  40                  45

Cys Ala Gly Cys Thr Cys Cys Ala Ala Gly Thr Gly
    50                  55                  60

<210> SEQ ID NO 18
<211> LENGTH: 60
<212> TYPE: PRT
<213> ORGANISM: Mus musculus

<400> SEQUENCE: 18

Thr Thr Cys Gly Ala Ala Ala Cys Cys Cys Thr Gly Gly Ala Gly Gly
1               5                   10                  15

Ala Gly Ala Thr Cys Ala Cys Ala Gly Gly Thr Thr Ala Cys Cys Thr
                20                  25                  30

Gly Thr Ala Cys Ala Thr Cys Thr Cys Ala Gly Cys Ala Thr Gly Gly
            35                  40                  45

Cys Cys Ala Gly Ala Cys Ala Gly Thr Cys Thr Cys
    50                  55                  60

<210> SEQ ID NO 19
<211> LENGTH: 60
<212> TYPE: PRT
<213> ORGANISM: Mus musculus

<400> SEQUENCE: 19

Cys Gly Thr Gly Ala Cys Cys Thr Cys Ala Gly Thr Gly Thr Cys Thr
1               5                   10                  15

Thr Cys Cys Ala Gly Ala Ala Cys Cys Thr Cys Gly Ala Ala Thr
                20                  25                  30
```

```
Cys Ala Thr Thr Cys Gly Gly Gly Ala Cys Gly Ala Thr Thr
            35                  40                  45

Cys Thr Cys Cys Ala Cys Gly Ala Thr Gly Gly Cys
        50                  55                  60

<210> SEQ ID NO 20
<211> LENGTH: 60
<212> TYPE: PRT
<213> ORGANISM: Mus musculus

<400> SEQUENCE: 20

Gly Cys Gly Thr Ala Cys Thr Cys Ala Thr Gly Ala Cys Ala Cys
1               5                   10                  15

Thr Gly Cys Ala Ala Gly Gly Cys Cys Thr Gly Gly Gly Ala Thr
                20                  25                  30

Cys Cys Ala Cys Thr Cys Gly Cys Thr Gly Gly Gly Cys Thr Gly
            35                  40                  45

Cys Gly Cys Thr Cys Ala Cys Thr Gly Cys Gly
        50                  55                  60

<210> SEQ ID NO 21
<211> LENGTH: 60
<212> TYPE: PRT
<213> ORGANISM: Mus musculus

<400> SEQUENCE: 21

Gly Ala Gly Cys Thr Gly Gly Cys Ala Gly Thr Gly Gly Ala Thr
1               5                   10                  15

Thr Gly Gly Cys Thr Cys Thr Gly Ala Thr Thr Cys Ala Cys Cys Gly
                20                  25                  30

Cys Ala Ala Cys Gly Cys Cys Ala Thr Cys Thr Cys Thr Gly Cys
            35                  40                  45

Thr Thr Thr Gly Thr Ala Cys Ala Cys Ala Cys Thr
        50                  55                  60

<210> SEQ ID NO 22
<211> LENGTH: 60
<212> TYPE: PRT
<213> ORGANISM: Mus musculus

<400> SEQUENCE: 22

Gly Thr Ala Cys Cys Thr Thr Gly Gly Ala Cys Cys Ala Gly Cys
1               5                   10                  15

Thr Cys Thr Cys Cys Gly Gly Ala Ala Cys Cys Ala Cys Ala
                20                  25                  30

Thr Cys Ala Gly Gly Cys Cys Cys Thr Gly Cys Thr Cys Ala Cys
            35                  40                  45

Ala Gly Thr Gly Gly Gly Ala Ala Cys Cys Gly Gly
        50                  55                  60

<210> SEQ ID NO 23
<211> LENGTH: 60
<212> TYPE: PRT
<213> ORGANISM: Mus musculus

<400> SEQUENCE: 23

Cys Cys Gly Gly Ala Ala Gly Ala Gly Ala Thr Thr Gly Thr Gly
1               5                   10                  15

Gly Thr Cys Thr Cys Gly Ala Gly Gly Cys Thr Thr Gly Gly Thr
                20                  25                  30
```

Cys Thr Gly Thr Ala Ala Cys Thr Cys Ala Cys Thr Gly Thr Gly Thr
            35                  40                  45

Gly Cys Cys Ala Cys Gly Gly Cys Ala Cys
    50                  55                  60

<210> SEQ ID NO 24
<211> LENGTH: 60
<212> TYPE: PRT
<213> ORGANISM: Mus musculus

<400> SEQUENCE: 24

Thr Gly Cys Thr Gly Gly Gly Gly Cys Cys Ala Gly Gly Gly Cys
1               5                   10                  15

Cys Cys Ala Cys Cys Cys Ala Gly Thr Gly Thr Gly Thr Cys Ala Ala
                20                  25                  30

Cys Thr Gly Cys Ala Gly Thr Cys Ala Thr Thr Thr Cys Cys Thr Thr
            35                  40                  45

Cys Gly Gly Gly Gly Cys Cys Ala Gly Ala Gly
    50                  55                  60

<210> SEQ ID NO 25
<211> LENGTH: 57
<212> TYPE: PRT
<213> ORGANISM: Mus musculus

<400> SEQUENCE: 25

Cys Gly Cys Cys Ala Gly Cys Gly Gly Ala Gly Cys Ala Ala Thr
1               5                   10                  15

Gly Cys Cys Cys Ala Ala Cys Cys Ala Gly Gly Cys Thr Cys Ala Gly
                20                  25                  30

Ala Thr Gly Cys Gly Gly Ala Thr Cys Cys Thr Ala Ala Ala Ala Gly
            35                  40                  45

Ala Gly Ala Cys Gly Gly Ala Gly Cys
    50                  55

<210> SEQ ID NO 26
<211> LENGTH: 60
<212> TYPE: PRT
<213> ORGANISM: Mus musculus

<400> SEQUENCE: 26

Thr Ala Ala Gly Gly Ala Ala Gly Gly Thr Gly Ala Ala Gly Gly Thr
1               5                   10                  15

Gly Cys Thr Thr Gly Gly Ala Thr Cys Ala Gly Gly Ala Gly Cys Thr
                20                  25                  30

Thr Thr Thr Gly Gly Cys Ala Cys Thr Gly Thr Cys Thr Ala Cys Ala
            35                  40                  45

Ala Gly Gly Gly Cys Ala Thr Cys Thr Gly Gly Ala
    50                  55                  60

<210> SEQ ID NO 27
<211> LENGTH: 60
<212> TYPE: PRT
<213> ORGANISM: Mus musculus

<400> SEQUENCE: 27

Thr Cys Cys Cys Ala Gly Ala Thr Gly Gly Gly Ala Gly Ala Ala
1               5                   10                  15

Thr Gly Thr Gly Ala Ala Ala Ala Thr Cys Cys Cys Cys Gly Thr Gly

```
                20                  25                  30
Gly Cys Thr Ala Thr Cys Ala Ala Gly Gly Thr Gly Thr Thr Gly Ala
            35                  40                  45
Gly Ala Gly Ala Ala Ala Cys Ala Cys Ala Thr
        50                  55                  60
```

<210> SEQ ID NO 28
<211> LENGTH: 60
<212> TYPE: PRT
<213> ORGANISM: Mus musculus

<400> SEQUENCE: 28

```
Cys Thr Cys Cys Thr Ala Ala Gly Cys Cys Ala Ala Cys Ala Ala
1               5                   10                  15
Ala Gly Ala Ala Ala Thr Thr Cys Thr Ala Gly Ala Thr Gly Ala Ala
            20                  25                  30
Gly Cys Gly Thr Ala Thr Gly Thr Gly Ala Thr Gly Gly Cys Thr Gly
            35                  40                  45
Gly Thr Gly Thr Gly Gly Gly Thr Thr Cys Thr Cys
        50                  55                  60
```

<210> SEQ ID NO 29
<211> LENGTH: 60
<212> TYPE: PRT
<213> ORGANISM: Mus musculus

<400> SEQUENCE: 29

```
Cys Gly Thr Ala Thr Gly Thr Gly Thr Cys Cys Cys Gly Cys Cys Thr
1               5                   10                  15
Cys Cys Thr Gly Gly Gly Cys Ala Thr Cys Thr Gly Cys Cys Thr Gly
            20                  25                  30
Ala Cys Ala Thr Cys Cys Ala Cys Ala Gly Thr Ala Cys Ala Gly Cys
            35                  40                  45
Thr Gly Gly Thr Gly Ala Cys Ala Cys Ala Gly Cys
        50                  55                  60
```

<210> SEQ ID NO 30
<211> LENGTH: 60
<212> TYPE: PRT
<213> ORGANISM: Mus musculus

<400> SEQUENCE: 30

```
Thr Thr Ala Thr Gly Cys Cys Cys Thr Ala Cys Gly Gly Cys Thr Gly
1               5                   10                  15
Cys Cys Thr Thr Cys Thr Gly Gly Ala Cys Cys Ala Thr Gly Thr Cys
            20                  25                  30
Cys Gly Ala Gly Ala Ala Cys Ala Cys Cys Gly Ala Gly Gly Thr Cys
            35                  40                  45
Gly Cys Cys Thr Ala Gly Gly Cys Thr Cys Cys Cys
        50                  55                  60
```

<210> SEQ ID NO 31
<211> LENGTH: 60
<212> TYPE: PRT
<213> ORGANISM: Mus musculus

<400> SEQUENCE: 31

```
Ala Gly Gly Ala Cys Cys Thr Gly Cys Thr Cys Ala Ala Cys Thr Gly
1               5                   10                  15
```

Gly Thr Gly Thr Gly Thr Cys Ala Gly Thr Thr Gly Cys Cys
            20                  25                  30

Ala Ala Gly Gly Gly Gly Ala Thr Gly Ala Gly Cys Thr Ala Cys Cys
        35                  40                  45

Thr Gly Gly Ala Gly Gly Ala Cys Gly Thr Gly Cys
    50                  55                  60

<210> SEQ ID NO 32
<211> LENGTH: 60
<212> TYPE: PRT
<213> ORGANISM: Mus musculus

<400> SEQUENCE: 32

Gly Gly Cys Thr Thr Gly Thr Ala Cys Ala Cys Ala Gly Gly Ala
1               5                   10                  15

Cys Cys Thr Gly Gly Cys Thr Gly Cys Cys Gly Gly Ala Ala Thr
            20                  25                  30

Gly Thr Gly Cys Thr Ala Gly Thr Cys Ala Ala Gly Ala Gly Thr Cys
        35                  40                  45

Cys Cys Ala Ala Cys Cys Ala Cys Gly Thr Cys Ala
    50                  55                  60

<210> SEQ ID NO 33
<211> LENGTH: 60
<212> TYPE: PRT
<213> ORGANISM: Mus musculus

<400> SEQUENCE: 33

Ala Gly Ala Thr Thr Ala Cys Ala Gly Ala Thr Thr Cys Gly Gly
1               5                   10                  15

Gly Cys Thr Gly Gly Cys Thr Cys Gly Gly Cys Thr Gly Cys Thr Gly
            20                  25                  30

Gly Ala Cys Ala Thr Thr Gly Ala Thr Gly Ala Gly Ala Cys Ala Gly
        35                  40                  45

Ala Gly Thr Ala Cys Cys Ala Thr Gly Cys Ala Gly
    50                  55                  60

<210> SEQ ID NO 34
<211> LENGTH: 60
<212> TYPE: PRT
<213> ORGANISM: Mus musculus

<400> SEQUENCE: 34

Ala Thr Gly Gly Gly Gly Gly Cys Ala Ala Gly Gly Thr Gly Cys Cys
1               5                   10                  15

Cys Ala Thr Cys Ala Ala Ala Thr Gly Gly Ala Thr Gly Gly Cys Ala
            20                  25                  30

Thr Thr Gly Gly Ala Ala Thr Cys Thr Ala Thr Cys Thr Cys Ala
        35                  40                  45

Gly Ala Cys Gly Cys Cys Gly Gly Thr Thr Cys Ala
    50                  55                  60

<210> SEQ ID NO 35
<211> LENGTH: 60
<212> TYPE: PRT
<213> ORGANISM: Mus musculus

<400> SEQUENCE: 35

Cys Cys Cys Ala Thr Cys Ala Gly Ala Gly Thr Gly Ala Thr Gly Thr
1               5                   10                  15

```
Gly Thr Gly Gly Ala Gly Cys Thr Ala Thr Gly Gly Ala Gly Thr Gly
            20                  25                  30

Ala Cys Thr Gly Thr Gly Thr Gly Gly Ala Gly Cys Thr Gly Thr Ala
            35                  40                  45

Thr Gly Ala Cys Thr Thr Thr Gly Gly Gly Gly
            50                  55                  60

<210> SEQ ID NO 36
<211> LENGTH: 59
<212> TYPE: PRT
<213> ORGANISM: Mus musculus

<400> SEQUENCE: 36

Cys Cys Ala Ala Ala Cys Cys Thr Ala Cys Gly Ala Thr Gly Gly
1               5                   10                  15

Ala Ala Thr Cys Cys Ala Gly Cys Cys Gly Gly Ala Gly
            20                  25                  30

Ala Thr Cys Cys Thr Gly Ala Thr Thr Thr Gly Cys Thr Gly Gly
            35                  40                  45

Ala Gly Ala Ala Gly Gly Ala Gly Ala Ala
            50                  55

<210> SEQ ID NO 37
<211> LENGTH: 58
<212> TYPE: PRT
<213> ORGANISM: Mus musculus

<400> SEQUENCE: 37

Cys Gly Cys Cys Thr Ala Cys Thr Cys Ala Gly Cys Cys Thr Cys
1               5                   10                  15

Cys Ala Ala Thr Cys Thr Gly Cys Ala Cys Cys Ala Thr Thr Gly Ala
            20                  25                  30

Thr Gly Thr Cys Thr Ala Cys Ala Thr Gly Ala Thr Thr Ala Thr Gly
            35                  40                  45

Gly Thr Cys Ala Ala Thr Gly Thr Thr
            50                  55

<210> SEQ ID NO 38
<211> LENGTH: 54
<212> TYPE: PRT
<213> ORGANISM: Mus musculus

<400> SEQUENCE: 38

Gly Gly Ala Thr Gly Ala Thr Thr Gly Ala Cys Thr Cys Thr Gly Ala
1               5                   10                  15

Ala Thr Gly Thr Cys Gly Cys Cys Gly Ala Gly Ala Thr Thr Cys
            20                  25                  30

Cys Gly Gly Gly Ala Gly Thr Thr Gly Thr Gly Thr Cys Ala Gly
            35                  40                  45

Ala Ala Thr Thr Thr Thr
    50

<210> SEQ ID NO 39
<211> LENGTH: 52
<212> TYPE: PRT
<213> ORGANISM: Mus musculus

<400> SEQUENCE: 39

Cys Ala Cys Gly Thr Ala Thr Gly Gly Cys Gly Ala Gly Gly Gly Ala
```

```
                1               5                  10                 15
Cys Cys Cys Cys Cys Ala Gly Cys Gly Thr Thr Thr Thr Gly Thr Gly
                    20                  25                  30

Gly Thr Cys Ala Thr Cys Cys Ala Gly Ala Ala Cys Gly Ala Gly Gly
                35                  40                  45

Ala Cys Thr Thr
        50
```

<210> SEQ ID NO 40
<211> LENGTH: 60
<212> TYPE: PRT
<213> ORGANISM: Mus musculus

<400> SEQUENCE: 40

```
Cys Cys Cys Ala Gly Gly Cys Ala Gly Ala Ala Cys Cys Cys Cys Ala
1               5                   10                  15

Gly Ala Gly Gly Gly Gly Cys Thr Gly Cys Gly Gly Ala Gly Cys
                20                  25                  30

Thr Gly Cys Ala Gly Cys Thr Thr Cys Gly Ala Ala Gly Thr Cys Thr
                35                  40                  45

Cys Ala Cys Ala Gly Ala Gly Ala Thr Cys Cys Thr
        50                  55                  60
```

<210> SEQ ID NO 41
<211> LENGTH: 60
<212> TYPE: PRT
<213> ORGANISM: Mus musculus

<400> SEQUENCE: 41

```
Gly Ala Ala Gly Gly Gly Ala Gly Gly Ala Gly Thr Thr Thr Thr Gly
1               5                   10                  15

Ala Thr Cys Cys Gly Thr Gly Gly Ala Ala Cys Cys Cys Thr Cys
                20                  25                  30

Ala Gly Cys Thr Cys Thr Gly Cys Thr Ala Cys Ala Gly Gly Ala
                35                  40                  45

Cys Ala Thr Gly Gly Thr Thr Thr Thr Gly Thr Gly
        50                  55                  60
```

<210> SEQ ID NO 42
<211> LENGTH: 60
<212> TYPE: PRT
<213> ORGANISM: Mus musculus

<400> SEQUENCE: 42

```
Cys Cys Gly Gly Gly Cys Cys Thr Gly Thr Cys Cys Ala Cys Cys Thr
1               5                   10                  15

Thr Gly Thr Gly Cys Cys Cys Cys Gly Cys Cys Thr Gly Cys Ala
                20                  25                  30

Ala Ala Gly Ala Cys Ala Ala Thr Cys Ala Cys Thr Gly Thr Thr Gly
                35                  40                  45

Gly Gly Gly Thr Gly Ala Gly Ala Gly Thr Cys Cys
        50                  55                  60
```

<210> SEQ ID NO 43
<211> LENGTH: 60
<212> TYPE: PRT
<213> ORGANISM: Mus musculus

<400> SEQUENCE: 43

```
Gly Gly Ala Ala Gly Ala Cys Thr Gly Thr Cys Ala Gly Ala Thr Cys
1               5                   10                  15

Thr Thr Gly Ala Cys Thr Gly Gly Cys Ala Cys Ala Thr Cys Thr
            20                  25                  30

Gly Thr Ala Cys Cys Ala Gly Thr Gly Gly Thr Thr Gly Thr Gly Cys
        35                  40                  45

Cys Cys Gly Gly Thr Gly Cys Ala Ala Gly Gly
        50                  55                  60

<210> SEQ ID NO 44
<211> LENGTH: 60
<212> TYPE: PRT
<213> ORGANISM: Mus musculus

<400> SEQUENCE: 44

Cys Cys Gly Gly Cys Thr Gly Cys Cys Ala Cys Thr Gly Ala Cys
1               5                   10                  15

Thr Gly Cys Thr Gly Cys Cys Ala Thr Gly Ala Gly Cys Ala Gly Thr
            20                  25                  30

Gly Thr Gly Cys Cys Gly Cys Ala Gly Gly Cys Thr Gly Cys Ala Cys
        35                  40                  45

Gly Gly Gly Cys Cys Cys Ala Ala Gly Cys Ala
        50                  55                  60

<210> SEQ ID NO 45
<211> LENGTH: 3716
<212> TYPE: DNA
<213> ORGANISM: Rattus norvegicus

<400> SEQUENCE: 45
ccggaatcgc gggcacccaa gtgtgtaccg gcacagacat gaagttgcgg ctccctgcca      60
gtcctgagac ccacctggac atgctccgcc acctgtacca gggctgtcag gtagtgcagg     120
gcaacttgga gcttacctac gtgcctgcca atgccagcct tcattcctg caggacatcc     180
aggaagttca gggttacatg ctcatcgctc acaaccaggt gaagcgcgtc ccactgcaaa     240
ggctgcgcat cgtgagaggg acccagctct tgaggacaa gtatgccctg ctgtgctag     300
acaaccgaga tcctcaggac aatgtcgccg cctccacccc aggcagaacc ccagaggggc     360
tgcgggagct gcagcttcga agtctcacag agatcctgaa ggaggagtt ttgatccgtg     420
ggaaccctca gctctgctac caggacatgg ttttgtggaa ggacgtcttc cgcaagaata     480
accaactggc tcctgtcgat atagacacca atcgttcccg ggcctgtcca ccttgtgccc     540
ccgcctgcaa agacaatcac tgttggggtg agagtccgga agactgtcag atcttgactg     600
gcaccatctg taccagtggt tgtgcccggt gcaagggccg gctgcccact gactgctgcc     660
atgagcagtg tgccgcaggc tgcacgggcc ccaagcattc tgactgcctg gcctgcctcc     720
acttcaatca tagtggtatc tgtgagctgc actgcccagc cctcgtcacc tacaacacag     780
acaccttta gtccatgcac aaccctgagg gtcgctacac ctttggtgcc agctgcgtga     840
ccacctgccc ctacaactac ctgtctacgg aagtgggatc ctgcactctg gtgtgtcccc     900
cgaataacca agaggtcaca gctgaggacg gaacacagc ttgtgagaaa tgcagcaagc     960
cctgtgctcg agtgtgctat ggtctgggca tggagcacct tcgaggggcg agggccatca    1020
ccagtgacaa tgtccaggag tttgatggct gcaagaagat cttttgggagc ctggcatttt    1080
tgccggagag ctttgatggg gacccctcct ccggcattgc tccgctgagg cctgagcagc    1140
tccaagtgtt cgaaaccctg gaggagatca caggttacct gtacatctca gcatggccag    1200
```

```
acagtctccg tgacctcagt gtcttccaga accttcgaat cattcgggga cggattctcc    1260
acgatggcgc gtactcattg acactgcaag gcctggggat ccactcgctg ggctgcgct     1320
cactgcggga gctgggcagt ggattggctc tgattcaccg caacgcccat ctctgctttg    1380
tacacactgt accttgggac cagctcttcc ggaacccaca tcaggccctg ctccacagtg    1440
ggaaccggcc ggaagaggat tgtggtctcg agggcttggt ctgtaactca ctgtgtgccc    1500
acgggcactg ctgggggcca gggcccaccc agtgtgtcaa ctgcagtcat ttccttcggg    1560
gccaggagtg tgtggaggag tgccgagtat ggaaggggct ccccggggag tatgtgagtg    1620
acaagcgctg tctgccgtgt caccccgagt gtcagcctca aaacagctca gagacctgct    1680
ttggatcgga ggctgatcag tgtgcagcct gcgcccacta caaggactcg tcctcctgtg    1740
tggctcgctg ccccagtggt gtgaaaccgg acctctccta catgcccatc tggaagtacc    1800
cggatgagga gggcatatgc cagccgtgcc ccatcaactg cacccactcc tgtgtggatc    1860
tggatgaacg aggctgccca gcagagcaga gagccagccc ggtgacattc atcattgcaa    1920
ctgtagtggg cgtcctgctg ttcctgatct tagtggtggt cgttggaatc ctaatcaaac    1980
gaaggagaca gaagatccgg aagtatacga tgcgtaggct gctgcaggaa actgagttag    2040
tggagccgct gacgcccagc ggagcaatgc ccaaccaggc tcagatgcgg atcctaaaag    2100
agacggagct aaggaaggtg aaggtgcttg gatcaggagc ttttggcact gtctacaagg    2160
gcatctggat cccagatggg gagaatgtga aaatccccgt ggctatcaag gtgttgagag    2220
aaaacacatc tcctaaagcc aacaaagaaa ttcgagatga agcgtatgtg atggctggtg    2280
tgggttctcc gtatgtgtcc cgcctcctgg gcatctgcct gacatccaca gtacagctgg    2340
tgacacagct tatgccctac ggctgccttt ggaccatgt ccgagaacac cgaggtcgcc     2400
taggctccca ggacctgctc aactggtgtg ttcagattgc caaggggatg agctacctgg    2460
aggacgtgcg gcttgtacac agggacctgg ctgcccggaa tgtgctagtc aagagtccca    2520
accacgtcaa gattacagat ttcgggctgg ctcggctgct ggacattgat gagacagagt    2580
accatgcaga tggggcaag gtgcccatca aatggatggc attggaatct attctcagac     2640
gccggttcac ccatcagagt gatgtgtgga gctatggagt gactgtgtgg gagctgatga    2700
cttttggggc caaaccttac gatggaatcc cagcccggga gatccctgat ttgctggaga    2760
agggagaacg cctacctcag cctccaatct gcaccattga tgtctacatg attatggtca    2820
aatgttggat gattgactct gaatgtcgcc cgagattccg ggagttggtg tcagaatttt    2880
cacgtatggc gagggacccc cagcgttttg tggtcatcca gaacgaggac ttgggcccat    2940
ccagccccat ggacagtacc ttctaccgtt cactgctgga agatgatgac atgggtgacc    3000
tggtagacgc tgaagagtat ctggtgcccc agcaggatt cttctccccg daccctaccc    3060
caggcactgg gagcacagcc catagaaggc accgcagctc gtccaccagg agtggaggtg    3120
gtgagctgac actgggcctg gagccctcgg aagaagggcc cccagatct ccactggctc    3180
cctcggaagg ggctggctcc gatgtgtttg atggtgacct ggcaatgggg gtaaccaaag    3240
ggctgcagag cctctctcca catgacctca gccctctaca gcggtacagc gaggacccca    3300
cattacctct gcccccgag actgatggct atgttgctcc cctggcctgc agcccccagc     3360
ccgagtatgt gaaccaatca gaggttcagc ctcagcctcc tttaacccca gagggtcctc    3420
tgcctccgtgt ccggcctgct ggtgctactc tagaaagacc caagactctc tctcctggga    3480
agaatggggt tgtcaaagac gtttttgcct tcggggtgc tgtggagaac cctgaatact    3540
```

| | |
|---|---|
| tagtaccgag agaaggcact gcctctccgc cccacccttc tcctgccttc agcccagcct | 3600 |
| ttgacaacct ctattactgg gaccagaact catcggagca ggggcctcca ccaagtaact | 3660 |
| ttgaagggac ccccactgca gagaaccctg agtacctagg cctggatgta cctgta | 3716 |

<210> SEQ ID NO 46
<211> LENGTH: 360
<212> TYPE: DNA
<213> ORGANISM: Rattus norvegicus

<400> SEQUENCE: 46

| | |
|---|---|
| cccaggcaga accccagagg ggctgcggga gctgcagctt cgaagtctca cagagatcct | 60 |
| gaagggagga gttttgatcc gtgggaaccc tcagctctgc taccaggaca tggttttgtg | 120 |
| gaaggacgtc ttccgcaaga taaccaact ggctcctgtc gatatagaca ccaatcgttc | 180 |
| ccgggcctgt ccaccttgtg cccccgcctg caaagacaat cactgttggg gtgagagtcc | 240 |
| ggaagactgt cagatcttga ctggcaccat ctgtaccagt ggttgtgccc ggtgcaaggg | 300 |
| ccggctgccc actgactgct gccatgagca gtgtgccgca ggctgcacgg ccccaagca | 360 |

<210> SEQ ID NO 47
<211> LENGTH: 618
<212> TYPE: DNA
<213> ORGANISM: Rattus norvegicus

<400> SEQUENCE: 47

| | |
|---|---|
| ggtcacagct gaggacggaa cacagcgttg tgagaaatgc agcaagccct gtgctcgagt | 60 |
| gtgctatggt ctgggcatgg agcaccttcg aggggcgagg gccatcacca gtgacaatgt | 120 |
| ccaggagttt gatggctgca agaagatctt tgggagcctg gcattttgc cggagagctt | 180 |
| tgatggggac ccctcctccg gcattgctcc gctgaggcct gagcagctcc aagtgttcga | 240 |
| aaccctggag gagatcacag gttacctgta catctcagca tggccagaca gtctccgtga | 300 |
| cctcagtgtc ttccagaacc ttcgaatcat tcggggacgg attctccacg atggcgcgta | 360 |
| ctcattgaca ctgcaaggcc tggggatcca ctcgctgggg ctgcgctcac tgcgggagct | 420 |
| gggcagtgga ttggctctga ttcaccgcaa cgcccatctc tgctttgtac acactgtacc | 480 |
| ttgggaccag ctcttccgga acccacatca ggccctgctc cacagtggga accggccgga | 540 |
| agaggattgt ggtctcgagg gcttggtctg taactcactg tgtgcccacg gcactgctg | 600 |
| ggggccaggg cccaccca | 618 |

<210> SEQ ID NO 48
<211> LENGTH: 929
<212> TYPE: DNA
<213> ORGANISM: Rattus norvegicus

<400> SEQUENCE: 48

| | |
|---|---|
| cgcccagcgg agcaatgccc aaccaggctc agatgcggat cctaaaagag acggagctaa | 60 |
| ggaaggtgaa ggtgcttgga tcaggagctt ttggcactgt ctacaagggc atctggatcc | 120 |
| cagatgggga gaatgtgaaa atccccgtgg ctatcaaggt gttgagagaa aacacatctc | 180 |
| ctaaagccaa caaagaaatt ctagatgaag cgtatgtgat ggctggtgtg ggttctccgt | 240 |
| atgtgtcccg cctcctgggc atctgcctga catccacagt acagctggtg acacagctta | 300 |
| tgccctacgg ctgccttctg gaccatgtcc gagaacaccg aggtcgccta ggctcccagg | 360 |
| acctgctcaa ctggtgtgtt cagattgcca aggggatgag ctacctggag gacgtgcggc | 420 |
| ttgtacacag ggacctggct gcccggaatg tgctagtcaa gagtcccaac cacgtcaaga | 480 |

| | | |
|---|---|---|
| ttacagattt cgggctggct cggctgctgg acattgatga gacagagtac catgcagatg | 540 |
| ggggcaaggt gcccatcaaa tggatggcat tggaatctat tctcagacgc cggttcaccc | 600 |
| atcagagtga tgtgtggagc tatggagtga ctgtgtggga gctgatgact tttggggcca | 660 |
| aaccttacga tggaatccca gcccgggaga tccctgattt gctggagaag ggagaacgcc | 720 |
| tacctcagcc tccaatctgc accattgatg tctacatgat tatggtcaaa tgttggatga | 780 |
| ttgactctga atgtcgcccg agattccggg agttggtgtc agaattttca cgtatggcga | 840 |
| gggaccccca gcgttttgtg gtcatccaga acgaggactt gggcccatcc agccccatgg | 900 |
| acagtacctt ctaccgttca ctgctggaa | 929 |

<210> SEQ ID NO 49
<211> LENGTH: 3798
<212> TYPE: DNA
<213> ORGANISM: Homo sapiens

<400> SEQUENCE: 49

| | | |
|---|---|---|
| atggagctgg cggccttgtg ccgctggggg ctcctcctcg ccctcttgcc ccccggagcc | 60 |
| gcgagcaccc aagtgtgcac cggcacagac atgaagctgc ggctccctgc cagtcccgag | 120 |
| acccacctgg acatgctccg ccacctctac cagggctgcc aggtggtgca gggaaacctg | 180 |
| gaactcacct acctgcccac caatgccagc ctgtccttcc tgcaggatat ccaggaggtg | 240 |
| cagggctacg tgctcatcgc tcacaaccaa gtgaggcagg tcccactgca gaggctgcgg | 300 |
| attgtgcgag caccccagct cttttgaggac aactatgccc tggccgtgct agacaatgga | 360 |
| gacccgctga acaataccac ccctgtcaca ggggcctccc caggaggcct gcgggagctg | 420 |
| cagcttcgaa gcctcacaga gatcttgaaa ggagggtct tgatccagcg gaaccccag | 480 |
| ctctgctacc aggacacgat tttgtggaag gacatcttcc acaagaacaa ccagctggct | 540 |
| ctcacactga tagacaccaa ccgctctcgg gcctgccacc cctgttctcc gatgtgtaag | 600 |
| ggctcccgct gctggggaga gagttctgag gattgtcaga gctgacgcg cactgtctgt | 660 |
| gccggtggct gtgcccgctg caaggggcca ctgcccactg actgctgcca tgagcagtgt | 720 |
| gctgccggct gcacgggccc caagcactct gactgcctgg cctgcctcca cttcaaccac | 780 |
| agtggcatct gtgagctgca ctgcccagcc ctggtcacct acaacacaga cacgtttgag | 840 |
| tccatgccca atcccgaggg ccggtataca ttcggcgcca gctgtgtgac tgcctgtccc | 900 |
| tacaactacc tttctacgga cgtgggatcc tgcaccctcg tctgccccct gcacaaccaa | 960 |
| gaggtgacag cagaggatgg aacacagcgg tgtgagaagt gcagcaagcc ctgtgcccga | 1020 |
| gtgtgctatg gtctgggcat ggagcacttg cgagaggtga gggcagttac cagtgccaat | 1080 |
| atccaggagt ttgctggctg caagaagatc tttgggagcc tggcatttct gccggagagc | 1140 |
| tttgatgggg acccagcctc caacactgcc ccgctccagc cagagcagct ccaagtgttt | 1200 |
| gagactctgg aagagatcac aggttaccta tacatctcag catggccgga cagcctgcct | 1260 |
| gacctcagcg tcttccagaa cctgcaagta atccggggac gaattctgca caatggcgcc | 1320 |
| tactcgctga ccctgcaagg gctgggcatc agctggctgg gctgcgctc actgagggaa | 1380 |
| ctgggcagtg gactggccct catccaccat aacacccacc tctgcttcgt gcacacggtg | 1440 |
| ccctgggacc agctctttcg gaacccgcac caagctctgc tccacactgc caaccggcca | 1500 |
| gaggacgagt gtgtgggcga gggcctggcc tgccaccagc tgtgcgcccg agggcactgc | 1560 |
| tggggtccag ggcccaccca gtgtgtcaac tgcagccagt tccttcgggg ccaggagtgc | 1620 |

```
gtggaggaat gccgagtact gcaggggctc cccagggagt atgtgaatgc caggcactgt    1680
ttgccgtgcc accctgagtg tcagccccag aatggctcag tgacctgttt tggaccggag    1740
gctgaccagt gtgtggcctg tgcccactat aaggaccctc ccttctgcgt ggcccgctgc    1800
cccagcggtg tgaaacctga cctctcctac atgcccatct ggaagtttcc agatgaggag    1860
ggcgcatgcc agccttgccc catcaactgc acccactcct gtgtggacct ggatgacaag    1920
ggctgccccg ccgagcagag agccagccct ctgacgtcca tcgtctctgc ggtggttggc    1980
attctgctgg tcgtggtctt gggggtggtc tttgggatcc tcatcaagcg acggcagcag    2040
aagatccgga agtacacgat gcggagactg ctgcaggaaa cggagctggt ggagccgctg    2100
acacctagcg gagcgatgcc caaccaggcg cagatgcgga tcctgaaaga cggagctg     2160
aggaaggtga aggtgcttgg atctggcgct tttggcacag tctacaaggg catctggatc    2220
cctgatgggg agaatgtgaa aattccagtg gccatcaaag tgttgaggga aaacacatcc    2280
cccaaagcca caaagaaat cttagacgaa gcatacgtga tggctggtgt gggctcccca    2340
tatgtctccc gccttctggg catctgcctg acatccacgg tgcagctggt gacacagctt    2400
atgccctatg gctgcctctt agaccatgtc cgggaaaacc gcggacgcct gggctcccag    2460
gacctgctga actggtgtat gcagattgcc aaggggatga gctacctgga ggatgtgcgg    2520
ctcgtacaca gggacttggc cgctcggaac gtgctggtca agagtcccaa ccatgtcaaa    2580
attacagact tcgggctggc tcggctgctg gacattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccgggag atccctgacc tgctggaaaa gggggagcgg    2820
ctgccccagc cccccatctg caccattgat gtctacatga tcatggtcaa atgttggatg    2880
attgactctg aatgtcggcc aagattccgg gagttggtgt ctgaattctc ccgcatggcc    2940
agggaccccc agcgctttgt ggtcatccag aatgaggact gggcccagc cagtcccttg    3000
gacagcacct tctaccgctc actgctggag gacgatgaca tgggggacct ggtggatgct    3060
gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggaccccac agtacccctg    3360
ccctctgaga ctgatggcta cgttgccccc ctgacctgca gccccagcc tgaatatgtg    3420
aaccagccag atgttcggcc ccagcccccct tcgccccgag agggccctct gcctgctgcc    3480
cgacctgctg gtgccactct ggaaagggcc aagactctct cccagggaa gaatgggtc     3540
gtcaaagacg ttttgccctt tggggtgcc gtggagaacc ccgagtactt gacaccccag    3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtgaac cagaaggcca    3780
agtccgcaga agccctga                                                3798
```

<210> SEQ ID NO 50
<211> LENGTH: 393
<212> TYPE: DNA
<213> ORGANISM: Homo sapiens

<400> SEQUENCE: 50

```
gagacccacc tggacatgct ccgccacctc taccagggct gccaggtggt gcagggaaac      60
ctggaactca cctacctgcc caccaatgcc agcctgtcct tcctgcagga tatccaggag     120
gtgcagggct acgtgctcat cgctcacaac caagtgaggc aggtcccact gcagaggctg     180
cggattgtgc gaggcaccca gctctttgag acaactatg ccctggccgt gctagacaat      240
ggagacccgc tgaacaatac caccctgtc acagggcct ccccaggagg cctgcgggag       300
ctgcagcttc gaagcctcac agagatcttg aaaggagggg tcttgatcca gcggaacccc     360
cagctctgct accaggacac gattttgtgg aag                                 393
```

<210> SEQ ID NO 51
<211> LENGTH: 477
<212> TYPE: PRT
<213> ORGANISM: Homo sapiens

<400> SEQUENCE: 51

```
Ala Ala Thr Ala Thr Cys Cys Ala Gly Gly Ala Gly Thr Thr Thr Gly
  1               5                   10                  15

Cys Thr Gly Gly Cys Thr Gly Cys Ala Ala Gly Ala Gly Ala Thr
             20                  25                  30

Cys Thr Thr Thr Gly Gly Gly Ala Gly Cys Cys Thr Gly Gly Cys Ala
         35                  40                  45

Thr Thr Thr Cys Thr Gly Cys Cys Gly Gly Ala Gly Ala Gly Cys Thr
     50                  55                  60

Thr Thr Gly Ala Thr Gly Gly Gly Ala Cys Cys Ala Gly Cys
 65                  70                  75                  80

Cys Thr Cys Cys Ala Ala Cys Ala Cys Thr Gly Cys Cys Cys Gly
             85                  90                  95

Cys Thr Cys Cys Ala Gly Cys Ala Gly Ala Gly Cys Ala Gly Cys
            100                 105                 110

Thr Cys Cys Ala Ala Gly Thr Gly Thr Thr Gly Ala Gly Ala Cys
         115                 120                 125

Thr Cys Thr Gly Gly Ala Ala Gly Ala Gly Ala Thr Cys Ala Cys Ala
         130                 135                 140

Gly Gly Thr Thr Ala Cys Cys Thr Ala Thr Ala Cys Ala Thr Cys Thr
145                 150                 155                 160

Cys Ala Gly Cys Ala Thr Gly Gly Cys Cys Gly Gly Ala Cys Ala Gly
                165                 170                 175

Cys Cys Thr Gly Cys Cys Thr Gly Ala Cys Cys Thr Cys Ala Gly Cys
            180                 185                 190

Gly Thr Cys Thr Thr Cys Cys Ala Gly Ala Ala Cys Cys Thr Gly Cys
        195                 200                 205

Ala Ala Gly Thr Ala Ala Thr Cys Cys Gly Gly Gly Ala Cys Gly
    210                 215                 220

Ala Ala Thr Thr Cys Thr Gly Cys Ala Cys Ala Ala Thr Gly Gly Cys
225                 230                 235                 240

Gly Cys Cys Thr Ala Cys Thr Gly Cys Thr Gly Ala Cys Cys Cys
                245                 250                 255

Thr Gly Cys Ala Ala Gly Gly Gly Cys Thr Gly Gly Gly Cys Ala Thr
            260                 265                 270

Cys Ala Gly Cys Thr Gly Gly Cys Thr Gly Gly Gly Cys Thr Gly
        275                 280                 285
```

Cys Gly Cys Thr Cys Ala Cys Thr Gly Ala Gly Gly Ala Ala Cys
                290                 295                 300

Thr Gly Gly Gly Cys Ala Gly Thr Gly Gly Ala Cys Thr Gly Gly Cys
305                 310                 315                 320

Cys Cys Thr Cys Ala Thr Cys Cys Ala Cys Cys Ala Thr Ala Ala Cys
                325                 330                 335

Ala Cys Cys Cys Ala Cys Cys Thr Cys Thr Gly Cys Thr Thr Cys Gly
                340                 345                 350

Thr Gly Cys Ala Cys Ala Cys Gly Gly Thr Gly Cys Cys Cys Thr Gly
                355                 360                 365

Gly Gly Ala Cys Cys Ala Gly Cys Thr Cys Thr Thr Thr Cys Gly Gly
            370                 375                 380

Ala Ala Cys Cys Cys Gly Cys Ala Cys Cys Ala Ala Gly Cys Thr Cys
385                 390                 395                 400

Thr Gly Cys Thr Cys Cys Ala Cys Ala Cys Thr Gly Cys Cys Ala Ala
                405                 410                 415

Cys Cys Gly Gly Cys Cys Ala Gly Ala Gly Gly Ala Cys Gly Ala Gly
                420                 425                 430

Thr Gly Thr Gly Thr Gly Gly Gly Cys Gly Ala Gly Gly Cys Cys Cys
                435                 440                 445

Thr Gly Gly Cys Cys Thr Gly Cys Cys Ala Cys Cys Ala Gly Cys Thr
450                 455                 460

Gly Thr Gly Cys Gly Cys Cys Gly Ala Gly Gly Gly
465                 470                 475

<210> SEQ ID NO 52
<211> LENGTH: 391
<212> TYPE: DNA
<213> ORGANISM: Homo sapiens

<400> SEQUENCE: 52
cagcagaaga tccggaagta cacgatgcgg agactgctgc aggaaacgga gctggtggag    60
ccgctgacac ctagcggagc gatgcccaac caggcgcaga tgcggatcct gaaagagacg   120
gagctgagga aggtgaaggt gcttggatct ggcgcttttg cacagtctca aagggcatc    180 tggatccctg atgggaagaa tgtgaaaatt ccagtggcca tcaaagtgtt gagggaaaac   240
acatccccca agccaacaa agaaatctta gacgaagcat acgtgatggc tggtgtgggc    300
tccccatatg tctcccgcct tctgggcatc tgcctgacat ccacggtgca gctggtgaca   360
cagcttatgc cctatggctg cctcttagac t                                  391

<210> SEQ ID NO 53
<211> LENGTH: 7075
<212> TYPE: DNA
<213> ORGANISM: Artificial Sequence
<220> FEATURE:
<223> OTHER INFORMATION: Plasmid sequence of pAdv164

<400> SEQUENCE: 53
cggagtgtat actggcttac tatgttggca ctgatgaggg tgtcagtgaa gtgcttcatg    60
tggcaggaga aaaaggctg caccggtgcg tcagcagaat atgtgataca ggatatattc   120
cgcttcctcg ctcactgact cgctacgctc ggtcgttcga ctgcggcgag cggaaatggc   180
ttacgaacgg ggcggagatt tcctggaaga tgccaggaag atacttaaca gggaagtgag   240
agggccgcgg caaagccgtt tttccatagg ctccgccccc ctgacaagca tcacgaaatc   300
tgacgctcaa atcagtggtg gcgaaacccg acaggactat aaagatacca ggcgtttccc   360

```
cctggcggct ccctcgtgcg ctctcctgtt cctgcctttc ggtttaccgg tgtcattccg      420
ctgttatggc cgcgtttgtc tcattccacg cctgacactc agttccgggt aggcagttcg      480
ctccaagctg gactgtatgc acgaaccccc cgttcagtcc gaccgctgcg ccttatccgg      540
taactatcgt cttgagtcca acccggaaag acatgcaaaa gcaccactgg cagcagccac      600
tggtaattga tttagaggag ttagtcttga agtcatgcgc cggttaaggc taaactgaaa      660
ggacaagttt tggtgactgc gctcctccaa gccagttacc tcggttcaaa gagttggtag      720
ctcagagaac cttcgaaaaa ccgccctgca aggcggtttt ttcgttttca gagcaagaga      780
ttacgcgcag accaaaacga tctcaagaag atcatcttat taatcagata aaatatttct      840
agccctcctt tgattagtat attcctatct taaagttact tttatgtgga ggcattaaca      900
tttgttaatg acgtcaaaag datagcaaga ctagaataaa gctataaagc aagcatataa      960
tattgcgttt catctttaga agcgaatttc gccaatatta taattatcaa agagagggg      1020 tggcaaacgg tatttggcat tattaggtta aaaaatgtag aaggagagtg aaacccatga      1080
aaaaaataat gctagttttt attacactta tattagttag tctaccaatt gcgcaacaaa      1140
ctgaagcaaa ggatgcatct gcattcaata agaaaattc aatttcatcc atggcaccac      1200
cagcatctcc gcctgcaagt cctaagacgc caatcgaaaa gaaacacgcg gatgaaatcg      1260
ataagtatat acaaggattg gattacaata aaaacaatgt attagtatac cacggagatg      1320
cagtgacaaa tgtgccgcca agaaaaggtt acaaagatgg aaatgaatat attgttgtgg      1380 agaaaagaa gaaatccatc aatcaaaata atgcagacat tcaagttgtg aatgcaattt      1440
cgagcctaac ctatccaggt gctctcgtaa aagcgaattc ggaattagta gaaaatcaac      1500
cagatgttct ccctgtaaaa cgtgattcat taacactcag cattgatttg ccaggtatga      1560
ctaatcaaga caataaaata gttgtaaaaa atgccactaa atcaaacgtt aacaacgcag      1620
taaatacatt agtggaaaga tggaatgaaa aatatgctca agcttatcca aatgtaagtg      1680
caaaaattga ttatgatgac gaaatggctt acagtgaatc acaattaatt gcgaaatttg      1740
gtacagcatt taaagctgta aataatagct tgaatgtaaa cttcggcgca atcagtgaag      1800
ggaaaatgca agaagaagtc attagttta aacaaattta ctataacgtg aatgttaatg      1860
aacctacaag accttccaga ttttcggca agctgttac taaagagcag ttgcaagcgc      1920
ttggagtgaa tgcagaaaat cctcctgcat atatctcaag tgtggcgtat ggccgtcaag      1980
tttatttgaa attatcaact aattcccata gtactaaagt aaaagctgct tttgatgctg      2040
ccgtaagcgg aaaatctgtc tcaggtgatg tagaactaac aaatatcatc aaaaattctt      2100
ccttcaaagc cgtaatttac ggaggttccg caaagatga agttcaaatc atcgacggca      2160
acctcggaga cttacgcgat attttgaaaa aaggcgctac ttttaatcga gaacaccag      2220 gagttcccat tgcttataca acaaacttcc taaagacaa tgaattagct gttattaaaa      2280
acaactcaga atatatgaa acaacttcaa agcttatac agatggaaaa attaacatcg      2340
atcactctgg aggatacgtt gctcaattca acatttcttg ggatgaagta aattatgatc      2400
tcgagaccca cctggacatg ctccgccacc tctaccaggg ctgccaggtg gtgcagggaa      2460
acctggaact cacctacctg cccaccaatg ccagcctgtc cttcctgcag gatatccagg      2520
aggtgcaggg ctacgtgctc atcgctcaca ccaagtgag gcaggtccca ctgcagaggc      2580
tgcggattgt gcgaggcacc cagctctttg aggacaacta tgccctggcc gtgctagaca      2640
atggagaccc gctgaacaat accaccccctg tcacaggggc ctccccagga ggcctgcggg      2700
```

```
agctgcagct tcgaagcctc acagagatct tgaaaggagg ggtcttgatc cagcggaacc    2760
cccagctctg ctaccaggac acgattttgt ggaagaatat ccaggagttt gctggctgca    2820
agaagatctt tgggagcctg gcatttctgc cggagagctt tgatggggac ccagcctcca    2880
acactgcccc gctccagcca gagcagctcc aagtgtttga gactctggaa gagatcacag    2940
gttacctata catctcagca tggccggaca gcctgcctga cctcagcgtc ttccagaacc    3000
tgcaagtaat ccggggacga attctgcaca atggcgccta ctcgctgacc ctgcaagggc    3060
tgggcatcag ctggctgggg ctgcgctcac tgagggaact gggcagtgga ctggccctca    3120
tccaccataa cacccacctc tgcttcgtgc acacggtgcc ctgggaccag ctctttcgga    3180
acccgcacca agctctgctc cacactgcca accggccaga ggacgagtgt gtgggcgagg    3240
gcctggcctg ccaccagctg tgcgcccgag ggcagcagaa gatccggaag tacacgatgc    3300
ggagactgct gcaggaaacg gagctggtgg agccgctgac acctagcgga gcgatgccca    3360
accaggcgca gatgcggatc ctgaaagaga cggagctgag gaaggtgaag gtgcttggat    3420
ctggcgcttt tggcacagtc tacaagggca tctggatccc tgatggggag aatgtgaaaa    3480
ttccagtggc catcaaagtg ttgagggaaa acacatcccc caaagccaac aaagaaatct    3540
tagacgaagc atacgtgatg gctggtgtgg gctccccata tgtctcccgc cttctgggca    3600
tctgcctgac atccacggtg cagctggtga cacagcttat gccctatggc tgcctcttag    3660
actaatctag acccgggcca ctaactcaac gctagtagtg gatttaatcc caaatgagcc    3720
aacagaacca gaaccagaaa cagaacaagt aacattggag ttagaaatgg aagaagaaaa    3780
aagcaatgat ttcgtgtgaa taatgcacga aatcattgct tattttttta aaaagcgata    3840
tactagatat aacgaaacaa cgaactgaat aaagaataca aaaaaagagc cacgaccagt    3900
taaagcctga gaaactttaa ctgcgagcct taattgatta ccaccaatca attaaagaag    3960
tcgagaccca aaatttggta aagtatttaa ttactttatt aatcagatac ttaaatatct    4020
gtaaacccat tatatcgggt ttttgagggg atttcaagtc tttaagaaga taccaggcaa    4080
tcaattaaga aaaacttagt tgattgcctt ttttgttgtg attcaacttt gatcgtagct    4140
tctaactaat taattttcgt aagaaaggag aacagctgaa tgaatatccc ttttgttgta    4200
gaaactgtgc ttcatgacgg cttgttaaag tacaaattta aaaatagtaa aattcgctca    4260
atcactacca agccaggtaa aagtaaaggg gctattttg cgtatcgctc aaaaaaaagc    4320
atgattggcg gacgtggcgt tgttctgact tccgaagaag cgattcacga aaatcaagat    4380
acatttacgc attggacacc aaacgtttat cgttatggta cgtatgcaga cgaaaaccgt    4440
tcatacacta aaggacattc tgaaaacaat ttaagacaaa tcaataccct tctttattgat    4500 tttgatattc acacggaaaa agaaactatt tcagcaagcg atattttaac aacagctatt    4560
gatttaggtt ttatgcctac gttaattatc aaatctgata aaggttatca agcatatttt    4620
gttttagaaa cgccagtcta tgtgacttca aaatcagaat ttaaatctgt caaagcagcc    4680
aaaataatct cgcaaaatat ccgagaatat tttggaaagt ctttgccagt tgatctaacg    4740
tgcaatcatt ttgggattgc tcgtataccg agaacggaca atgtagaatt ttttgatccc    4800
aattaccgtt attcttttcaa agaatggcaa gattggtctt tcaaacaaac agataataag    4860
ggctttactc gttcaagtct aacggtttta agcggtacag aaggcaaaaa acaagtagat    4920
gaaccctggt ttaatctctt attgcacgaa acgaattttt caggagaaaa gggtttagta    4980
gggcgcaata gcgttatgtt taccctctct ttagcctact ttagttcagg ctattcaatc    5040
gaaacgtgcg aatataatat gtttgagttt aataatcgat tagatcaacc cttagaagaa    5100
```

-continued

```
aaagaagtaa tcaaaattgt tagaagtgcc tattcagaaa actatcaagg ggctaatagg    5160
gaatacatta ccattctttg caaagcttgg gtatcaagtg atttaaccag taaagattta    5220
tttgtccgtc aagggtggtt taaattcaag aaaaaaagaa gcgaacgtca acgtgttcat    5280
ttgtcagaat ggaaagaaga tttaatggct tatattagcg aaaaaagcga tgtatacaag    5340
ccttatttag cgacgaccaa aaaagagatt agagaagtgc taggcattcc tgaacggaca    5400
ttagataaat tgctgaaggt actgaaggcg aatcaggaaa ttttctttaa gattaaacca    5460
ggaagaaatg gtggcattca acttgctagt gttaaatcat tgttgctatc gatcattaaa    5520
ttaaaaaaag aagaacgaga aagctatata aaggcgctga cagcttcgtt taatttagaa    5580
cgtacattta ttcaagaaac tctaaacaaa ttggcagaac gccccaaaac ggacccacaa    5640
ctcgatttgt ttagctacga tacaggctga aaataaaacc cgcactatgc cattacattt    5700
atatctatga tacgtgtttg tttttctttg ctggctagct taattgctta tatttacctg    5760
caataaagga tttcttactt ccattatact cccatttccc aaaaacatac ggggaacacg    5820
ggaacttatt gtacaggcca cctcatagtt aatggtttcg agccttcctg caatctcatc    5880
catgaaaata tattcatccc cctgccggcc tattaatgtg acttttgtgc ccggcggata    5940
ttcctgatcc agctccacca taaattggtc catgcaaatt cggccggcaa ttttcaggcg    6000
ttttcccttc acaaggatgt cggtcccttt caattttcgg agccagccgt ccgcatagcc    6060
tacaggcacc gtcccgatcc atgtgtcttt ttccgctgtg tactcggctc cgtagctgac    6120
gctctcgcct tttctgatca gtttgacatg tgacagtgtc gaatgcaggg taaatgccgg    6180
acgcagctga aacggtatct cgtccgacat gtcagcagac gggcgaaggc catacatgcc    6240
gatgccgaat ctgactgcat taaaaaagcc ttttttcagc cggagtccag cggcgctgtt    6300
cgcgcagtgg accattagat tctttaacgg cagcggagca atcagctctt taaagcgctc    6360
aaactgcatt aagaaatagc ctctttcttt ttcatccgct gtcgcaaaat gggtaaatac    6420
cccttttgcac tttaaacgag ggttgcggtc aagaattgcc atcacgttct gaacttcttc    6480
ctctgttttt acaccaagtc tgttcatccc cgtatcgacc ttcagatgaa atgaagaga    6540
acctttttc gtgtggcggg ctgcctcctg aagccattca acagaataac ctgttaaggt    6600
cacgtcatac tcagcagcga ttgccacata ctccggggga accgcgccaa gcaccaatat    6660
aggcgccttc aatcccttttt tgcgcagtga atcgcttca tccaaaatgg ccacggccaa    6720
gcatgaagca cctgcgtcaa gagcagcctt tgctgtttct gcatcaccat gcccgtaggc    6780
gtttgctttc acaactgcca tcaagtggac atgttcaccg atatgttttt tcatattgct    6840
gacattttcc tttatcgcgg acaagtcaat ttccgcccac gtatctctgt aaaaaggttt    6900
tgtgctcatg gaaaactcct ctcttttttc agaaaatccc agtacgtaat taagtatttg    6960
agaattaatt ttatattgat taatactaag tttacccagt tttcacctaa aaaacaaatg    7020
atgagataat agctccaaag gctaaagagg actataccaa ctatttgtta attaa         7075
```

<210> SEQ ID NO 54
<211> LENGTH: 921
<212> TYPE: DNA
<213> ORGANISM: Homo sapiens

<400> SEQUENCE: 54

```
gccgcgagca cccaagtgtg caccggcaca gacatgaagc tgcggctccc tgccagtccc      60
gagacccacc tggacatgct ccgccacctc taccagggct gccaggtggt gcagggaaac     120
```

| | |
|---|---|
| ctggaactca cctacctgcc caccaatgcc agcctgtcct tcctgcagga tatccaggag | 180 |
| gtgcagggct acgtgctcat cgctcacaac caagtgaggc aggtcccact gcagaggctg | 240 |
| cggattgtgc gaggcaccca gctctttgag acaactatg ccctggccgt gctagacaat | 300 |
| ggagacccgc tgaacaatac caccctgtc acagggcct ccccaggagg cctgcgggag | 360 |
| ctgcagcttc gaagcctcac agagatcttg aaaggagggg tcttgatcca gcggaacccc | 420 |
| cagctctgct accaggacac gattttgtgg aaggacatct tccacaagaa caaccagctg | 480 |
| gctctcacac tgatagacac caaccgctct cgggcctgcc accctgttc tccgatgtgt | 540 |
| aagggctccc gctgctgggg agagagttct gaggattgtc agagcctgac gcgcactgtc | 600 |
| tgtgccggtg gctgtgcccg ctgcaagggg ccactgccca ctgactgctg ccatgagcag | 660 |
| tgtgctgccg gctgcacggg ccccaagcac tctgactgcc tggcctgcct ccacttcaac | 720 |
| cacagtggca tctgtgagct gcactgccca gccctggtca cctacaacac agacacgttt | 780 |
| gagtccatgc caatcccga gggcggtat acattcggcg ccagctgtgt gactgcctgt | 840 |
| ccctacaact acctttctac ggacgtggga tcctgcaccc tcgtctgccc cctgcacaac | 900 |
| caagaggtga cagcagagga t | 921 |

<210> SEQ ID NO 55
<211> LENGTH: 597
<212> TYPE: DNA
<213> ORGANISM: Homo sapiens

<400> SEQUENCE: 55

| | |
|---|---|
| tacctttcta cggacgtggg atcctgcacc ctcgtctgcc cctgcacaa ccaagaggtg | 60 |
| acagcagagg atggaacaca gcggtgtgag aagtgcagca gccctgtgc ccgagtgtgc | 120 |
| tatggtctgg gcatggagca cttgcgagag gtgagggcag ttaccagtgc caatatccag | 180 |
| gagtttgctg gctgcaagaa gatctttggg agcctggcat ttctgccgga gagctttgat | 240 |
| ggggacccag cctccaacac tgccccgctc cagccagagc agctccaagt gtttgagact | 300 |
| ctggaagaga tcacaggtta cctatacatc tcagcatggc cggacagcct gcctgacctc | 360 |
| agcgtcttcc agaacctgca gtaatccgg ggacgaattc tgcacaatgg cgcctactcg | 420 |
| ctgaccctgc aagggctggg catcagctgg ctggggctgc gctcactgag ggaactgggc | 480 |
| agtggactgg ccctcatcca ccataacacc cacctctgct tcgtgcacac ggtgccctgg | 540 |
| gaccagctct ttcggaaccc gcaccaagct ctgctccaca ctgccaaccg gccagag | 597 |

<210> SEQ ID NO 56
<211> LENGTH: 1209
<212> TYPE: DNA
<213> ORGANISM: Homo sapiens

<400> SEQUENCE: 56

| | |
|---|---|
| cagcagaaga tccggaagta cacgatgcgg agactgctgc aggaaacgga gctggtggag | 60 |
| ccgctgacac ctagcggagc gatgcccaac caggcgcaga tgcggatcct gaaagagacg | 120 |
| gagctgagga aggtgaaggt gcttggatct ggcgcttttg cacagtcta caagggcatc | 180 |
| tggatccctg atgggagaa tgtgaaaatt ccagtggcca tcaaagtgtt gagggaaaac | 240 |
| acatccccca agccaacaa agaaatctta gacgaagcat acgtgatggc tggtgtgggc | 300 |
| tccccatatg tctcccgcct tctgggcatc tgcctgacat ccacggtgca gctggtgaca | 360 |
| cagcttatgc cctatggctg cctcttagac catgtccggg aaaaccgcgg acgcctgggc | 420 |
| tcccaggacc tgctgaactg gtgtatgcag attgccaagg ggatgagcta cctggaggat | 480 |

```
gtgcggctcg tacacaggga cttggccgct cggaacgtgc tggtcaagag tcccaaccat    540
gtcaaaatta cagacttcgg gctggctcgg ctgctggaca ttgacgagac agagtaccat    600
gcagatgggg gcaaggtgcc catcaagtgg atggcgctgg agtccattct ccgccggcgg    660
ttcacccacc agagtgatgt gtggagttat ggtgtgactg tgtgggagct gatgactttt    720
ggggccaaac cttacgatgg gatcccagcc cgggagatcc ctgacctgct ggaaaagggg    780
gagcggctgc cccagccccc catctgcacc attgatgtct acatgatcat ggtcaaatgt    840
tggatgattg actctgaatg tcggccaaga ttccgggagt tggtgtctga attctcccgc    900
atggccaggg accccagcg ctttgtggtc atccagaatg aggacttggg cccagccagt    960
cccttggaca gcaccttcta ccgctcactg ctggaggacg atgacatggg ggacctggtg   1020
gatgctgagg agtatctggt accccagcag ggcttcttct gtccagaccc tgccccgggc   1080
gctgggggca tggtccacca caggcaccgc agctcatcta ccaggagtgg cggtggggac   1140
ctgacactag ggctggagcc ctctgaagag gaggccccca ggtctccact ggcaccctcc   1200
gaaggggct                                                            1209

<210> SEQ ID NO 57
<211> LENGTH: 28
<212> TYPE: DNA
<213> ORGANISM: Artificial Sequence
<220> FEATURE:
<223> OTHER INFORMATION: Her-2-Chimera (F)

<400> SEQUENCE: 57
tgatctcgag acccacctgg acatgctc                                        28

<210> SEQ ID NO 58
<211> LENGTH: 49
<212> TYPE: DNA
<213> ORGANISM: Artificial Sequence
<220> FEATURE:
<223> OTHER INFORMATION: HerEC1-EC2F (Junction)

<400> SEQUENCE: 58
ctaccaggac acgattttgt ggaagaatat ccaggagttt gctggctgc                 49

<210> SEQ ID NO 59
<211> LENGTH: 49
<212> TYPE: DNA
<213> ORGANISM: Artificial Sequence
<220> FEATURE:
<223> OTHER INFORMATION: HerEC1-EC2R (Junction)

<400> SEQUENCE: 59
gcagccagca aactcctgga tattcttcca caaaatcgtg tcctggtag                 49

<210> SEQ ID NO 60
<211> LENGTH: 50
<212> TYPE: DNA
<213> ORGANISM: Artificial Sequence
<220> FEATURE:
<223> OTHER INFORMATION: HerEC2-ICIF (Junction)

<400> SEQUENCE: 60
ctgccaccag ctgtgcgccc gagggcagca gaagatccgg aagtacacga                50

<210> SEQ ID NO 61
<211> LENGTH: 50
<212> TYPE: DNA
```

<213> ORGANISM: Artificial Sequence
<220> FEATURE:
<223> OTHER INFORMATION: HerEC2-ICIR (Junction)

<400> SEQUENCE: 61
tcgtgtactt ccggatcttc tgctgccctc gggcgcacag ctggtggcag            50

<210> SEQ ID NO 62
<211> LENGTH: 39
<212> TYPE: DNA
<213> ORGANISM: Artificial Sequence
<220> FEATURE:
<223> OTHER INFORMATION: Her-2-Chimera (R)

<400> SEQUENCE: 62
gtggcccggg tctagattag tctaagaggc agccatagg                        39

<210> SEQ ID NO 63
<211> LENGTH: 28
<212> TYPE: DNA
<213> ORGANISM: Artificial Sequence
<220> FEATURE:
<223> OTHER INFORMATION: Her-2-EC1(F)

<400> SEQUENCE: 63
ccgcctcgag gccgcgagca cccaagtg                                    28

<210> SEQ ID NO 64
<211> LENGTH: 31
<212> TYPE: DNA
<213> ORGANISM: Artificial Sequence
<220> FEATURE:
<223> OTHER INFORMATION: Her-2-EC1(R)

<400> SEQUENCE: 64
cgcgactagt ttaatcctct gctgtcacct c                                31

<210> SEQ ID NO 65
<211> LENGTH: 28
<212> TYPE: DNA
<213> ORGANISM: Artificial Sequence
<220> FEATURE:
<223> OTHER INFORMATION: Her-2-EC2(F)

<400> SEQUENCE: 65
ccgcctcgag tacctttcta cggacgtg                                    28

<210> SEQ ID NO 66
<211> LENGTH: 30
<212> TYPE: DNA
<213> ORGANISM: Artificial Sequence
<220> FEATURE:
<223> OTHER INFORMATION: Her- 2- EC2(R)

<400> SEQUENCE: 66
cgcgactagt ttactctggc cggttggcag                                  30

<210> SEQ ID NO 67
<211> LENGTH: 31
<212> TYPE: DNA
<213> ORGANISM: Artificial Sequence
<220> FEATURE:
<223> OTHER INFORMATION: Her-2-Her-2-IC1(F)

<400> SEQUENCE: 67
ccgcctcgag cagcagaaga tccggaagta c                                31

```
<210> SEQ ID NO 68
<211> LENGTH: 30
<212> TYPE: DNA
<213> ORGANISM: Artificial Sequence
<220> FEATURE:
<223> OTHER INFORMATION: Her-2-IC1(R)

<400> SEQUENCE: 68
cgcgactagt ttaagcccct tcggagggtg                                          30
```

COMPOSITIONS AND METHODS FOR PREVENTION OF ESCAPE MUTATION IN THE TREATMENT OF HER2/NEU OVER-EXPRESSING TUMORS

CROSS-REFERENCE TO RELATED APPLICATIONS

This application is a Continuation-In-Part of co-pending U.S. patent application Ser. No. 12/945,386, filed Nov. 12, 2010 which claims the benefit of U.S. Provisional Application Ser. No. 61/260,277, filed Nov. 11, 2009. These applications are hereby incorporated in their entirety by reference herein.

FIELD OF INVENTION

This invention provides compositions and methods for treating and vaccinating against an Her2/neu antigen-expressing tumor and inducing an immune response against dominant in a non-human animal.

BACKGROUND OF THE INVENTION

Her-2/neu (referred to henceforth as "Her-2") is a 185 kDa glycoprotein that is a member of the epidermal growth factor receptor (EGFR) family of tyrosine kinases, and consists of an extracellular domain, a transmembrane domain, and an intracellular domain which is known to be involved in cellular signaling (Bargmann C I et al, Nature 319: 226, 1986; King C R et al, Science 229: 974, 1985). In humans, the HER2 antigen is overexpressed in 25 to 40% of all breast cancers and is also overexpressed in many cancers of the ovaries, lung, pancreas, brain, and gastrointestinal tract. The overexpression of Her-2 is associated with uncontrolled cell growth and signaling, both of which contribute to the development of tumors. Patients with cancers that overexpress Her-2 exhibit tolerance even with detectable humoral, $CD8^+$ T cell, and $CD4^+$ T cell responses directed against Her-2.

*Listeria monocytogenes* is an intracellular pathogen that primarily infects antigen presenting cells and has adapted for life in the cytoplasm of these cells. Host cells, such as macrophages, actively phagocytose *L. monocytogenes* and the majority of the bacteria are degraded in the phagolysosome. Some of the bacteria escape into the host cytosol by perforating the phagosomal membrane through the action of a hemolysin, listeriolysin O (LLO). Once in the cytosol, *L. monocytogenes* can polymerize the host actin and pass directly from cell to cell further evading the host immune system and resulting in a negligible antibody response to *L. monocytogenes*.

The construction and development of a number of *Listeria monocytogenes* (Lm) based vaccines expressing small fragments of human Her2/neu protein from the extra and intracellular domains of the protein have been reported. The Her2/neu is too big to fit in Lm which necessitated the generation of Her2/neu fragments. Having found activity in each fragment independently the present invention incorporates all of the active sites from each of the independent fragments. Thus, a vaccine based upon a chimeric protein made by fusing of two of the extracellular and one intracellular fragments of the protein which included most of the known MHC class I epitopes of the Her2/neu receptor (Lm-LLO-ChHer2) has also been generated. All of these vaccines were shown to be immunogenic and efficacious in regressing pre-established tumors in FVB/N mice and delay the onset of spontaneous mammary tumors in Her2/neu-expressing transgenic animals. The encouraging results from these preliminary experiments suggested that a recombinant *Listeria*-Her21neu vaccine could be generated which could break the tolerance toward the Her2/neu self-antigen. However, the *Listeria*-Her21neu vaccines developed thus far have been based on an attenuated *Listeria* platform which used the antibiotic marker (cat), for in vitro selection of the recombinant bacteria in the presence of chloramphenicol. For clinical use, not only high attenuation is important, but also the absence of resistance to antibiotics.

Canine Osteosarcoma is a cancer of long (leg) bones that is a leading killer of large dogs over the age of 10 years. Standard treatment is amputation immediately after diagnosis, followed by chemotherapy. Invariably, however, the cancer metastasizes to the lungs. With chemotherapy, dogs survive about 12 months compared to 6 months, without treatment. The HER2 antigen is present in up to 50% of osteosarcoma.

Tumor evasion of the host immune response via escape mutations has been well documented and remains a major obstacle in tumor therapy. Thus, there is a need for developing a vaccine that has high therapeutic efficacy and that does not result in escape mutations. Furthermore, there's a high unmet need for safe, and effective cancer therapy in the animal market. The present invention meets this need by providing a recombinant *Listeria*-Her2/neu vaccine (ADXS31-164) that was generated using the LmddA vaccine vector which has a well-defined attenuation mechanism and is devoid of antibiotic selection markers. The use of this chimeric antigen does not result in escape mutations indicating that tumors do not mutate away from a therapeutic efficacious response to treatment with this novel antigen.

SUMMARY OF THE INVENTION

In one embodiment, the invention provided herein relates to an immunogenic composition comprising a fusion polypeptide, wherein said fusion polypeptide comprises a Her2/neu chimeric antigen fused to an additional polypeptide, and wherein administering the fusion protein to a subject having a Her2/neu-expressing tumor invokes mutation avoidance. In another embodiment, mutation avoidance is due to epitope spreading. In yet another embodiment, mutation avoidance is due to the chimeric nature of the antigen.

In another embodiment, the invention provided herein relates to a recombinant *Listeria* vaccine strain comprising a nucleic acid molecule, wherein and in another embodiment, the nucleic acid molecule comprises a first open reading frame encoding a polypeptide, wherein the polypeptide comprises a Her2/neu chimeric antigen, wherein the nucleic acid molecule further comprises a second open reading frame encoding a metabolic enzyme, and wherein the metabolic enzyme complements an endogenous gene that is lacking in the chromosome of the recombinant *Listeria* strain.

In one embodiment, the invention provided herein relates to a method of treating a Her-2/neu-expressing tumor growth or cancer in a non-human animal, the method comprising the step of administering a recombinant *Listeria* comprising nucleic acid encoding a fusion polypeptide, wherein said fusion polypeptide comprises a Her2/neu chimeric antigen fused to an additional adjuvant polypeptide.

In another embodiment, the invention provided herein relates to a method of preventing a Her-2/neu-expressing tumor growth or cancer in a non-human animal, the method comprising the step of administering a recombinant *Listeria* comprising nucleic acid encoding a fusion polypeptide, wherein said fusion polypeptide comprises a Her2/neu chimeric antigen fused to an additional adjuvant polypeptide.

In one embodiment, the invention provided herein relates to a method of eliciting an enhanced immune response against a Her-2/neu-expressing tumor growth or cancer in a non-human animal, the method comprising the step of administering a recombinant *Listeria* comprising a nucleic encoding a fusion polypeptide, wherein said fusion polypeptide comprises a Her2/neu chimeric antigen fused to an additional adjuvant polypeptide.

DETAILED DESCRIPTION OF THE INVENTION

Figure 1:
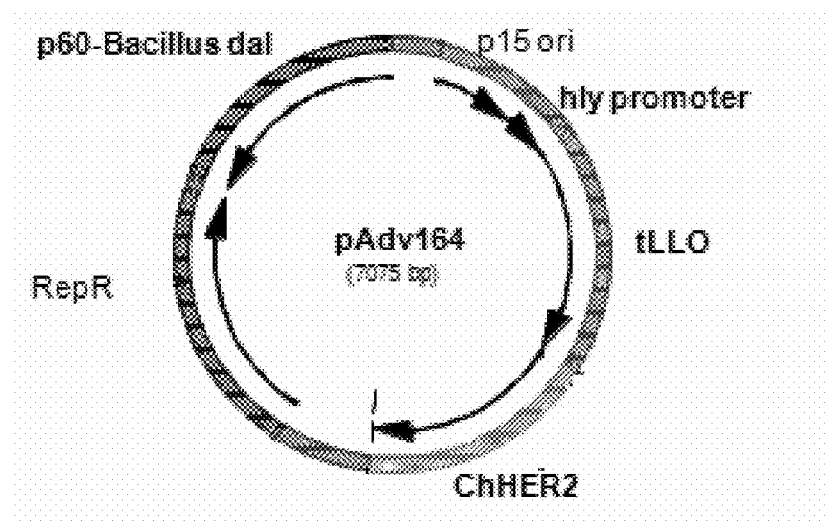
FIG. 1. Construction of ADXS31-164. (A) Plasmid map of pAdv164, which harbors *bacillus* sabtilis dal gene under the control of constitutive *Listeria* p60 promoter for complementation of the chromosomal dal-dat deletion in LmddA strain. It also contains the fusion of truncated $LLO_{(1-441)}$ to the chimeric human Her2/neu gene, which was constructed by the direct fusion of 3 fragments the Her2/neu: EC1 (aa 40-170), EC2 (aa 359-518) and ICI (aa 679-808). (B) Expression and secretion of tLLO-ChHer2 was detected in Lm-LLO-ChHer2 (Lm-LLO-138) and LmddA-LLO-ChHer2 (ADXS31-164) by western blot analysis of the TCA precipitated cell culture supernatants blotted with anti-LLO antibody. A differential band of ~104 KD corresponds to tLLO-ChHer2. The endogenous LLO is detected as a 58 KD band. *Listeria* control lacked ChHer2 expression.
Figure 1:
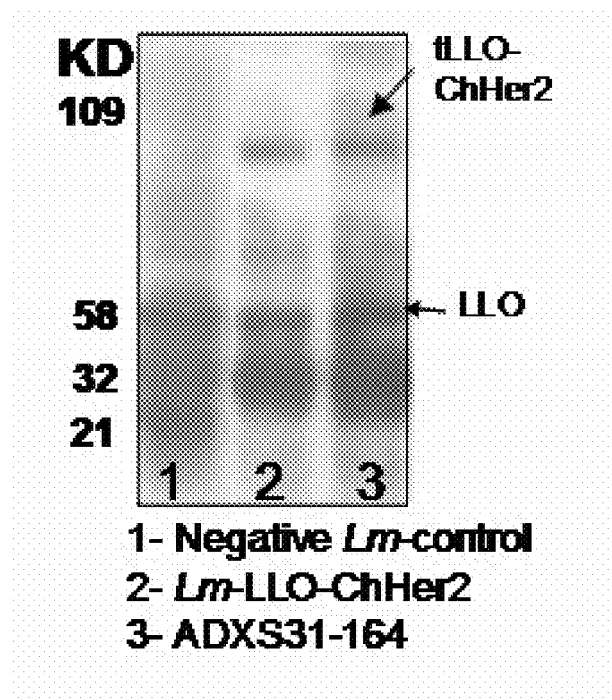

In one embodiment, provided herein are compositions and methods for preventing, treating and vaccinating against a Her2-neu antigen-expressing tumor and inducing an immune response against sub-dominant epitopes of the Her2-neu antigen, while invoking mutation avoidance. In another embodiment, mutation avoidance is due to epitope spreading. In yet another embodiment, mutation avoidance is due to the chimeric nature of the antigen.

In another embodiment, provided herein is an immunogenic composition comprising a fusion polypeptide, wherein said fusion polypeptide comprises a Her2/neu chimeric antigen fused to an additional polypeptide, and wherein administering the fusion protein to a subject having an Her2/neu-expressing tumor prevents escape mutations within said tumor. In another embodiment, provided herein is a recombinant *Listeria* vaccine strain comprising the immunogenic composition.

In one embodiment, provided herein is a method of eliciting an enhanced immune response against a Her-2/neu-expressing tumor growth or cancer in a non-human animal, the method comprising the step of administering a recombinant *Listeria* comprising a nucleic encoding a fusion polypeptide, wherein said fusion polypeptide comprises a Her2/neu chimeric antigen fused to an additional adjuvant polypeptide.

In another embodiment, provided herein is a method of preventing a Her-2/neu-expressing tumor growth or cancer in a non-human animal, the method comprising the step of administering a recombinant *Listeria* comprising nucleic acid encoding a fusion polypeptide, wherein said fusion polypeptide comprises a Her2/neu chimeric antigen fused to an additional adjuvant polypeptide.

In one embodiment, provided herein is a method of treating a Her-2/neu-expressing tumor growth or cancer in a non-human animal, the method comprising the step of administering a recombinant *Listeria* comprising nucleic acid encoding a fusion polypeptide, wherein said fusion polypeptide comprises a Her2/neu chimeric antigen fused to an additional adjuvant polypeptide. In another embodiment, the non-human animal is a canine. In yet another embodiment, the canine is a dog.

In one embodiment, provided herein is a recombinant *Listeria* vaccine strain comprising a nucleic acid molecule, wherein the nucleic acid molecule comprises a first open reading frame encoding a polypeptide, wherein the polypeptide comprises a Her2/neu chimeric antigen, wherein the nucleic acid molecule further comprises a second open reading frame encoding a metabolic enzyme, and wherein the metabolic enzyme complements an endogenous gene that is lacking in the chromosome of the recombinant *Listeria* strain. In another embodiment, the recombinant *Listeria* vaccine strain further comprises a nucleic acid molecule comprising a third open reading frame encoding a metabolic enzyme, and wherein the metabolic enzyme complements an endogenous gene that is lacking in the chromosome of the recombinant *Listeria* strain.

In another embodiment, provided herein is a recombinant *Listeria* vaccine strain comprising a nucleic acid molecule, wherein the nucleic acid molecule comprises a first open reading frame encoding a polypeptide, wherein the polypeptide comprises a Her2/neu chimeric antigen, wherein the nucleic acid molecule further comprises a second and a third open reading frame each encoding a metabolic enzyme, and wherein the metabolic enzyme complements an endogenous gene that is lacking in the chromosome of said recombinant *Listeria* strain. In one embodiment, the nucleic acid molecule is integrated into the *Listeria* genome. In another embodiment, the nucleic acid molecule is in a plasmid in the recombinant *Listeria* vaccine strain. In yet another embodiment, the plasmid is stably maintained in the recombinant *Listeria* vaccine strain in the absence of antibiotic selection. In another embodiment, the plasmid does not confer antibiotic resistance upon the recombinant *Listeria*. In another embodiment, the recombinant *Listeria* strain is attenuated. In another embodiment, the recombinant *Listeria* is an attenuated auxotrophic strain. In another embodiment, the high metabolic burden that the expression of a foreign antigen exerts on a bacterium such as one of the present invention is also an important mechanism of attenuation.

Figure 5:
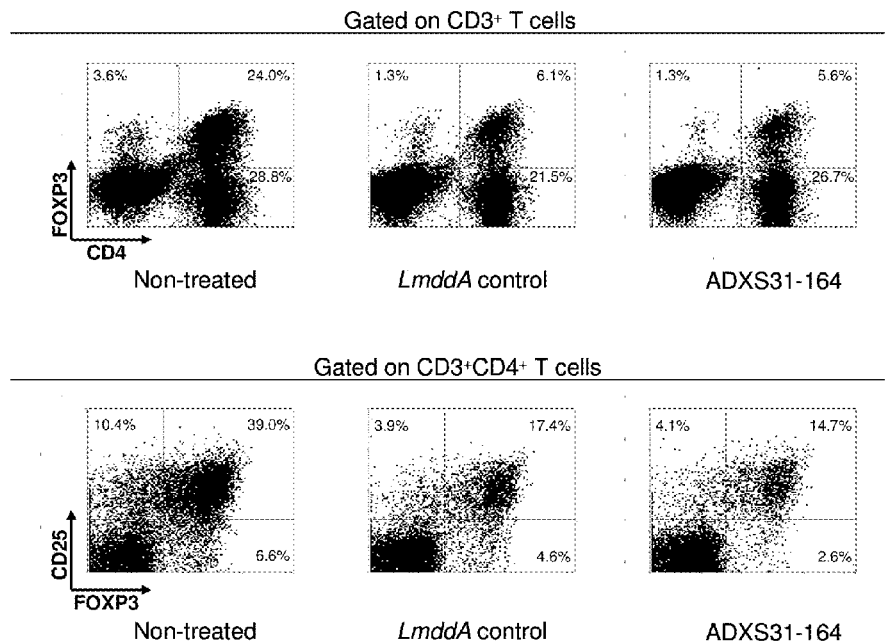
FIG. 5. Effect of immunization with ADXS31-164 on the % of tumor infiltrating Tregs in NT-2 tumors. FVB/N mice were inoculated s.c. with $1 \times 10^6$ NT-2 cells and immunized three times with each vaccine at one week intervals. Tumors were harvested 7 days after the second immunization. After isolation of the immune cells, they were stained for detection of Tregs by anti CD3, CD4, CD25 and FoxP3 antibodies. (A). dot-plots of the Tregs from a representative experiment. (B). Frequency of $CD25^+/FoxP3^+$ T cells, expressed as percentages of the total $CD3^+$ or $CD3^+CD4^+$ T cells (left panel) and intratumoral CD8/Tregs ratio (right panel) across the different treatment groups. Data is shown as mean±SEM obtained from 2 independent experiments.
Figure 5:
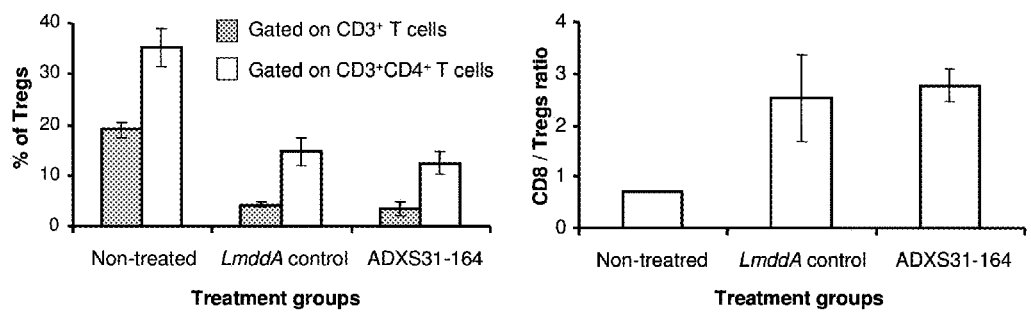

In one embodiment the attenuated strain is LmddA. In another embodiment, this strain exerts a strong adjuvant effect which is an inherent property of *Listeria*-based vaccines. One manifestation of this adjuvant effect is the 5-fold decrease in the number of the intratumoral Tregs caused by either the irrelevant *Listeria* or the ADXS-31-164 vaccines (see FIG. 5 herein). In another embodiment, the LmddA vector expressing an irrelevant antigen (HPV16 E7) is also associated with a significant decrease in the frequency of Tregs in the tumors, likely as a consequence of innate immunity responses.

In one embodiment, the attenuated auxotrophic *Listeria* vaccine strain is the ADXS-31-164 strain. ADXS-31-164 is based on a *Listeria* vaccine vector which is attenuated due to the deletion of virulence gene actA and retains the plasmid for Her2/neu expression in vivo and in vitro by complementation of dal gene. In one embodiment, ADXS31-164 expresses and secretes the chimeric Her2/neu protein fused to the first 441 amino acids of listeriolysin O (LLO). In another embodiment, ADXS31-164 exerts strong and antigen specific anti-tumor responses with ability to break tolerance toward HER2/neu in transgenic animals (see Examples). In another embodiment, the ADXS31-164 strain is highly attenuated and has a better safety profile than previous *Listeria* vaccine generation, as it is more rapidly cleared from the spleens of the immunized mice. In another embodiment, the ADXS31-164 results in a longer delay of tumor onset in transgenic animals than Lm-LLO-ChHer2, the antibiotic resistant and more virulent version of this vaccine (see FIG. 3). In another embodiment, ADXS31-164 strain is highly immunogenic, able to break tolerance toward the HER2/neu self-antigen and prevent tumor formation in Her2/neu transgenic animals. In another embodiment, ADXS31-164 causes a significant decrease in intra-tumoral T regulatory cells (Tregs). In another embodiment, the lower frequency of Tregs in tumors treated with LmddA vaccines resulted in an increased intratumoral CD8/Tregs ratio, suggesting that a more favorable tumor microenvironment can be obtained after immunization with LmddA vaccines. In another embodiment, the use of this chimeric antigen does not result in escape mutations indicating that tumors do not mutate away from a therapeutic efficacious response to treatment with this novel antigen (see example 6). In another embodiment, peripheral immunization with ADXS31-164 delays the growth of a metastatic breast cancer cell line in the brain (see Example 7).

In one embodiment, the Lm-LLO-ChHer2 strain is Lm-LLO-138.

In one embodiment, recombinant attenuated, antibiotic-free *Listeria*-expressing chimeric antigens are useful for preventing, and treating a cancer or solid tumors, as exemplified herein. In another embodiment, the tumor is a Her2/neu positive tumor. In another embodiment, the cancer is a Her2/neu-expressing cancer. In another embodiment, the cancer is breast cancer, a central nervous system (CNS) cancer, a head and neck cancer, an osteosarcoma, a canine osteosarcoma or any cancer known in the art. In another embodiment, the tumor is an osteo tumor, a breast tumor, a head and neck tumor, or any other antigen-expressing tumor known in the art. In another embodiment, recombinant *Listeria* expressing a chimeric Her2/neu are useful as a therapeutic vaccine for the treatment of Her2/neu overexpressing solid tumors. In another embodiment, the Her2/neu chimeric antigen provided herein is useful for treating Her2/neu-expressing tumors and preventing escape mutations of the same. In another embodiment, the term "escape mutation" refers to a tumor mutating away from a therapeutic efficacious response to treatment.

In one embodiment, provided herein is a nucleic acid molecule comprising a first open reading frame encoding the immunogenic composition, wherein the nucleic molecule resides within the recombinant *Listeria* vaccine strain. In another embodiment, the nucleic acid molecule provided herein is used to transform the *Listeria* in order to arrive at a recombinant *Listeria*. In another embodiment, the nucleic acid provided herein lacks a virulence gene. In another embodiment, the nucleic acid molecule integrated into the *Listeria* genome carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an ActA gene. In another embodiment, the virulence gene is a PrfA gene. As will be understood by a skilled artisan, the virulence gene can be any gene known in the art to be associated with virulence in the recombinant *Listeria*.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. Each possibility represents a separate embodiment of the present invention.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. Each possibility represents a separate embodiment of the present invention.

In another embodiment, the nucleic acids and plasmids provided herein do not confer antibiotic resistance upon the recombinant *Listeria*.

"Nucleic acid molecule" refers, in another embodiment, to a plasmid. In another embodiment, the term refers to an integration vector. In another embodiment, the term refers to a plasmid comprising an integration vector. In another embodiment, the integration vector is a site-specific integration vector. In another embodiment, a nucleic acid molecule of methods and compositions of the present invention are composed of any type of nucleotide known in the art. Each possibility represents a separate embodiment of the present invention.

"Metabolic enzyme" refers, in another embodiment, to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient. Each possibility represents a separate embodiment of the present invention.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the present invention.

In one embodiment, the present invention provides a recombinant *Listeria* strain expressing the antigen. The present invention also provides recombinant peptides comprising a listeriolysin (LLO) protein fragment fused to a Her-2 chimeric protein or fragment thereof, vaccines and immunogenic compositions comprising same, and methods of inducing an anti-Her-2 immune response and treating and vaccinating against a Her-2-expressing tumor, comprising the same.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed by any other method known in the art.

In one embodiment, the polypeptide provided herein is a fusion protein comprising an additional polypeptide selected from the group consisting of: a) non-hemolytic LLO protein or N-terminal fragment, b) a PEST sequence, or c) an ActA fragment, and further wherein said additional polypeptide is fused to the Her2/neu chimeric antigen. In another embodiment, the additional polypeptide is functional. In another embodiment, a fragment of the additional polypeptide is immunogenic. In another embodiment, the additional polypeptide is immunogenic.

In another embodiment, the polypeptide provided herein is a fusion protein comprising a non-hemolytic LLO protein or N-terminal fragment fused to the Her2/neu chimeric antigen. In another embodiment, a fusion protein of methods and compositions of the present invention comprises an ActA sequence from a *Listeria* organism. ActA proteins and fragments thereof augment antigen presentation and immunity in a similar fashion to LLO.

In another embodiment of methods and compositions of the present invention, the fusion protein comprises the Her2/neu antigen and an additional adjuvant polypeptide In one embodiment, the additional polypeptide is a non-hemolytic LLO protein or fragment thereof (Examples herein). In another embodiment, the additional polypeptide is a PEST sequence. In another embodiment, the additional polypeptide is an ActA protein or a fragment thereof. ActA proteins and fragments thereof augment antigen presentation and immunity in a similar fashion to LLO.

The additional polypeptide of methods and compositions of the present invention is, in another embodiment, a listeriolysin (LLO) peptide. In another embodiment, the additional polypeptide is an ActA peptide. In another embodiment, the additional polypeptide is a PEST-like sequence peptide. In another embodiment, the additional polypeptide is any other peptide capable of enhancing the immunogenicity of an antigen peptide. Each possibility represents a separate embodiment of the present invention.

Fusion proteins comprising the Her2/neu chimeric antigen may be prepared by any suitable method, including, for example, cloning and restriction of appropriate sequences or direct chemical synthesis by methods discussed below. Alternatively, subsequences may be cloned and the appropriate subsequences cleaved using appropriate restriction enzymes. The fragments may then be ligated to produce the desired DNA sequence. In one embodiment, DNA encoding the antigen can be produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

The results of the present invention demonstrate that administration of compositions of the present invention has utility for inducing formation of antigen-specific T cells (e.g. cytotoxic T cells) that recognize and kill tumor cells (Examples herein).

In one embodiment, the present invention provides a recombinant polypeptide comprising an N-terminal fragment of an LLO protein fused to a Her-2 chimeric protein or fused to a fragment thereof. In one embodiment, the present invention provides a recombinant polypeptide consisting of an N-terminal fragment of an LLO protein fused to a Her-2 chimeric protein or fused to a fragment thereof.

In another embodiment, the Her-2 chimeric protein of the methods and compositions of the present invention is a human Her-2 chimeric protein. In another embodiment, the Her-2 protein is a mouse Her-2 chimeric protein. In another embodiment, the Her-2 protein is a rat Her-2 chimeric protein. In another embodiment, the Her-2 protein is a primate Her-2 chimeric protein. In another embodiment, the Her-2 protein is a Her-2 chimeric protein of human or any other animal species or combinations thereof known in the art. Each possibility represents a separate embodiment of the present invention.

In another embodiment, a Her-2 protein is a protein referred to as "HER-2/neu," "Erbb2," "v-erb-b2," "c-erb-b2," "neu," or "cNeu." Each possibility represents a separate embodiment of the present invention.

In one embodiment, the Her2-neu chimeric protein, harbors two of the extracellular and one intracellular fragments of Her2/neu antigen showing clusters of MHC-class I epitopes of the oncogene, where, in another embodiment, the chimeric protein, harbors 3 H2Dq and at least 17 of the mapped human MHC-class I epitopes of the Her2/neu antigen (fragments EC1, EC2, and IC1) (See FIG. 1). In another embodiment, the chimeric protein harbors at least 13 of the mapped human MHC-class I epitopes (fragments EC2 and IC1). In another embodiment, the chimeric protein harbors at least 14 of the mapped human MHC-class I epitopes (fragments EC1 and IC1). In another embodiment, the chimeric protein harbors at least 9 of the mapped human MHC-class I epitopes (fragments EC1 and IC2). In another embodiment, the Her2-neu chimeric protein is fused to a non-hemolytic listeriolysin O (LLO). In another embodiment, the Her2-neu chimeric protein is fused to the first 441 amino acids of the *Listeria*-monocytogenes listeriolysin O (LLO) protein and expressed and secreted by the *Listeria monocytogenes* attenuated auxotrophic strain LmddA. In another embodiment, the expression and secretion of the fusion protein tLLO-ChHer2 from the attenuated auxotrophic strain provided herein that expresses a chimeric Her2/neu antigen/LLO fusion protein is comparable to that of the Lm-LLO-ChHer2 in TCA precipitated cell culture supernatants after 8 hours of in vitro growth (See FIG. 1B).

Figure 2:
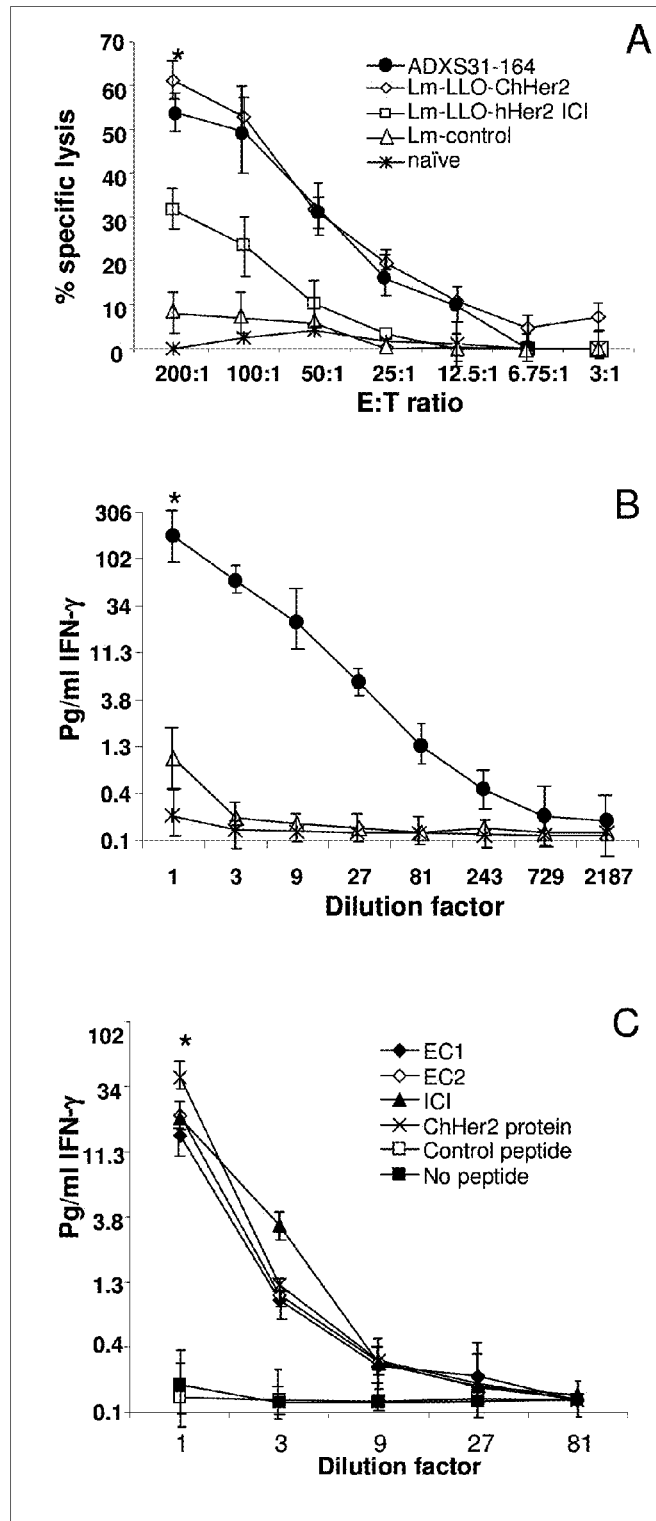
FIG. 2. Immunogenic properties of ADXS31-164 (A) Cytotoxic T cell responses elicited by Her2/neu *Listeria*-based vaccines in splenocytes from immunized mice were tested using NT-2 cells as stimulators and 3T3/neu cells as targets. Lm-control was based on the LmddA background that was identical in all ways but expressed an irrelevant antigen (HPV16-E7). (B) IFN-γ secreted by the splenocytes from immunized FVB/N mice into the cell culture medium, measured by ELISA, after 24 hours of in vitro stimulation with mitomycin C treated NT-2 cells. (C) IFN-γ secretion by splenocytes from HLA-A2 transgenic mice immunized with the chimeric vaccine, in response to in vitro incubation with peptides from different regions of the protein. A recombinant ChHer2 protein was used as positive control and an irrelevant peptide or no peptide groups constituted the negative controls as listed in the figure legend. IFN-γ secretion was detected by an ELISA assay using cell culture supernatants harvested after 72 hours of co-incubation. Each data point was an average of triplicate data+/−standard error. * P value<0.001.

In one embodiment, no CTL activity is detected in naïve animals or mice injected with an irrelevant *Listeria* vaccine (See FIG. 2A). While in another embodiment, the attenuated auxotrophic strain (ADXS31-164) provided herein is able to stimulate the secretion of IFN-γ by the splenocytes from wild type FVB/N mice (FIG. 2B).

In another embodiment, the metabolic enzyme of the methods and compositions provided herein is an amino acid metabolism enzyme, where, in another embodiment, the metabolic enzyme is an alanine racemase enzyme. In another embodiment, the metabolic enzyme is a D-amino acid transferase enzyme. In another embodiment, the metabolic enzyme catalyzes a formation of an amino acid used for a cell wall synthesis in the recombinant *Listeria* strain, where in another embodiment, the metabolic enzyme is an alanine racemase enzyme.

In another embodiment, the gene encoding the metabolic enzyme is expressed under the control of the *Listeria* p60 promoter. In another embodiment, the inlA (encodes internalin) promoter is used. In another embodiment, the hly promoter is used. In another embodiment, the ActA promoter is used. In another embodiment, the integrase gene is expressed under the control of any other gram positive promoter. In another embodiment, the gene encoding the metabolic enzyme is expressed under the control of any other promoter that functions in *Listeria*. The skilled artisan will appreciate that other promoters or polycistronic expression cassettes may be used to drive the expression of the gene. Each possibility represents a separate embodiment of the present invention.

In another embodiment, the Her-2 chimeric protein is encoded by the following nucleic acid sequence set forth in SEQ ID NO:1

```
                                                                (SEQ ID NO: 1)
gagacccacctggacatgctccgccacctctaccagggctgccaggtggtgcagggaaacctggaactcacctacctgcccaccaatg ccagcctgtccttcctgcaggatatccaggaggtgcagggctacgtgctcatcgctcacaaccaagtgaggcaggtcccactgcagag gctgcggattgtgcgaggcacccagctctttgaggacaactatgccctggccgtgctagacaatggagacccgctgaacaataccaccc ctgtcacagggcctcccaggaggcctgcgggagctgcagcttcgaagcctcacagagatcttgaaaggaggggtcttgatccagc ggaaccccagctctgctaccaggacacgattttgtggaagaatatccaggagtttgctggctgcaagaagatctttgggagcctggcatt tctgccggagagctttgatggggacccagcctccaacactgccccgctccagccagagcagctccaagtgtttgagactctggaagaga tcacaggttacctatacatctcagcatggccggacagctgcctgacctcagcgtcttccagaacctgcaagtaatccggggacgaattct gcacaatggcgcctactcgctgaccctgcaagggctgggcatcagctggctggggctgcgctcactgagggaactgggcagtggact
```

-continued

```
ggccctcatccaccataacacccacctctgcttcgtgcacacggtgccctgggaccagctctttcggaacccgcaccaagctctgctcca cactgccaaccggccagaggacgagtgtgtgggcgagggcctggcctgccaccagctgtgcgcccgagggcagcagaagatccgg aagtacacgatgcggagactgctgcaggaaacggagctggtggagccgctgacacctagcggagcgatgcccaaccaggcgcagat gcggatcctgaaagagacggagctgaggaaggtgaaggtgcttggatctggcgcttttggcacagtctacaagggcatctggatccctg atggggagaatgtgaaaattccagtggccatcaaagtgttgagggaaaacacatccccaaagccaacaaagaaatcttagacgaagc atacgtgatggctggtgtgggctccccatatgtctcccgccttctgggcatctgcctgacatccacggtgcagctggtgacacagcttatg ccctatggctgcctcttagactaa.
```

In another embodiment, the Her-2 chimeric protein has the sequence:

```
                                                          (SEQ ID NO: 2)
E T H L D M L R H L Y Q G C Q V V Q G N L E L T Y L P T N A S L S

F L Q D I Q E V Q G Y V L I A H N Q V R Q V P L Q R L R I V R G T

Q L F E D N Y A L A V L D N G D P L N N T T P V T G A S P G G L R

E L Q L R S L T E I L K G G V L I Q R N P Q L C Y Q D T I L W K N I

Q E F A G C K K I F G S L A F L P E S F D G D P A S N T A P L Q P E

Q L Q V F E T L E E I T G Y L Y S A W P D S L P D L S V F Q N L Q

V I R G R I L H N G A Y S L T L Q G L G I S W L G R S L R E L G S

G L A L I H H N T H L C F V H T V P W D Q L F R N P H Q A L L H T

A N R P E D E C V G E G L A C H Q L C A R G Q Q K I R K Y T M R

R L L Q E T E L V E P L T P S G A M P N Q A Q M R I L K E T E L R

K V K V L G S G A F G T V Y K G I W I P D G E N V K I P V A I K V

L R E N T S P K A N K E I L D E A Y V M A G V G S P Y V S R L L G I C

L T S T V Q L V T Q L M P Y G C L L D.
```

In one embodiment, the Her2 chimeric protein or fragment thereof of the methods and compositions provided herein does not include a signal sequence thereof. In another embodiment, omission of the signal sequence enables the Her2 fragment to be successfully expressed in *Listeria*, due the high hydrophobicity of the signal sequence. Each possibility represents a separate embodiment of the present invention.

In another embodiment, the fragment of a Her2 chimeric protein of methods and compositions of the present invention does not include a transmembrane domain (TM) thereof. In one embodiment, omission of the TM enables the Her-2 fragment to be successfully expressed in *Listeria*, due the high hydrophobicity of the TM. Each possibility represents a separate embodiment of the present invention.

In one embodiment, the nucleic acid sequence of rat-Her2/neu gene is

```
                                             (SEQ ID NO: 45)
CCGGAATCGCGGGCACCCAAGTGTGTACCGGCACAGACATGAAGTTGCGGCTCC

CTGCCAGTCCTGAGACCCACCTGGACATGCTCCGCCACCTGTACCAGGGCTGTCA

GGTAGTGCAGGGCAACTTGGAGCTTACCTACGTGCCTGCCAATGCCAGCCTCTCA

TTCCTGCAGGACATCCAGGAAGTTCAGGGTTACATGCTCATCGCTCACAACCAGG

TGAAGCGCGTCCCACTGCAAAGGCTGCGCATCGTGAGAGGGACCCAGCTCTTTG

AGGACAAGTATGCCCTGGCTGTGCTAGACAACCGAGATCCTCAGGACAATGTCG

CCGCCTCCACCCCAGGCAGAACCCCAGAGGGGCTGCGGGAGCTGCAGCTTCGAA

GTCTCACAGAGATCCTGAAGGGAGGAGTTTTGATCCGTGGGAACCCTCAGCTCTG

CTACCAGGACATGGTTTTGTGGAAGGACGTCTTCCGCAAGAATAACCAACTGGCT
```

-continued

```
CCTGTCGATATAGACACCAATCGTTCCCGGGCCTGTCCACCTTGTGCCCCCGCCT
GCAAAGACAATCACTGTTGGGGTGAGAGTCCGGAAGACTGTCAGATCTTGACTG
GCACCATCTGTACCAGTGGTTGTGCCCGGTGCAAGGGCCGGCTGCCCACTGACTG
CTGCCATGAGCAGTGTGCCGCAGGCTGCACGGGCCCAAGCATTCTGACTGCCTG
GCCTGCCTCCACTTCAATCATAGTGGTATCTGTGAGCTGCACTGCCCAGCCCTCGT
CACCTACAACACAGACACCTTTGAGTCCATGCACAACCCTGAGGGTCGCTACACC
TTTGGTGCCAGCTGCGTGACCACCTGCCCCTACAACTACCTGTCTACGGAAGTGG
GATCCTGCACTCTGGTGTGTCCCCCGAATAACCAAGAGGTCACAGCTGAGGACG
GAACACAGCGTTGTGAGAAATGCAGCAAGCCCTGTGCTCGAGTGTGCTATGGTCT
GGGCATGGAGCACCTTCGAGGGGCGAGGGCCATCACCAGTGACAATGTCCAGGA
GTTTGATGGCTGCAAGAAGATCTTTGGGAGCCTGGCATTTTTGCCGGAGAGCTTT
GATGGGACCCCTCCTCCGGCATTGCTCCGCTGAGGCCTGAGCAGCTCCAAGTGT
TCGAAACCCTGGAGGAGATCACAGGTTACCTGTACATCTCAGCATGGCCAGACA
GTCTCCGTGACCTCAGTGTCTTCCAGAACCTTCGAATCATTCGGGGACGGATTCT
CCACGATGGCGCGTACTCATTGACACTGCAAGGCCTGGGGATCCACTCGCTGGGG
CTGCGCTCACTGCGGGAGCTGGGCAGTGGATTGGCTCTGATTCACCGCAACGCCC
ATCTCTGCTTTGTACACACTGTACCTTGGGACCAGCTCTTCCGGAACCCACATCA
GGCCCTGCTCCACAGTGGGAACCGGCCGGAAGAGGATTGTGGTCTCGAGGGCTT
GGTCTGTAACTCACTGTGTGCCCACGGGCACTGCTGGGGGCCAGGGCCCACCCAG
TGTGTCAACTGCAGTCATTTCCTTCGGGGCCAGGAGTGTGTGGAGGAGTGCCGAG
TATGGAAGGGGCTCCCCCGGGAGTATGTGAGTGACAAGCGCTGTCTGCCGTGTCA
CCCCGAGTGTCAGCCTCAAAACAGCTCAGAGACCTGCTTTGGATCGGAGGCTGAT
CAGTGTGCAGCCTGCGCCCACTACAAGGACTCGTCCTCCTGTGTGGCTCGCTGCC
CCAGTGGTGTGAAACCGGACCTCTCCTACATGCCCATCTGGAAGTACCCGGATGA
GGAGGGCATATGCCAGCCGTGCCCCATCAACTGCACCCACTCCTGTGTGGATCTG
GATGAACGAGGCTGCCCAGCAGAGCAGAGAGCCAGCCCGGTGACATTCATCATT
GCAACTGTAGTGGGCGTCCTGCTGTTCCTGATCTTAGTGGTGGTCGTTGGAATCCT
AATCAAACGAAGGAGACAGAAGATCCGGAAGTATACGATGCGTAGGCTGCTGCA
GGAAACTGAGTTAGTGGAGCCGCTGACGCCCAGCGGAGCAATGCCCAACCAGGC
TCAGATGCGGATCCTAAAAGAGACGGAGCTAAGGAAGGTGAAGGTGCTTGGATC
AGGAGCTTTTGGCACTGTCTACAAGGGCATCTGGATCCCAGATGGGGAGAATGT
GAAAATCCCCGTGGCTATCAAGGTGTTGAGAGAAAACACATCTCCTAAAGCCAA
CAAAGAAATTCTAGATGAAGCGTATGTGATGGCTGGTGTGGGTTCTCCGTATGTG
TCCCGCCTCCTGGGCATCTGCCTGACATCCACAGTACAGCTGGTGACACAGCTTA
TGCCCTACGGCTGCCTTCTGGACCATGTCCGAGAACACCGAGGTCGCCTAGGCTC
CCAGGACCTGCTCAACTGGTGTGTTCAGATTGCCAAGGGGATGAGCTACCTGGAG
GACGTGCGGCTTGTACACAGGGACCTGGCTGCCCGGAATGTGCTAGTCAAGAGT
CCCAACCACGTCAAGATTACAGATTTCGGGCTGGCTCGGCTGCTGGACATTGATG
AGACAGAGTACCATGCAGATGGGGGCAAGGTGCCCATCAAATGGATGGCATTGG
AATCTATTCTCAGACGCCGGTTCACCCATCAGAGTGATGTGTGGAGCTATGGAGT
```

```
GACTGTGTGGGAGCTGATGACTTTTGGGGCCAAACCTTACGATGGAATCCCAGCC

CGGGAGATCCCTGATTTGCTGGAGAAGGGAGAACGCCTACCTCAGCCTCCAATCT

GCACCATTGATGTCTACATGATTATGGTCAAATGTTGGATGATTGACTCTGAATG

TCGCCCGAGATTCCGGGAGTTGGTGTCAGAATTTTCACGTATGGCGAGGGACCCC

CAGCGTTTTGTGGTCATCCAGAACGAGGACTTGGGCCCATCCAGCCCCATGGACA

GTACCTTCTACCGTTCACTGCTGGAAGATGATGACATGGGTGACCTGGTAGACGC

TGAAGAGTATCTGGTGCCCCAGCAGGGATTCTTCTCCCCGGACCCTACCCCAGGC

ACTGGGAGCACAGCCCATAGAAGGCACCGCAGCTCGTCCACCAGGAGTGGAGGT

GGTGAGCTGACACTGGGCCTGGAGCCCTCGGAAGAAGGGCCCCCCAGATCTCCA

CTGGCTCCCTCGGAAGGGGCTGGCTCCGATGTGTTTGATGGTGACCTGGCAATGG

GGGTAACCAAAGGGCTGCAGAGCCTCTCTCCACATGACCTCAGCCCTCTACAGCG

GTACAGCGAGGACCCCACATTACCTCTGCCCCCCGAGACTGATGGCTATGTTGCT

CCCCTGGCCTGCAGCCCCCAGCCCGAGTATGTGAACCAATCAGAGGTTCAGCCTC

AGCCTCCTTTAACCCCAGAGGGTCCTCTGCCTCCTGTCCGGCCTGCTGGTGCTACT

CTAGAAAGACCCAAGACTCTCTCTCCTGGGAAGAATGGGGTTGTCAAAGACGTTT

TTGCCTTCGGGGGTGCTGTGGAGAACCCTGAATACTTAGTACCGAGAGAAGGCA

CTGCCTCTCCGCCCACCCTTCTCCTGCCTTCAGCCCAGCCTTTGACAACCTCTAT

TACTGGGACCAGAACTCATCGGAGCAGGGGCCTCCACCAAGTAACTTTGAAGGG

ACCCCCACTGCAGAGAACCCTGAGTACCTAGGCCTGGATGTACCTGTA.
```

In one embodiment, the nucleic acid sequence encoding the rat/her2/neu EC1 fragment is

```
                                              (SEQ ID NO: 46)
CCCAGGCAGAACCCCAGAGGGGCTGCGGGAGCTGCAGCTTCGAAGTCTCACAGA

GATCCTGAAGGGAGGAGTTTTGATCCGTGGGAACCCTCAGCTCTGCTACCAGGAC

ATGGTTTTGTGGAAGGACGTCTTCCGCAAGAATAACCAACTGGCTCCTGTCGATA

TAGACACCAATCGTTCCCGGGCCTGTCCACCTTGTGCCCCCGCCTGCAAAGACAA

TCACTGTTGGGGTGAGAGTCCGGAAGACTGTCAGATCTTGACTGGCACCATCTGT

ACCAGTGGTTGTGCCCGGTGCAAGGGCCGGCTGCCCACTGACTGCTGCCATGAGC

AGTGTGCCGCAGGCTGCACGGGCCCCAAGCA.
```

In another embodiment, the nucleic acid sequence encoding the rat her2/neu EC2 fragment is:

```
                                              (SEQ ID NO: 47)
GGTCACAGCTGAGGACGGAACACAGCGTTGTGAGAAATGCAGCAAGCCCTGTGC

TCGAGTGTGCTATGGTCTGGGCATGGAGCACCTTCGAGGGGCGAGGGCCATCAC

CAGTGACAATGTCCAGGAGTTTGATGGCTGCAAGAAGATCTTTGGGAGCCTGGC

ATTTTTGCCGGAGAGCTTTGATGGGGACCCCTCCTCCGGCATTGCTCCGCTGAGG

CCTGAGCAGCTCCAAGTGTTCGAAACCCTGGAGGAGATCACAGGTTACCTGTACA

TCTCAGCATGGCCAGACAGTCTCCGTGACCTCAGTGTCTTCCAGAACCTTCGAAT

CATTCGGGGACGGATTCTCCACGATGGCGCGTACTCATTGACACTGCAAGGCCTG

GGGATCCACTCGCTGGGGCTGCGCTCACTGCGGGAGCTGGGCAGTGGATTGGCTC
```

```
TGATTCACCGCAACGCCCATCTCTGCTTTGTACACACTGTACCTTGGGACCAGCTC

TTCCGGAACCCACATCAGGCCCTGCTCCACAGTGGGAACCGGCCGGAAGAGGAT

TGTGGTCTCGAGGGCTTGGTCTGTAACTCACTGTGTGCCCACGGGCACTGCTGGG

GGCCAGGGCCCACCCA.
```

In another embodiment, the nucleic acid sequence encoding the rat her2/neu IC1 fragment is:

```
                                               (SEQ ID NO: 48)
CGCCCAGCGGAGCAATGCCCAACCAGGCTCAGATGCGGATCCTAAAAGAG

ACGGAGCTAAGGAAGGTGAAGGTGCTTGGATCAGGAGCTTTTGGCACTGTCTAC

AAGGGCATCTGGATCCCAGATGGGGAGAATGTGAAAATCCCCGTGGCTATCAAG

GTGTTGAGAGAAAACACATCTCCTAAAGCCAACAAAGAAATTCTAGATGAAGCG

TATGTGATGGCTGGTGTGGGTTCTCCGTATGTGTCCCGCCTCCTGGGCATCTGCCT

GACATCCACAGTACAGCTGGTGACACAGCTTATGCCCTACGGCTGCCTTCTGGAC

CATGTCCGAGAACACCGAGGTCGCCTAGGCTCCCAGGACCTGCTCAACTGGTGTG

TTCAGATTGCCAAGGGGATGAGCTACCTGGAGGACGTGCGGCTTGTACACAGGG

ACCTGGCTGCCCGGAATGTGCTAGTCAAGAGTCCCAACCACGTCAAGATTACAG

ATTTCGGGCTGGCTCGGCTGCTGGACATTGATGAGACAGAGTACCATGCAGATGG

GGGCAAGGTGCCCATCAAATGGATGGCATTGGAATCTATTCTCAGACGCCGGTTC

ACCCATCAGAGTGATGTGTGGAGCTATGGAGTGACTGTGTGGGAGCTGATGACTT

TTGGGGCCAAACCTTACGATGGAATCCCAGCCCGGGAGATCCCTGATTTGCTGGA

GAAGGGAGAACGCCTACCTCAGCCTCCAATCTGCACCATTGATGTCTACATGATT

ATGGTCAAATGTTGGATGATTGACTCTGAATGTCGCCCGAGATTCCGGGAGTTGG

TGTCAGAATTTTCACGTATGGCGAGGGACCCCCAGCGTTTTGTGGTCATCCAGAA

CGAGGACTTGGGCCCATCCAGCCCCATGGACAGTACCTTCTACCGTTCACTGCTG

GAA.
```

In one embodiment, the nucleic acid sequence of human-Her2/neu gene is:

```
                                               (SEQ ID NO: 49)
ATGGAGCTGGCGGCCTTGTGCCGCTGGGGGCTCCTCCTCGCCCTCTTGCCCCCCG

GAGCCGCGAGCACCCAAGTGTGCACCGGCACAGACATGAAGCTGCGGCTCCCTG

CCAGTCCCGAGACCCACCTGGACATGCTCCGCCACCTCTACCAGGGCTGCCAGGT

GGTGCAGGGAAACCTGGAACTCACCTACCTGCCCACCAATGCCAGCCTGTCCTTC

CTGCAGGATATCCAGGAGGTGCAGGGCTACGTGCTCATCGCTCACAACCAAGTG

AGGCAGGTCCCACTGCAGAGGCTGCGGATTGTGCGAGGCACCCAGCTCTTTGAG

GACAACTATGCCCTGGCCGTGCTAGACAATGGAGACCCGCTGAACAATACCACC

CCTGTCACAGGGGCCTCCCCAGGAGGCCTGCGGGAGCTGCAGCTTCGAAGCCTC

ACAGAGATCTTGAAAGGAGGGGTCTTGATCCAGCGGAACCCCCAGCTCTGCTAC

CAGGACACGATTTTGTGGAAGGACATCTTCCACAAGAACAACCAGCTGGCTCTCA

CACTGATAGACACCAACCGCTCTCGGGCCTGCCACCCCTGTTCTCCGATGTGTAA

GGGCTCCCGCTGCTGGGGAGAGAGTTCTGAGGATTGTCAGAGCCTGACGCGCAC
```

-continued
```
TGTCTGTGCCGGTGGCTGTGCCCGCTGCAAGGGGCCACTGCCCACTGACTGCTGC

CATGAGCAGTGTGCTGCCGGCTGCACGGGCCCCAAGCACTCTGACTGCCTGGCCT

GCCTCCACTTCAACCACAGTGGCATCTGTGAGCTGCACTGCCCAGCCCTGGTCAC

CTACAACACAGACACGTTTGAGTCCATGCCCAATCCCGAGGGCCGGTATACATTC

GGCGCCAGCTGTGTGACTGCCTGTCCCTACAACTACCTTTCTACGGACGTGGGAT

CCTGCACCCTCGTCTGCCCCCTGCACAACCAAGAGGTGACAGCAGAGGATGGAA

CACAGCGGTGTGAGAAGTGCAGCAAGCCCTGTGCCCGAGTGTGCTATGGTCTGG

GCATGGAGCACTTGCGAGAGGTGAGGGCAGTTACCAGTGCCAATATCCAGGAGT

TTGCTGGCTGCAAGAAGATCTTTGGGAGCCTGGCATTTCTGCCGGAGAGCTTTGA

TGGGGACCCAGCCTCCAACACTGCCCCGCTCCAGCCAGAGCAGCTCCAAGTGTTT

GAGACTCTGGAAGAGATCACAGGTTACCTATACATCTCAGCATGGCCGGACAGC

CTGCCTGACCTCAGCGTCTTCCAGAACCTGCAAGTAATCCGGGGACGAATTCTGC

ACAATGGCGCCTACTCGCTGACCCTGCAAGGGCTGGGCATCAGCTGGCTGGGGCT

GCGCTCACTGAGGGAACTGGGCAGTGGACTGGCCCTCATCCACCATAACACCCA

CCTCTGCTTCGTGCACACGGTGCCCTGGGACCAGCTCTTTCGGAACCCGCACCAA

GCTCTGCTCCACACTGCCAACCGGCCAGAGGACGAGTGTGTGGGCGAGGGCCTG

GCCTGCCACCAGCTGTGCGCCCGAGGGCACTGCTGGGGTCCAGGGCCCACCCAG

TGTGTCAACTGCAGCCAGTTCCTTCGGGGCCAGGAGTGCGTGGAGGAATGCCGA

GTACTGCAGGGGCTCCCCAGGGAGTATGTGAATGCCAGGCACTGTTTGCCGTGCC

ACCCTGAGTGTCAGCCCCAGAATGGCTCAGTGACCTGTTTTGGACCGGAGGCTGA

CCAGTGTGTGGCCTGTGCCCACTATAAGGACCCTCCCTTCTGCGTGGCCCGCTGC

CCCAGCGGTGTGAAACCTGACCTCTCCTACATGCCCATCTGGAAGTTTCCAGATG

AGGAGGGCGCATGCCAGCCTTGCCCCATCAACTGCACCCACTCCTGTGTGGACCT

GGATGACAAGGGCTGCCCCGCCGAGCAGAGAGCCAGCCCTCTGACGTCCATCGT

CTCTGCGGTGGTTGGCATTCTGCTGGTCGTGGTCTTGGGGGTGGTCTTTGGGATCC

TCATCAAGCGACGGCAGCAGAAGATCCGGAAGTACACGATGCGGAGACTGCTGC

AGGAAACGGAGCTGGTGGAGCCGCTGACACCTAGCGGAGCGATGCCCAACCAGG

CGCAGATGCGGATCCTGAAAGAGACGGAGCTGAGGAAGGTGAAGGTGCTTGGAT

CTGGCGCTTTTGGCACAGTCTACAAGGGCATCTGGATCCCTGATGGGGAGAATGT

GAAAATTCCAGTGGCCATCAAAGTGTTGAGGGAAAACACATCCCCCAAAGCCAA

CAAAGAAATCTTAGACGAAGCATACGTGATGGCTGGTGTGGGCTCCCCATATGTC

TCCCGCCTTCTGGGCATCTGCCTGACATCCACGGTGCAGCTGGTGACACAGCTTA

TGCCCTATGGCTGCCTCTTAGACCATGTCCGGGAAAACCGCGGACGCCTGGGCTC

CCAGGACCTGCTGAACTGGTGTATGCAGATTGCCAAGGGGATGAGCTACCTGGA

GGATGTGCGGCTCGTACACAGGGACTTGGCCGCTCGGAACGTGCTGGTCAAGAG

TCCCAACCATGTCAAAATTACAGACTTCGGGCTGGCTCGGCTGCTGGACATTGAC

GAGACAGAGTACCATGCAGATGGGGGCAAGGTGCCCATCAAGTGGATGGCGCTG

GAGTCCATTCTCCGCCGGCGGTTCACCCACCAGAGTGATGTGTGGAGTTATGGTG

TGACTGTGTGGGAGCTGATGACTTTTGGGGCCAAACCTTACGATGGGATCCCAGC

CCGGGAGATCCCTGACCTGCTGGAAAAGGGGGAGCGGCTGCCCCAGCCCCCCAT

CTGCACCATTGATGTCTACATGATCATGGTCAAATGTTGGATGATTGACTCTGAA
```

-continued

```
TGTCGGCCAAGATTCCGGGAGTTGGTGTCTGAATTCTCCCGCATGGCCAGGGACC

CCCAGCGCTTTGTGGTCATCCAGAATGAGGACTTGGGCCCAGCCAGTCCCTTGGA

CAGCACCTTCTACCGCTCACTGCTGGAGGACGATGACATGGGGGACCTGGTGGAT

GCTGAGGAGTATCTGGTACCCCAGCAGGGCTTCTTCTGTCCAGACCCTGCCCCGG

GCGCTGGGGGCATGGTCCACCACAGGCACCGCAGCTCATCTACCAGGAGTGGCG

GTGGGGACCTGACACTAGGGCTGGAGCCCTCTGAAGAGGAGGCCCCCAGGTCTC

CACTGGCACCCTCCGAAGGGGCTGGCTCCGATGTATTTGATGGTGACCTGGGAAT

GGGGGCAGCCAAGGGGCTGCAAAGCCTCCCCACACATGACCCCAGCCCTCTACA

GCGGTACAGTGAGGACCCCACAGTACCCCTGCCCTCTGAGACTGATGGCTACGTT

GCCCCCCTGACCTGCAGCCCCCAGCCTGAATATGTGAACCAGCCAGATGTTCGGC

CCCAGCCCCCTTCGCCCCGAGAGGGCCCTCTGCCTGCTGCCCGACCTGCTGGTGC

CACTCTGGAAAGGGCCAAGACTCTCTCCCCAGGGAAGAATGGGGTCGTCAAAGA

CGTTTTTGCCTTTGGGGGTGCCGTGGAGAACCCCGAGTACTTGACACCCCAGGGA

GGAGCTGCCCCTCAGCCCCACCCTCCTCCTGCCTTCAGCCCAGCCTTCGACAACC

TCTATTACTGGGACCAGGACCCACCAGAGCGGGGGGCTCCACCCAGCACCTTCA

AAGGGACACCTACGGCAGAGAACCCAGAGTACCTGGGTCTGGACGTGCCAGTGT

GAACCAGAAGGCCAAGTCCGCAGAAGCCCTGA.
```

In another embodiment, the nucleic acid sequence encoding the human her2/neu EC1 fragment implemented into the chimera spans from 120-510 bp of the human EC1 region and is set forth in (SEQ ID NO: 50).

```
                                              (SEQ ID NO: 50)
GAGACCCACCTGGACATGCTCCGCCACCTCTACCAGGGCTGCCAGGTGGTGCAG

GGAAACCTGGAACTCACCTACCTGCCCACCAATGCCAGCCTGTCCTTCCTGCAGG

ATATCCAGGAGGTGCAGGGCTACGTGCTCATCGCTCACAACCAAGTGAGGCAGG

TCCCACTGCAGAGGCTGCGGATTGTGCGAGGCACCCAGCTCTTTGAGGACAACTA

TGCCCTGGCCGTGCTAGACAATGGAGACCCGCTGAACAATACCACCCCTGTCACA

GGGGCCTCCCCAGGAGGCCTGCGGGAGCTGCAGCTTCGAAGCCTCACAGAGATC

TTGAAAGGAGGGGTCTTGATCCAGCGGAACCCCCAGCTCTGCTACCAGGACACG

ATTTTGTGGAAG.
```

In one embodiment, the complete EC1 human her2/neu fragment spans from (58-979 bp of the human her2/neu gene and is set forth in (SEQ ID NO: 54).

```
                                              (SEQ ID NO: 54)
GCCGCGAGCACCCAAGTGTGCACCGGCACAGACATGAAGCTGCGGCTCCCTGCC

AGTCCCGAGACCCACCTGGACATGCTCCGCCACCTCTACCAGGGCTGCCAGGTGG

TGCAGGGAAACCTGGAACTCACCTACCTGCCCACCAATGCCAGCCTGTCCTTCCT

GCAGGATATCCAGGAGGTGCAGGGCTACGTGCTCATCGCTCACAACCAAGTGAG

GCAGGTCCCACTGCAGAGGCTGCGGATTGTGCGAGGCACCCAGCTCTTTGAGGAC

AACTATGCCCTGGCCGTGCTAGACAATGGAGACCCGCTGAACAATACCACCCCTG

TCACAGGGGCCTCCCCAGGAGGCCTGCGGGAGCTGCAGCTTCGAAGCCTCACAG

AGATCTTGAAAGGAGGGGTCTTGATCCAGCGGAACCCCCAGCTCTGCTACCAGGA
```

-continued
```
CACGATTTTGTGGAAGGACATCTTCCACAAGAACAACCAGCTGGCTCTCACACTG

ATAGACACCAACCGCTCTCGGGCCTGCCACCCCTGTTCTCCGATGTGTAAGGGCT

CCCGCTGCTGGGGAGAGAGTTCTGAGGATTGTCAGAGCCTGACGCGCACTGTCTG

TGCCGGTGGCTGTGCCCGCTGCAAGGGGCCACTGCCCACTGACTGCTGCCATGAG

CAGTGTGCTGCCGGCTGCACGGGCCCCAAGCACTCTGACTGCCTGGCCTGCCTCC

ACTTCAACCACAGTGGCATCTGTGAGCTGCACTGCCCAGCCCTGGTCACCTACAA

CACAGACACGTTTGAGTCCATGCCCAATCCCGAGGGCCGGTATACATTCGGCGCC

AGCTGTGTGACTGCCTGTCCCTACAACTACCTTTCTACGGACGTGGGATCCTGCAC

CCTCGTCTGCCCCCTGCACAACCAAGAGGTGACAGCAGAGGAT.
```

In another embodiment, the nucleic acid sequence encoding the human her2/neu EC2 fragment implemented into the chimera spans from 1077-1554 bp of the human her2/neu EC2 fragment and includes a 50 bp extension, and is set forth in (SEQ ID NO: 51).

```
                                         (SEQ ID NO: 51)
AATATCCAGGAGTTTGCTGGCTGCAAGAAGATCTTTGGGAGCCTGGCATTTCTGCC

GGAGAGCTTTGATGGGGACCCAGCCTCCAACACTGCCCCGCTCCAGCCAGAGCAG

CTCCAAGTGTTTGAGACTCTGGAAGAGATCACAGGTTACCTATACATCTCAGCATG

GCCGGACAGCCTGCCTGACCTCAGCGTCTTCCAGAACCTGCAAGTAATCCGGGGA

CGAATTCTGCACAATGGCGCCTACTCGCTGACCCTGCAAGGGCTGGGCATCAGCTG

GCTGGGGCTGCGCTCACTGAGGGAACTGGGCAGTGGACTGGCCCTCATCCACCAT

AACACCCACCTCTGCTTCGTGCACACGGTGCCCTGGGACCAGCTCTTTCGGAACCC

GCACCAAGCTCTGCTCCACACTGCCAACCGGCCAGAGGACGAGTGTGTGGGCGAG

GGCCTGGCCTGCCACCAGCTGTGCGCCCGAGGG.
```

In one embodiment, complete EC2 human her2/neu fragment spans from 907-1504 bp of the human her2/neu gene and is set forth in (SEQ ID NO: 55).

```
                                         (SEQ ID NO: 55)
TACCTTTCTACGGACGTGGGATCCTGCACCCTCGTCTGCCCCCTGCACAACCAAG

AGGTGACAGCAGAGGATGGAACACAGCGGTGTGAGAAGTGCAGCAAGCCCTGTG

CCCGAGTGTGCTATGGTCTGGGCATGGAGCACTTGCGAGAGGTGAGGGCAGTTAC

CAGTGCCAATATCCAGGAGTTTGCTGGCTGCAAGAAGATCTTTGGGAGCCTGGCA

TTTCTGCCGGAGAGCTTTGATGGGGACCCAGCCTCCAACACTGCCCCGCTCCAGC

CAGAGCAGCTCCAAGTGTTTGAGACTCTGGAAGAGATCACAGGTTACCTATACAT

CTCAGCATGGCCGGACAGCCTGCCTGACCTCAGCGTCTTCCAGAACCTGCAAGTA

ATCCGGGGACGAATTCTGCACAATGGCGCCTACTCGCTGACCCTGCAAGGGCTGG

GCATCAGCTGGCTGGGGCTGCGCTCACTGAGGGAACTGGGCAGTGGACTGGCCCT

CATCCACCATAACACCCACCTCTGCTTCGTGCACACGGTGCCCTGGGACCAGCTC

TTTCGGAACCCGCACCAAGCTCTGCTCCACACTGCCAACCGGCCAGAG.
```

In another embodiment, the nucleic acid sequence encoding the human her2/neu IC1 fragment implemented into the chimera is set forth in (SEQ ID NO: 52).

(SEQ ID NO: 52)
CAGCAGAAGATCCGGAAGTACACGATGCGGAGACTGCTGCAGGAAACGGAGCTG

GTGGAGCCGCTGACACCTAGCGGAGCGATGCCCAACCAGGCGCAGATGCGGATC

CTGAAAGAGACGGAGCTGAGGAAGGTGAAGGTGCTTGGATCTGGCGCTTTTGGC

ACAGTCTACAAGGGCATCTGGATCCCTGATGGGGAGAATGTGAAAATTCCAGTG

GCCATCAAAGTGTTGAGGGAAAACACATCCCCCAAAGCCAACAAAGAAATCTTA

GACGAAGCATACGTGATGGCTGGTGTGGGCTCCCCATATGTCTCCCGCCTTCTGG

GCATCTGCCTGACATCCACGGTGCAGCTGGTGACACAGCTTATGCCCTATGGCTG

CCTCTTAGACT.

In another embodiment, the nucleic acid sequence encoding the complete human her2/neu IC1 fragment spans from 2034-3243 of the human her2/neu gene and is set forth in (SEQ ID NO: 56).

(SEQ ID NO: 56)
CAGCAGAAGATCCGGAAGTACACGATGCGGAGACTGCTGCAGGAAACGGAGCTG

GTGGAGCCGCTGACACCTAGCGGAGCGATGCCCAACCAGGCGCAGATGCGGATC

CTGAAAGAGACGGAGCTGAGGAAGGTGAAGGTGCTTGGATCTGGCGCTTTTGGC

ACAGTCTACAAGGGCATCTGGATCCCTGATGGGGAGAATGTGAAAATTCCAGTG

GCCATCAAAGTGTTGAGGGAAAACACATCCCCCAAAGCCAACAAAGAAATCTTA

GACGAAGCATACGTGATGGCTGGTGTGGGCTCCCCATATGTCTCCCGCCTTCTGG

GCATCTGCCTGACATCCACGGTGCAGCTGGTGACACAGCTTATGCCCTATGGCTG

CCTCTTAGACCATGTCCGGGAAAACCGCGGACGCCTGGGCTCCCAGGACCTGCTG

AACTGGTGTATGCAGATTGCCAAGGGGATGAGCTACCTGGAGGATGTGCGGCTC

GTACACAGGGACTTGGCCGCTCGGAACGTGCTGGTCAAGAGTCCCAACCATGTCA

AAATTACAGACTTCGGGCTGGCTCGGCTGCTGGACATTGACGAGACAGAGTACCA

TGCAGATGGGGGCAAGGTGCCCATCAAGTGGATGGCGCTGGAGTCCATTCTCCGC

CGGCGGTTCACCCACCAGAGTGATGTGTGGAGTTATGGTGTGACTGTGTGGGAGC

TGATGACTTTTGGGGCCAAACCTTACGATGGGATCCCAGCCCGGGAGATCCCTGA

CCTGCTGGAAAAGGGGGAGCGGCTGCCCCAGCCCCCCATCTGCACCATTGATGTC

TACATGATCATGGTCAAATGTTGGATGATTGACTCTGAATGTCGGCCAAGATTCC

GGGAGTTGGTGTCTGAATTCTCCCGCATGGCCAGGGACCCCCAGCGCTTTGTGGT

CATCCAGAATGAGGACTTGGGCCCAGCCAGTCCCTTGGACAGCACCTTCTACCGC

TCACTGCTGGAGGACGATGACATGGGGGACCTGGTGGATGCTGAGGAGTATCTG

GTACCCCAGCAGGGCTTCTTCTGTCCAGACCCTGCCCCGGGCGCTGGGGGCATGG

TCCACCACAGGCACCGCAGCTCATCTACCAGGAGTGGCGGTGGGGACCTGACACT

AGGGCTGGAGCCCTCTGAAGAGGAGGCCCCCAGGTCTCCACTGGCACCCTCCGA

AGGGGCT.

The LLO utilized in the methods and compositions provided herein is, in one embodiment, a *Listeria* LLO. In one embodiment, the *Listeria* from which the LLO is derived is *Listeria monocytogenes* (LM). In another embodiment, the *Listeria* is *Listeria ivanovii*. In another embodiment, the *Listeria* is *Listeria welshimeri*. In another embodiment, the *Listeria* is *Listeria seeligeri*. In another embodiment, the LLO protein is a non-Listerial LLO protein. In another embodiment, the LLO protein is a synthetic LLO protein. In another embodiment it is a recombinant LLO protein.

In one embodiment, the LLO protein is encoded by the following nucleic acid sequence set forth in (SEQ ID NO: 3)

(SEQ ID NO: 3)
atgaaaaaaataatgctagtttttattacacttatattagttagtctacc aattgcgcaacaaactgaagcaaaggatgcatctgcattcaataaagaaa attcaatttcatccatggcaccaccagcatctccgcctgcaagtcctaag acgccaatcgaaagaaacacgcggatgaaatcgataagtatatacaagg attggattacaataaaaacaatgtattagtataccacggagatgcagtga caaatgtgccgccaagaaaaggttacaaagatggaaatgaatatattgtt gtggagaaaagaagaaatccatcaatcaaaataatgcagacattcaagt tgtgaatgcaatttcgagcctaacctatccaggtgctctcgtaaaagcga attcggaattagtagaaaatcaaccagatgttctccctgtaaaacgtgat tcattaacactcagcattgatttgccaggtatgactaatcaagacaataa aatagttgtaaaaaatgccactaaatcaaacgttaacaacgcagtaaata cattagtggaaagatggaatgaaaaatatgctcaagcttatccaaatgta agtgcaaaaattgattatgatgacgaaatggcttacagtgaatcacaatt aattgcgaaatttggtacagcatttaaagctgtaaataatagcttgaatg taaacttcggcgcaatcagtgaagggaaatgcaagaagaagtcattagt tttaaacaaatttactataacgtgaatgttaatgaacctacaagaccttc cagattttcggcaaagctgttactaaagagcagttgcaagcgcttggag tgaatgcagaaaatcctcctgcatatatctcaagtgtggcgtatggccgt caagtttatttgaaattatcaactaattcccatagtactaaagtaaaagc tgctttgatgctgccgtaagcggaaaatctgtctcaggtgatgtagaact aacaaatatcatcaaaaattcttccttcaaagccgtaatttacggaggtt ccgcaaaagatgaagttcaaatcatcgacggcaacctcggagacttacgc gatattttgaaaaaaggcgctacttttaatcgagaaacaccaggagttcc cattgcttatacaacaaacttcctaaaagacaatgaattagctgttatta aaaacaactcagaatatattgaaacaacttcaaaagcttatacagatgga aaaattaacatcgatcactctggaggatacgttgctcaattcaacatttc ttgggatgaagtaaattatgat.

In another embodiment, the LLO protein has the sequence SEQ ID NO: 4

(SEQ ID NO: 4)
M K K I M L V F I T L I L V S L P I A Q Q T E A K

D A S A F N K E N S I S S M A P P A S P P A S P K

T P I E K K H A D E I D K Y I Q G L D Y N K N N V

L V Y H G D A V T N V P P R K G Y K D G N E Y I V

V E K K K K S I N Q N N A D I Q V V N A I S S L T

Y P G A L V K A N S E L V E N Q P D V L P V K R D

S L T L S I D L P G M T N Q D N K I V V K N A T K

-continued
S N V N N A V N T L V E R W N E K Y A Q A Y P N V

S A K I D Y D D E M A Y S E S Q L I A K F G T A F

K A V N N S L N V N F G A I S E G K M Q E E V I S

F K Q I Y Y N V N V N E P T R P S R F F G K A V T

K E Q L Q A L G V N A E N P P A Y I S S V A Y G R

Q V Y L K L S T N S H S T K V K A A F D A A V S G

K S V S G D V E L T N I I K N S S F K A V I Y G G

S A K D E V Q I I D G N L G D L R D I L K K G A T

F N R E T P G V P I A Y T T N F L K D N E L A V I

K N N S E Y I E T T S K A Y T D G K I N I D H S G

G Y V A Q F N I S W D E V N Y D

The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein has a sequence set forth in GenBank Accession No. DQ054588, DQ054589, AY878649, U25452, or U25452. In another embodiment, the LLO protein is a variant of an LLO protein. In another embodiment, the LLO protein is a homologue of an LLO protein. Each possibility represents a separate embodiment of the present invention.

In another embodiment, "truncated LLO" or "tLLO" refers to a fragment of LLO that comprises the PEST-like domain. In another embodiment, the terms refer to an LLO fragment that does not contain the activation domain at the amino terminus and does not include cystine 484. In another embodiment, the LLO fragment consists of a PEST sequence. In another embodiment, the LLO fragment comprises a PEST sequence. In another embodiment, the LLO fragment consists of about the first 400 to 441 amino acids of the 529 amino acid full-length LLO protein. In another embodiment, the LLO fragment is a non-hemolytic form of the LLO protein.

In another embodiment of methods and compositions of the present invention, a polypeptide encoded by a nucleic acid sequence of methods and compositions of the present invention is a fusion protein comprising the chimeric Her-2/neu antigen and an additional polypeptide, where in another embodiment, the fusion protein comprises, inter alia, an LM non-hemolytic LLO protein (Examples herein).

In one embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300.

In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425. Each possibility represents a separate embodiment of the present invention.

In another embodiment, a fusion protein of methods and compositions of the present invention comprises a PEST sequence, either from an LLO protein or from another organism, e.g. a prokaryotic organism.

The PEST-like AA sequence has, in another embodiment, a sequence selected from SEQ ID NO: 5-9. In another embodiment, the PEST-like sequence is a PEST-like sequence from the LM ActA protein. In another embodiment, the PEST-like sequence is KTEEQPSEVNTGPR (SEQ ID NO: 5), KASVTDTSEGDLDSSMQSADESTPQPLK (SEQ ID NO: 6), KNEEVNASDFPPPPPTDEELR (SEQ ID NO: 7), or RGGIPTSEEFSSLNSGDFTDDENSETTEEEIDR (SEQ ID NO: 8). In another embodiment, the PEST-like sequence is from Streptolysin O protein of *Streptococcus* sp. In another embodiment, the PEST-like sequence is from *Streptococcus pyogenes* Streptolysin O, e.g. KQNTASTETTTTNEQPK (SEQ ID NO: 9) at AA 35-51. In another embodiment, the PEST-like sequence is from *Streptococcus equisimilis* Streptolysin O, e.g. KQNTANTETTTTNEQPK (SEQ ID NO: 10) at AA 38-54. In another embodiment, the PEST-like sequence is another PEST-like AA sequence derived from a prokaryotic organism. In another embodiment, the PEST-like sequence is any other PEST-like sequence known in the art. Each possibility represents a separate embodiment of the present invention.

In one embodiment, fusion of an antigen to the PEST-like sequence of LM enhanced cell mediated and anti-tumor immunity of the antigen. Thus, fusion of an antigen to other PEST-like sequences derived from other prokaryotic organisms will also enhance immunogenicity of the antigen. PEST-like sequence of other prokaryotic organism can be identified in accordance with methods such as described by, for example Rechsteiner and Rogers (1996, Trends Biochem. Sci. 21:267-271) for LM. Alternatively, PEST-like AA sequences from other prokaryotic organisms can also be identified based by this method. Other prokaryotic organisms wherein PEST-like AA sequences would be expected to include, but are not limited to, other *Listeria* species. In another embodiment, the PEST-like sequence is embedded within the antigenic protein. Thus, in another embodiment, "fusion" refers to an antigenic protein comprising both the antigen and the PEST-like amino acid sequence either linked at one end of the antigen or embedded within the antigen.

In another embodiment, provided herein is a vaccine comprising a recombinant polypeptide of the present invention. In another embodiment, provided herein is a vaccine consisting of a recombinant polypeptide of the present invention.

In another embodiment, provided herein is a nucleotide molecule encoding a recombinant polypeptide of the present invention. In another embodiment, provided herein is a vaccine comprising the nucleotide molecule.

In another embodiment, provided herein is a nucleotide molecule encoding a recombinant polypeptide of the present invention.

In another embodiment, provided herein is a recombinant polypeptide encoded by the nucleotide molecule of the present invention.

In another embodiment, provided herein is a vaccine comprising a nucleotide molecule or recombinant polypeptide of the present invention.

In another embodiment, provided herein is an immunogenic composition comprising a nucleotide molecule or recombinant polypeptide of the present invention.

In another embodiment, provided herein is a vector comprising a nucleotide molecule or recombinant polypeptide of the present invention.

In another embodiment, provided herein is a recombinant form of *Listeria* comprising a nucleotide molecule of the present invention.

In another embodiment, provided herein is a vaccine comprising a recombinant form of *Listeria* of the present invention.

In another embodiment, provided herein is a culture of a recombinant form of *Listeria* of the present invention.

In one embodiment, the vaccine for use in the methods of the present invention comprises a recombinant *Listeria monocytogenes*, in any form or embodiment as described herein. In one embodiment, the vaccine for use in the present invention consists of a recombinant *Listeria monocytogenes* of the present invention, in any form or embodiment as described herein. In another embodiment, the vaccine for use in the methods of the present invention consists essentially of a recombinant *Listeria monocytogenes* of the present invention, in any form or embodiment as described herein. In one embodiment, the term "comprise" refers to the inclusion of a recombinant *Listeria monocytogenes* in the vaccine, as well as inclusion of other vaccines or treatments that may be known in the art. In another embodiment, the term "consisting essentially of" refers to a vaccine, whose functional component is the recombinant *Listeria monocytogenes*, however, other components of the vaccine may be included that are not involved directly in the therapeutic effect of the vaccine and may, for example, refer to components which facilitate the effect of the recombinant *Listeria monocytogenes* (e.g. stabilizing, preserving, etc.). In another embodiment, the term "consisting" refers to a vaccine, which contains the recombinant *Listeria monocytogenes*.

In another embodiment, the methods of the present invention comprise the step of administering a recombinant *Listeria monocytogenes*, in any form or embodiment as described herein. In one embodiment, the methods of the present invention consist of the step of administering a recombinant *Listeria monocytogenes* of the present invention, in any form or embodiment as described herein. In another embodiment, the methods of the present invention consist essentially of the step of administering a recombinant *Listeria monocytogenes* of the present invention, in any form or embodiment as described herein. In one embodiment, the term "comprise" refers to the inclusion of the step of administering a recombinant *Listeria monocytogenes* in the methods, as well as inclusion of other methods or treatments that may be known in the art. In another embodiment, the term "consisting essentially of" refers to a methods, whose functional component is the administration of recombinant *Listeria monocytogenes*, however, other steps of the methods may be included that are not involved directly in the therapeutic effect of the methods and may, for example, refer to steps which facilitate the effect of the administration of recombinant *Listeria monocytogenes*. In one embodiment, the term "consisting" refers to a method of administering recombinant *Listeria monocytogenes* with no additional steps.

In another embodiment, the *Listeria* of methods and compositions of the present invention is *Listeria monocytogenes*. In another embodiment, the *Listeria* is *Listeria* ivanovii. In another embodiment, the *Listeria* is *Listeria welshimeri*. In another embodiment, the *Listeria* is *Listeria seeligeri*. Each type of *Listeria* represents a separate embodiment of the present invention.

In one embodiment, the *Listeria* strain of the methods and compositions of the present invention is the ADXS31-164 strain. In another embodiment, ADXS31-164 stimulates the secretion of IFN-γ by the splenocytes from wild type FVB/N mice. Further, the data presented herein show that ADXS31-164 is able to elicit anti-Her2/neu specific immune responses to human epitopes that are located at different domains of the targeted antigen.

In another embodiment, the present invention provides a recombinant form of *Listeria* comprising a nucleotide molecule encoding a Her-2 chimeric protein or a fragment thereof.

In one embodiment, the present invention provides a method of inducing an anti-Her-2 immune response in a subject, comprising administering to the subject a recombinant polypeptide comprising an N-terminal fragment of a LLO protein fused to a Her-2 chimeric protein or fused to a fragment thereof, thereby inducing an anti-Her-2 immune response in a subject.

In one embodiment, the fusion protein of methods and compositions of the present invention comprises an LLO signal sequence from LLO. In another embodiment, the two molecules of the protein (the LLO fragment and the antigen) are joined directly. In another embodiment, the two molecules are joined by a short spacer peptide, consisting of one or more amino acids. In one embodiment, the spacer has no specific biological activity other than to join the proteins or to preserve some minimum distance or other spatial relationship between them. In another embodiment, the constituent amino acids of the spacer are selected to influence some property of the molecule such as the folding, net charge, or hydrophobicity. In another embodiment, the two molecules of the protein (the LLO fragment and the antigen) are synthesized separately or unfused. In another embodiment, the two molecules of the protein are synthesized separately from the same nucleic acid. In yet another embodiment, the two molecules are individually synthesized from separate nucleic acids. Each possibility represents a separate embodiment of the present invention.

In another embodiment, provided herein is a method of inducing an anti-Her-2 immune response in a subject, comprising administering to the subject a recombinant nucleotide encoding a recombinant polypeptide comprising an N-terminal fragment of a LLO protein fused to a Her-2 chimeric protein or fused to a fragment thereof, thereby inducing an anti-Her-2 immune response in a subject.

In one embodiment, provided herein is a method of eliciting an enhanced immune response to a Her2/neu-expressing tumor in a subject, where in another embodiment the method comprises administering to the subject a composition comprising the recombinant *Listeria* vaccine strain provided herein. In another embodiment, the immune response against the Her-2-expressing tumor comprises an immune response to a subdominant epitope of the Her-2 protein. In another embodiment, the immune response against the Her-2-expressing tumor comprises an immune response to several subdominant epitopes of the Her-2 protein. In another embodiment, the immune response against the Her-2-expressing tumor comprises an immune response to at least 1-5 subdominant epitopes of the Her-2 protein. In another embodiment, the immune response against the Her-2-expressing tumor comprises an immune response to at least 1-10 subdominant epitopes of the Her-2 protein. In another embodiment, the immune response against the Her-2-expressing tumor comprises an immune response to at least 1-17 subdominant epitopes of the Her-2 protein. In another embodiment, the immune response against the Her-2-expressing tumor comprises an immune response to at least 17 subdominant epitopes of the Her-2 protein.

Point mutations or amino-acid deletions in the oncogenic protein Her2/neu, have been reported to mediate treatment of resistant tumor cells, when these tumors have been targeted by small fragment *Listeria*-based vaccines or trastuzumab (a monoclonal antibody against an epitope located at the extracellular domain of the Her2/neu antigen). Described herein is a chimeric Her2/neu based composition which harbors two of the extracellular and one intracellular fragments of Her2/neu antigen showing clusters of MHC-class I epitopes of the oncogene. This chimeric protein, which harbors 3 H2Dq and at least 17 of the mapped human MHC-class I epitopes of the Her2/neu antigen was fused to the first 441 amino acids of the *Listeria-monocytogenes* listeriolysin O protein and expressed and secreted by the *Listeria monocytogenes* attenuated strain LmddA.

Previous reports have shown that when Her2/neu transgenic mice were immunized with *Listeria*-based vaccines expressing and secreting small fragments of the Her2/neu antigen separately (each of which harbored only one H2Dq epitope of the Her2/neu oncogene), Her2/neu over-expressing tumors could escape due to mutations in those epitopes of the Her2/neu antigen targeted by each vaccine (see Singh R, Paterson Y Immunoediting sculpts tumor epitopes during immunotherapy. Cancer Res 2007; 67: 1887-92). Demonstrated herein is the unexpected result that when three or more epitopes of the Her2/neu protein are incorporated in a chimeric vaccine, it can eliminate the selection and escape of these tumors by escape mutations Immunization with the novel Her2/neu chimeric *Listeria* vaccines did not result in any escape mutations that could be associated with point mutations or amino acid deletions in the Her2/neu antigen (see Example 4 herein).

In one embodiment, provided herein is a method of engineering a *Listeria* vaccine strain to express a Her-2 chimeric protein or recombinant polypeptide expressing the chimeric protein, the method comprising transforming a *Listeria* strain with a nucleic acid molecule. In another embodiment, the nucleic acid molecule comprises a first open reading frame encoding a polypeptide, wherein the polypeptide comprises a Her2/neu chimeric antigen. In another embodiment, the nucleic acid molecule further comprises a second open reading frame encoding a metabolic enzyme, and wherein said metabolic enzyme complements an endogenous gene that is lacking in the chromosome of the recombinant *Listeria* strain, thereby engineering a *Listeria* vaccine strain to express a Her-2 chimeric protein.

In one embodiment, the methods and compositions provided herein further comprise an adjuvant, where in another embodiment, the adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

In one embodiment, attenuated *Listeria* strains, such as LM delta-actA mutant (Brundage et al, 1993, Proc. Natl. Acad. Sci., USA, 90:11890-11894), *L. monocytogenes* delta-plcA (Camilli et al, 1991, J. Exp. Med., 173:751-754), or delta-ActA, delta INL-b (Brockstedt et 5 al, 2004, PNAS, 101: 13832-13837) are used in the present invention. In another embodiment, attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids (Alexander et al, 1993, Infection and Immunity 10 61:2245-2248) and mutant for the formation of lipoteichoic acids (Abachin et al, 2002, Mol. Microbiol. 43:1-14) and those attenuated by a lack of a virulence gene (see examples herein).

In another embodiment, the nucleic acid molecule of methods and compositions of the present invention is operably linked to a promoter/regulatory sequence. In another embodiment, the first open reading frame of methods and compositions of the present invention is operably linked to a promoter/regulatory sequence. In another embodiment, the second open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

The skilled artisan, when equipped with the present disclosure and the methods provided herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the pUC series. In another embodiment, non-essential DNA sequences (e.g. antibiotic resistance genes) are removed. Each possibility represents a separate embodiment of the present invention. In another embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art.

Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the *Listeria* vaccine strain of the present invention is transformed by electroporation. Each method represents a separate embodiment of the present invention.

In another embodiment, conjugation is used to introduce genetic material and/or plasmids into bacteria. Methods for conjugation are well known in the art, and are described, for example, in Nikodinovic J et al. (A second generation snp-derived *Escherichia coli*-*Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102 (35):12554-9). Each method represents a separate embodiment of the present invention.

"Transforming," in one embodiment, is used identically with the term "transfecting," and refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the present invention.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of 5 bacteriophage lambda (PL and PR), the trp, recA, lacZ, lad, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter, the Listerial hly promoter, the Listerial p60 promoter and the Listerial ActA promoter (GenBank Acc. No. NC_003210) or fragments thereof.

In another embodiment, a plasmid of methods and compositions of the present invention comprises a gene encoding a fusion protein. In another embodiment, subsequences are cloned and the appropriate subsequences cleaved using appropriate restriction enzymes. The fragments are then, in another embodiment, ligated to produce the desired DNA sequence. In another embodiment, DNA encoding the antigen is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

In another embodiment, the present invention further comprises a phage based chromosomal integration system for clinical applications. A host strain that is auxotrophic for essential enzymes, including, but not limited to, d-alanine racemase will be used, for example Lmdal(−)dat(−). In another embodiment, in order to avoid a "phage curing step," a phage integration system based on PSA is used (Lauer, et al., 2002 J Bacteriol, 184:4177-4186). This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain will be complemented.

The recombinant proteins of the present invention are synthesized, in another embodiment, using recombinant DNA methodology. This involves, in one embodiment, creating a DNA sequence that encodes the fusion protein, placing the DNA in an expression cassette, such as the plasmid of the present invention, under the control of a particular promoter/regulatory element, and expressing the protein. DNA encoding the fusion protein (e.g. non-hemolytic LLO/antigen) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 15 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then ligated to produce the desired DNA sequence.

In another embodiment, DNA encoding the fusion protein or the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning. The same is repeated for the isolated nucleic acid encoding an antigen. Ligation of the non-hemolytic LLO and antigen sequences and insertion into a plasmid or vector produces a vector encoding non-hemolytic LLO joined to a terminus of the antigen. The two molecules are joined either directly or by a short spacer introduced by the restriction site.

In another embodiment, the molecules are separated by a peptide spacer consisting of one or more amino acids, generally the spacer will have no specific biological activity other than to join the proteins or to preserve some minimum distance or other spatial relationship between them. In another embodiment, the constituent AA of the spacer are selected to influence some property of the molecule such as the folding, net charge, or hydrophobicity. In another embodiment, the nucleic acid sequences encoding the fusion or recombinant proteins are transformed into a variety of host cells, including *E. coli*, other bacterial hosts, such as *Listeria*, yeast, and various higher eukaryotic cells such as the COS, CHO and HeLa cells lines and myeloma cell lines. The recombinant fusion protein gene will be operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e g immunoglobulin genes, SV40, cytomegalovirus, etc., and a polyadenylation sequence. In another embodiment, the sequences include splice donor and acceptor sequences.

In one embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In another embodiment, in order to select for an auxotrophic bacterium comprising the plasmid, transformed auxotrophic bacteria are grown on a media that will select for expression of the amino acid metabolism gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the Listeria vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, provided herein is a method of impeding a growth of a Her-2-expressing tumor in a subject, wherein and in another embodiment, the method comprises the step of administering to the subject a composition comprising the recombinant Listeria vaccine strain described herein.

In another embodiment, provided herein is a method of impeding a growth of a Her-2-expressing tumor in a subject, wherein and in another embodiment, the method comprises the step of administering to the subject a composition comprising the recombinant Listeria vaccine strain described herein.

In another embodiment, provided herein is a method of eliciting an enhanced immune response to a Her2/neu-expressing tumor in a subject, wherein and in another embodiment, the method comprises the step of administering to the subject a composition comprising the recombinant Listeria vaccine strain described herein. In yet another embodiment, the immune response against the Her2/neu-expressing tumor comprises an immune response to at least one subdominant epitope of the Her2/neu protein.

In one embodiment, provided herein is a method of preventing an escape mutation in the treatment of Her2/neu over-expressing tumors, wherein and in another embodiment, the method comprises the step of administering to said subject a composition comprising the recombinant Listeria vaccine strain provided herein.

In another embodiment, provided herein is a method of preventing the onset of a Her2/neu antigen-expressing tumor in a subject, wherein and in another embodiment, the method comprises the step of administering to the subject a composition comprising the recombinant Listeria vaccine strain provided herein.

In one embodiment, provided herein is a method of decreasing the frequency of intra-tumoral T regulatory cells, wherein and in another embodiment, the method comprises the step of administering to the subject a composition comprising the recombinant Listeria vaccine strain provided herein.

In another embodiment, provided herein is a method of decreasing the frequency of intra-tumoral T regulatory cells, wherein and in another embodiment, the method comprises the step of administering to the subject a composition comprising the recombinant Listeria vaccine strain provided herein.

In one embodiment, provided herein is a method of decreasing the frequency of intra-tumoral myeloid derived suppressor cells, wherein and in another embodiment, the method comprises the step of administering to the subject a composition comprising the recombinant Listeria vaccine strain provided herein.

In another embodiment, provided herein is a method of decreasing the frequency of myeloid derived suppressor cells, wherein and in another embodiment, the method comprises the step of administering to the subject a composition comprising the recombinant Listeria vaccine strain provided herein.

In one embodiment, provided herein a method of preventing the formation of a Her2/neu-expressing tumor in a subject, wherein and in another embodiment, the method comprises the step of administering to the subject a composition comprising the recombinant Listeria vaccine strain provided herein.

In another embodiment, provided herein is a method of preventing the formation of a Her2/neu-expressing tumor in a subject, wherein and in another embodiment, the method comprises the step of administering to the subject a composition comprising the recombinant Listeria vaccine strain the provided herein.

In one embodiment, provided herein is a method of treating a Her2/neu-expressing tumor in a subject, wherein and in another embodiment, the method comprises the step of administering to the subject a composition comprising the recombinant Listeria vaccine strain provided herein.

In one embodiment, provided herein is a method of administering the composition of the present invention. In another embodiment, provided herein is a method of administering the vaccine of the present invention. In another embodiment, provided herein is a method of administering the recombinant polypeptide or recombinant nucleotide of the present invention. In another embodiment, the step of administering the composition, vaccine, recombinant polypeptide or recombinant nucleotide of the present invention is performed with an attenuated recombinant form of Listeria comprising the composition, vaccine, recombinant nucleotide or expressing the recombinant polypeptide, each in its own discrete embodiment. In another embodiment, the administering is performed with a different attenuated bacterial vector. In another embodiment, the administering is performed with a DNA vaccine (e.g. a naked DNA vaccine). In another embodiment, administration of a recombinant polypeptide of the present invention is performed by producing the protein recombinantly, then administering the recombinant protein to a subject. Each possibility represents a separate embodiment of the present invention.

In another embodiment, the immune response elicited by methods and compositions of the present invention comprises a $CD8^+$ T cell-mediated response. In another embodiment, the immune response consists primarily of a $CD8^+$ T cell-mediated response. In another embodiment, the only detectable component of the immune response is a $CD8^+$ T cell-mediated response.

In another embodiment, the immune response elicited by methods and compositions provided herein comprises a $CD4^+$ T cell-mediated response. In another embodiment, the immune response consists primarily of a $CD4^+$ T cell-mediated response. In another embodiment, the only detectable component of the immune response is a $CD4^+$ T cell-mediated response. In another embodiment, the $CD4^+$ T cell-mediated response is accompanied by a measurable antibody response against the antigen. In another embodiment, the $CD4^+$ T cell-mediated response is not accompanied by a measurable antibody response against the antigen.

In another embodiment, the present invention provides a method of inducing a $CD8^+$ T cell-mediated immune response in a subject against a subdominant $CD8^+$ T cell epitope of an antigen, comprising the steps of (a) fusing a nucleotide molecule encoding the Her2-neu chimeric antigen or a fragment thereof to a nucleotide molecule encoding an N-terminal fragment of a LLO protein, thereby creating a recombinant nucleotide encoding an LLO-antigen fusion protein; and (b) administering the recombinant nucleotide or the LLO-antigen fusion to the subject; thereby inducing a $CD8^+$ T cell-mediated immune response against a subdominant $CD8^+$ T cell epitope of an antigen.

In one embodiment, provided herein is a method of increasing intratumoral ratio of CD8+/T regulatory cells, wherein and in another embodiment, the method comprises the step of administering to the subject a composition comprising the recombinant polypeptide, recombinant *Listeria*, or recombinant vector of the present invention.

In another embodiment, provided herein is a method of increasing intratumoral ratio of CD8+/T regulatory cells, wherein and in another embodiment, the method comprises the step of administering to the subject a composition comprising the recombinant polypeptide, recombinant *Listeria*, or recombinant vector of the present invention.

In another embodiment, the immune response elicited by the methods and compositions provided herein comprises an immune response to at least one subdominant epitope of the antigen. In another embodiment, the immune response does not comprise an immune response to a subdominant epitope. In another embodiment, the immune response consists primarily of an immune response to at least one subdominant epitope. In another embodiment, the only measurable component of the immune response is an immune response to at least one subdominant epitope. Each type of immune response represents a separate embodiment of the present invention.

Methods of measuring immune responses are well known in the art, and include, e.g. measuring suppression of tumor growth, flow cytometry, target cell lysis assays (e.g. chromium release assay), the use of tetramers, and others. Each method represents a separate embodiment of the present invention.

In another embodiment, the present invention provides a method of impeding a growth of a Her-2-expressing tumor in a subject, wherein and in another embodiment, the method comprises administering to the subject a recombinant polypeptide comprising an N-terminal fragment of a LLO protein fused to the Her-2 chimeric protein or a fragment thereof or a recombinant nucleotide encoding the recombinant polypeptide, wherein the subject mounts an immune response against the Her-2-expressing tumor, thereby impeding a growth of a Her-2-expressing tumor in a subject.

In another embodiment, the present invention provides a method of improving an antigenicity of a Her-2 chimeric protein, wherein and in another embodiment, the method comprises the step of fusing a nucleotide encoding an N-terminal fragment of a LLO protein to a nucleotide encoding the Her-2 protein or a fragment thereof to create a recombinant nucleotide, thereby improving an antigenicity of a Her-2 chimeric protein.

In another embodiment, provided herein is a method of improving an antigenicity of a Her-2 chimeric protein, wherein and in another embodiment, the method comprises engineering a *Listeria* strain to express the recombinant nucleotide. In another embodiment, a different bacterial vector is used to express the recombinant nucleotide. In another embodiment, the bacterial vector is attenuated. In another embodiment, a DNA vaccine (e.g. a naked DNA vaccine) is used to express the recombinant nucleotide. In another embodiment, administration of the LLO-Her-2 chimera fusion peptide encoded by the nucleotide is performed by producing the protein recombinantly, then administering the recombinant protein to a subject. Each possibility represents a separate embodiment of the present invention.

In one embodiment, the present invention provides a method for "epitope spreading" of a tumor. In another embodiment, the immunization using the compositions and methods provided herein induce epitope spreading onto other tumors bearing antigens other than the antigen carried in the vaccine of the present invention.

In another embodiment, the dominant epitope or subdominant epitope is dominant or subdominant, respectively, in the subject being treated. In another embodiment, the dominant epitope or subdominant epitope is dominant or subdominant in a population being treated.

In one embodiment, provided herein is a method of treating, suppressing, or inhibiting a cancer or a tumor growth in a subject by epitope spreading wherein and in another embodiment, said cancer is associated with expression of an antigen or fragment thereof comprised in the composition of the present invention. In another embodiment, the method comprises administering to said subject a composition comprising the recombinant polypeptide, recombinant *Listeria*, or recombinant vector of the present invention. In yet another embodiment, the subject mounts an immune response against the antigen-expressing cancer or the antigen-expressing tumor, thereby treating, suppressing, or inhibiting a cancer or a tumor growth in a subject.

"Dominant $CD8^+$ T cell epitope," in one embodiment, refers to an epitope that is recognized by over 30% of the antigen-specific $CD8^+$ T cells that are elicited by vaccination, infection, or a malignant growth with a protein or a pathogen or cancer cell containing the protein. In another embodiment, the term refers to an epitope recognized by over 35% of the antigen-specific $CD8^+$ T cells that are elicited thereby. In another embodiment, the term refers to an epitope recognized by over 40% of the antigen-specific $CD8^+$ T cells. In another embodiment, the term refers to an epitope recognized by over 45% of the antigen-specific $CD8^+$ T cells. In another embodiment, the term refers to an epitope recognized by over 50% of the antigen-specific $CD8^+$ T cells. In another embodiment, the term refers to an epitope recognized by over 55% of the antigen-specific $CD8^+$ T cells. In another embodiment, the term refers to an epitope recognized by over 60% of the antigen-specific $CD8^+$ T cells. In another embodiment, the term refers to an epitope recognized by over 65% of the antigen-specific $CD8^+$ T cells. In another embodiment, the term refers to an epitope recognized by over 70% of the antigen-specific $CD8^+$ T cells. In another embodiment, the term refers to an epitope recognized by over 75% of the antigen-specific $CD8^+$ T cells. In another embodiment, the term refers to an epitope recognized by over 80% of the antigen-specific $CD8^+$ T cells. In another embodiment, the term refers to an epitope recognized by over 85% of the antigen-specific $CD8^+$ T cells. In another embodiment, the term refers to an epitope recognized by over 90% of the antigen-specific $CD8^+$ T cells. In another embodiment, the term refers to an epitope recognized by over 95% of the antigen-specific $CD8^+$ T cells. In another embodiment, the term refers to an epitope recognized by over 96% of the antigen-specific $CD8^+$ T cells. In another embodiment, the term refers to an epitope recognized by over 97% of the antigen-specific $CD8^+$ T cells. In another embodiment, the term refers to an epitope recognized by over 98% of the antigen-specific $CD8^+$ T cells.

"Subdominant $CD8^+$ T cell epitope," in one embodiment, refers to an epitope recognized by fewer than 30% of the antigen-specific $CD8^+$ T cells that are elicited by vaccination, infection, or a malignant growth with a protein or a pathogen or cancer cell containing the protein. In another embodiment, the term refers to an epitope recognized by fewer than 28% of the antigen-specific $CD8^+$ T cells. In another embodiment, the term refers to an epitope recognized by over 26% of the antigen-specific $CD8^+$ T cells. In another embodiment, the term refers to an epitope recognized by fewer than 24% of the antigen-specific CD8$^+$ T cells. In another embodiment, the term refers to an epitope recognized by over 22% of the antigen-specific CD8$^+$ T cells. In another embodiment, the term refers to an epitope recognized by fewer than 20% of the antigen-specific CD8$^+$ T cells. In another embodiment, the term refers to an epitope recognized by over 18% of the antigen-specific CD8$^+$ T cells. In another embodiment, the term refers to an epitope recognized by fewer than 16% of the antigen-specific CD8$^+$ T cells. In another embodiment, the term refers to an epitope recognized by over 14% of the antigen-specific CD8$^+$ T cells. In another embodiment, the term refers to an epitope recognized by over 12% of the antigen-specific CD8$^+$ T cells. In another embodiment, the term refers to an epitope recognized by fewer than 10% of the antigen-specific CD8$^+$ T cells. In another embodiment, the term refers to an epitope recognized by over 8% of the antigen-specific CD8$^+$ T cells. In another embodiment, the term refers to an epitope recognized by fewer than 6% of the antigen-specific CD8$^+$ T cells. In another embodiment, the term refers to an epitope recognized by fewer than 5% of the antigen-specific CD8$^+$ T cells. In another embodiment, the term refers to an epitope recognized by over 4% of the antigen-specific CD8$^+$ T cells. In another embodiment, the term refers to an epitope recognized by fewer than 3% of the antigen-specific CD8$^+$ T cells. In another embodiment, the term refers to an epitope recognized by fewer than 2% of the antigen-specific CD8$^+$ T cells. In another embodiment, the term refers to an epitope recognized by fewer than 1% of the antigen-specific CD8$^+$ T cells. In another embodiment, the term refers to an epitope recognized by fewer than 0.5% of the antigen-specific CD8$^+$ T cells.

Each type of the dominant epitope and subdominant epitope represents a separate embodiment of the present invention.

The antigen in methods and compositions of the present invention is, in one embodiment, expressed at a detectable level on a non-tumor cell of the subject. In another embodiment, the antigen is expressed at a detectable level on at least a certain percentage (e.g. 0.01%, 0.03%, 0.1%, 0.3%, 1%, 2%, 3%, or 5%) of non-tumor cells of the subject. In one embodiment, "non-tumor cell" refers to a cell outside the body of the tumor. In another embodiment, "non-tumor cell" refers to a non-malignant cell. In another embodiment, "non-tumor cell" refers to a non-transformed cell. In another embodiment, the non-tumor cell is a somatic cell. In another embodiment, the non-tumor cell is a germ cell. Each possibility represents a separate embodiment of the present invention.

"Detectable level" refers, in one embodiment, to a level detectable by a standard assay. In one embodiment, the assay is an immunological assay. In one embodiment, the assay is enzyme-linked immunoassay (ELISA). In another embodiment, the assay is Western blot. In another embodiment, the assay is FACS. It is to be understood by a skilled artisan that any other assay available in the art can be used in the methods provided herein. In another embodiment, a detectable level is determined relative to the background level of a particular assay. Methods for performing each of these techniques are well known to those skilled in the art, and each technique represents a separate embodiment of the present invention.

In one embodiment, vaccination with recombinant antigen-expressing LM induces epitope spreading. In another embodiment, vaccination with LLO-antigen fusions, even outside the context of Her2, induces epitope spreading as well. Each possibility represents a separate embodiment of the present invention.

In another embodiment, the present invention provides a method of impeding a growth of an Her-2-expressing tumor in a subject, comprising administering to the subject a recombinant polypeptide comprising an N-terminal fragment of a LLO protein fused to a Her-2 chimeric antigen, wherein the antigen has one or more subdominant CD8$^+$ T cell epitopes, wherein the subject mounts an immune response against the antigen-expressing tumor, thereby impeding a growth of an Her-2-expressing tumor in a subject. In another embodiment, the antigen does not contain any of the dominant CD8$^+$ T cell epitopes. In another embodiment, provided herein is a method of impeding a growth on a Her-2-expressing tumor in a subject, comprising administering to the subject a recombinant form of *Listeria* comprising a recombinant nucleotide encoding the recombinant polypeptide provided herein.

In another embodiment, the present invention provides a method for inducing formation of cytotoxic T cells in a host having cancer, comprising administering to the host a composition of the present invention, thereby inducing formation of cytotoxic T cells in a host having cancer.

In another embodiment, the present invention provides a method of reducing an incidence of cancer, comprising administering a composition of the present invention. In another embodiment, the present invention provides a method of ameliorating cancer, comprising administering a composition of the present invention. Each possibility represents a separate embodiment of the present invention.

In one embodiment, the composition is administered to the cells of the subject ex vivo; in another embodiment, the composition is administered to the cells of a donor ex vivo; in another embodiment, the composition is administered to the cells of a donor in vivo, then is transferred to the subject. Each possibility represents a separate embodiment of the present invention.

In one embodiment, the cancer treated by a method of the present invention is breast cancer. In another embodiment, the cancer is an Her2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is a CNS carcinoma In another embodiment, the cancer is an endometrial carcinoma. In another embodiment, the cancer is a bladder cancer. In another embodiment, the cancer is a head and neck cancer. In another embodiment, the cancer is a prostate carcinoma. Each possibility represents a separate embodiment of the present invention.

In another embodiment of the methods of the present invention, the subject mounts an immune response against the antigen-expressing tumor or target antigen, thereby mediating the anti-tumor effects.

In another embodiment, the present invention provides an immunogenic composition for treating cancer, the composition comprising a fusion of a truncated LLO to a Her-2 chimeric protein. In another embodiment, the immunogenic composition further comprises a *Listeria* strain expressing the fusion. Each possibility represents a separate embodiment of the present invention. In another embodiment, the present invention provides an immunogenic composition for treating cancer, the composition comprising a *Listeria* strain expressing a Her-2 chimeric protein.

In one embodiment, a treatment protocol of the present invention is therapeutic. In another embodiment, the protocol is prophylactic. In another embodiment, the vaccines of the present invention are used to protect people at risk for cancer such as breast cancer or other types of Her2-containing tumors because of familial genetics or other circumstances that predispose them to these types of ailments as will be understood by a skilled artisan. In another embodiment, the vaccines are used as a cancer immunotherapy after debulking of tumor growth by surgery, conventional chemotherapy or radiation treatment. Following such treatments, the vaccines of the present invention are administered so that the CTL response to the tumor antigen of the vaccine destroys remaining metastases and prolongs remission from the cancer. In another embodiment, vaccines of the present invention are used to effect the growth of previously established tumors and to kill existing tumor cells. Each possibility represents a separate embodiment of the present invention.

In another embodiment, the vaccines and immunogenic compositions utilized in any of the methods described above have any of the characteristics of vaccines and immunogenic compositions of the present invention. Each characteristic represents a separate embodiment of the present invention.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5 \times 10^7$ bacteria/dose. In another embodiment, the dosage is $2 \times 10^7$ bacteria/dose. In another embodiment, the dosage is $3 \times 10^7$ bacteria/dose. In another embodiment, the dosage is $4 \times 10^7$ bacteria/dose. In another embodiment, the dosage is $6 \times 10^7$ bacteria/dose. In another embodiment, the dosage is $8 \times 10^7$ bacteria/dose. In another embodiment, the dosage is $1 \times 10^8$ bacteria/dose. In another embodiment, the dosage is $1.5 \times 10^8$ bacteria/dose. In another embodiment, the dosage is $2 \times 10^8$ bacteria/dose. In another embodiment, the dosage is $3 \times 10^8$ bacteria/dose. In another embodiment, the dosage is $4 \times 10^8$ bacteria/dose. In another embodiment, the dosage is $6 \times 10^8$ bacteria/dose. In another embodiment, the dosage is $8 \times 10^8$ bacteria/dose. In another embodiment, the dosage is $1 \times 10^9$ bacteria/dose. In another embodiment, the dosage is $1.5 \times 10^9$ bacteria/dose. In another embodiment, the dosage is $2 \times 10^9$ bacteria/dose. In another embodiment, the dosage is $3 \times 10^9$ bacteria/dose. In another embodiment, the dosage is $5 \times 10^9$ bacteria/dose. In another embodiment, the dosage is $6 \times 10^9$ bacteria/dose. In another embodiment, the dosage is $8 \times 10^9$ bacteria/dose. In another embodiment, the dosage is $1 \times 10^{10}$ bacteria/dose. In another embodiment, the dosage is $1.5 \times 10^{10}$ bacteria/dose. In another embodiment, the dosage is $2 \times 10^{10}$ bacteria/dose. In another embodiment, the dosage is $3 \times 10^{10}$ bacteria/dose. In another embodiment, the dosage is $5 \times 10^{10}$ bacteria/dose. In another embodiment, the dosage is $6 \times 10^{10}$ bacteria/dose. In another embodiment, the dosage is $8 \times 10^{10}$ bacteria/dose. In another embodiment, the dosage is $8 \times 10^9$ bacteria/dose. In another embodiment, the dosage is $1 \times 10^{11}$ bacteria/dose. In another embodiment, the dosage is $1.5 \times 10^{11}$ bacteria/dose. In another embodiment, the dosage is $2 \times 10^{11}$ bacteria/dose. In another embodiment, the dosage is $3 \times 10^{11}$ bacteria/dose. In another embodiment, the dosage is $5 \times 10^{11}$ bacteria/dose. In another embodiment, the dosage is $6 \times 10^{11}$ bacteria/dose. In another embodiment, the dosage is $8 \times 10^{11}$ bacteria/dose. Each possibility represents a separate embodiment of the present invention.

In one embodiment, a vaccine or immunogenic composition of the present invention is administered alone to a subject. In another embodiment, the vaccine or immunogenic composition is administered together with another cancer therapy. Each possibility represents a separate embodiment of the present invention.

The recombinant *Listeria* of methods and compositions of the present invention is, in one embodiment, stably transformed with a construct encoding an Her-2 chimeric antigen or an LLO-Her-2 chimeric antigen fusion. In one embodiment, the construct contains a polylinker to facilitate further subcloning. Several techniques for producing recombinant *Listeria* are known.

In one embodiment, the construct or nucleic acid molecule is integrated into the Listerial chromosome using homologous recombination. Techniques for homologous recombination are well known in the art, and are described, for example, in Baloglu S, Boyle S M, et al (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In this case, a recombinant LM strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants. Each technique represents a separate embodiment of the present invention.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. Each possibility represents a separate embodiment of the present invention.

In another embodiment, one of various promoters is used to express the antigen or fusion protein containing same. In one embodiment, an LM promoter is used, e.g. promoters for the genes hly, actA, pica, plcB and mpl, which encode the Listerial proteins hemolysin, actA, phosphotidylinositol-specific phospholipase, phospholipase C, and metalloprotease, respectively. Each possibility represents a separate embodiment of the present invention.

In another embodiment, methods and compositions of the present invention utilize a homologue of a Her-2 chimeric protein or LLO sequence of the present invention. In another embodiment, the methods and compositions of the present invention utilize a Her-2 chimeric protein from a non-human mammal. The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-4 of greater than 70%. In another embodiment, "homology" refers to identity to a sequence selected from SEQ ID No: 1-4 of greater than 72%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%. In another embodiment, the identity is greater than 92%. In another embodiment, the identity is greater than 93%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

In one embodiment of the present invention, "nucleic acids" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

The terms "contacting" or "administering," in one embodiment, refer to directly contacting the cancer cell or tumor with a composition of the present invention. In another embodiment, the terms refer to indirectly contacting the cancer cell or tumor with a composition of the present invention. In another embodiment, methods of the present invention include methods in which the subject is contacted with a composition of the present invention after which the composition is brought in contact with the cancer cell or tumor by diffusion or any other active transport or passive transport process known in the art by which compounds circulate within the body. Each possibility represents a separate embodiment of the present invention.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

Pharmaceutical Compositions

The pharmaceutical compositions containing vaccines and compositions of the present invention are, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to increasing performance free survival or overall survival of a patient. In another embodiment, "treating" refers to stabilizing the progression of a disease. In another embodiment, "treating" refers to inducing remission. In another embodiment, "treating" refers to slowing the progression of a disease. The terms "reducing", "suppressing" and "inhibiting" refer in another embodiment to lessening or decreasing. Each possibility represents a separate embodiment of the present invention.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

In one embodiment, the term "Mammal" for purposes of treatment refers to any animal classified as a mammal, including humans, domestic and farm animals, and zoo, sports, or pet animals, such as canines, including dogs, and horses, cats, cattle, pigs, sheep, etc.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a vaccine provided herein for purposes of treatment of tumor may be determined empirically and in a routine manner.

The following examples are presented in order to more fully illustrate the preferred embodiments of the invention. They should in no way be construed, however, as limiting the broad scope of the invention.

EXAMPLES

Materials and Methods

Oligonucleotides were synthesized by Invitrogen (Carlsbad, Calif.) and DNA sequencing was done by Genewiz Inc, South Plainfield, N.J. Flow cytometry reagents were purchased from Becton Dickinson Biosciences (BD, San Diego, Calif.). Cell culture media, supplements and all other reagents, unless indicated, were from Sigma (St. Louise, Mo.). Her2/neu HLA-A2 peptides were synthesized by EZbiolabs (Westfield, Ind.). Complete RPMI 1640 (C-RPMI) medium contained 2 mM glutamine, 0.1 mM non-essential amino acids, and 1 mM sodium pyruvate, 10% fetal bovine serum, penicillin/streptomycin, Hepes (25 mM). The polyclonal anti-LLO antibody was described previously and anti-Her2/neu antibody was purchased from Sigma.

Mice and Cell Lines

All animal experiments were performed according to approved protocols by IACUC at the University of Pennsylvania or Rutgers University. FVB/N mice were purchased from Jackson laboratories (Bar Harbor, Me.). The FVB/N Her2/neu transgenic mice, which overexpress the rat Her2/neu onco-protein were housed and bred at the animal core facility at the University of Pennsylvania. The NT-2 tumor cell line expresses high levels of rat Her2/neu protein, was derived from a spontaneous mammary tumor in these mice and grown as described previously. DHFR-G8 (3T3/neu) cells were obtained from ATCC and were grown according to the ATCC recommendations. The EMT6-Luc cell line was a generous gift from Dr. John Ohlfest (University of Minnesota, Minn.) and was grown in complete C-RPMI medium. Bioluminescent work was conducted under guidance by the Small Animal Imaging Facility (SAIF) at the University of Pennsylvania (Philadelphia, Pa.).

Listeria Constructs and Antigen Expression

Her2/neu-pGEM7Z was kindly provided by Dr. Mark Greene at the University of Pennsylvania and contained the full-length human Her2/neu (hHer2) gene cloned into the pGEM7Z plasmid (Promega, Madison Wis.). This plasmid was used as a template to amplify three segments of hHer-2/neu, namely, EC1, EC2, and IC1, by PCR using pfx DNA polymerase (Invitrogen) and the oligos indicated in Table 1.

ChHer2 gene was excised from pAdv138 using XhoI and SpeI restriction enzymes, and cloned in frame with a truncated, non-hemolytic fragment of LLO in the Lmdd shuttle vector, pAdv134. The sequences of the insert, LLO and hly promoter were confirmed by DNA sequencing analysis. This plasmid was electroporated into electro-competent actA, dal, dat mutant *Listeria monocytogenes* strain, LmddA and positive clones were selected on Brain Heart infusion (BHI) agar plates containing streptomycin (250 μg/ml). In some experiments similar *Listeria* strains expressing hHer2/neu (Lm-hHer2) fragments were used for comparative purposes. These have been previously described. In all studies, an irrelevant *Listeria* construct (Lm-control) was included to account for the antigen independent effects of *Listeria* on the immune system. Lm-controls were based on the same *Listeria* plat-

TABLE 1

Primers for cloning of Human her-2-Chimera

| | DNA sequence | Base pair region | Amino acid region or junctions |
|---|---|---|---|
| Her-2-Chimera (F) | TGAT<u>CTCGAG</u>ACCCACCTGGACATGCTC (SEQ ID NO: 57) | 120-510 | 40-170 |
| HerEC1-EC2F (Junction) | CTACCAGGACACGATTTTGTGGAAG-AATATCCA GGAGTTTGCTGGCTGC (SEQ ID NO: 58) | 510/1077 | 170/359 |
| HerEC1-EC2R (Junction) | GCAGCCAGCAAACTCCTGGATATT-CTTCCACAA AATCGTGTCCTGGTAG (SEQ ID NO: 59) | | |
| HerEC2-IC1F (Junction) | CTGCCACCAGCTGTGCGCCCGAGGG-CAGCAGAAGATCCGGAAGTACACGA (SEQ ID NO: 60) | 1554/2034 | 518/679 |
| HerEC2-IC1R (Junction) | TCGTGTACTTCCGGATCTTCTGCTG CCCTCGGGC GCACAGCTGGTGGCAG (SEQ ID NO: 61) | | |
| Her-2-Chimera (R) | GTGG<u>CCCGGG</u>TCTAGATTAGTCTAAGAGGCAGCCATAGG (SEQ ID NO: 62) | 2034-2424 | 679-808 |

The Her-2/neu chimera construct was generated by direct fusion by the SOEing PCR method and each separate hHer-2/neu segment as templates. Primers are shown in Table 2.

Sequence of primers for amplification of different segments human Her2 regions form as ADXS31-164, but expressed a different antigen such as HPV16-E7 or NY-ESO-1. Expression and secretion of fusion proteins from *Listeria* were tested. Each construct was passaged twice in vivo.

| | DNA sequence | Base pair region | Amino acid region |
|---|---|---|---|
| Her-2-EC1(F) | CCGC<u>CTCGAG</u>GCCGCGAGCACCCAAGTG (SEQ ID NO: 63) | 58-979 | 20-326 |
| Her-2-EC1(R) | CGCG<u>ACTAGT</u>TTAATCCTCTGCTGTCACCTC (SEQ ID NO: 64) | | |
| Her-2-EC2(F) | CCGC<u>CTCGAG</u>TACCTTTCTACGGACGTG (SEQ ID NO: 65) | 907-1504 | 303-501 |
| Her-2-EC2(R) | CGCG<u>ACTAGT</u>TTACTCTGGCCGGTTGGCAG (SEQ ID NO: 66) | | |
| Her-2-Her-2-IC1(F) | CCGC<u>CTCGAG</u>CAGCAGAAGATCCGGAAGTAC (SEQ ID NO: 67) | 2034-3243 | 679-1081 |
| Her-2-IC1(R) | CGCG<u>ACTAGT</u>TTAAGCCCCTTCGGAGGGTG (SEQ ID NO: 68) | | |

Cytotoxicity Assay

Groups of 3-5 FVB/N mice were immunized three times with one week intervals with 1×10⁸ colony forming units (CFU) of Lm-LLO-ChHer2, ADXS31-164, Lm-hHer2 ICI or Lm-control (expressing an irrelevant antigen) or were left naïve. NT-2 cells were grown in vitro, detached by trypsin and treated with mitomycin C (250 μg/ml in serum free C-RPMI medium) at 37° C. for 45 minutes. After 5 washes, they were co-incubated with splenocytes harvested from immunized or naïve animals at a ratio of 1:5 (Stimulator:Responder) for 5 days at 37° C. and 5% $CO_2$. A standard cytotoxicity assay was performed using europium labeled 3T3/neu (DHFR-G8) cells as targets according to the method previously described. Released europium from killed target cells was measured after 4 hour incubation using a spectrophotometer (Perkin Elmer, Victor²) at 590 nm Percent specific lysis was defined as (lysis in experimental group-spontaneous lysis)/(Maximum lysis-spontaneous lysis).

Interferon-γ Secretion by Splenocytes from Immunized Mice

Groups of 3-5 FVB/N or HLA-A2 transgenic mice were immunized three times with one week intervals with 1×10⁸ CFU of ADXS31-164, a negative *Listeria* control (expressing an irrelevant antigen) or were left naïve. Splenocytes from FVB/N mice were isolated one week after the last immunization and co-cultured in 24 well plates at 5×10⁶ cells/well in the presence of mitomycin C treated NT-2 cells in C-RPMI medium. Splenocytes from the HLA-A2 transgenic mice were incubated in the presence of 1 μM of HLA-A2 specific peptides or 1 μg/ml of a recombinant His-tagged ChHer2 protein, produced in *E. coli* and purified by a nickel based affinity chromatography system. Samples from supernatants were obtained 24 or 72 hours later and tested for the presence of interferon-γ (IFN-γ) using mouse IFN-γ Enzyme-linked immunosorbent assay (ELISA) kit according to manufacturer's recommendations.

Tumor Studies in Her2 Transgenic Animals

Six weeks old FVB/N rat Her2/neu transgenic mice (9-14/group) were immunized 6 times with 5×10⁸ CFU of Lm-LLO-ChHer2, ADXS31-164 or Lm-control. They were observed twice a week for the emergence of spontaneous mammary tumors, which were measured using an electronic caliper, for up to 52 weeks. Escaped tumors were excised when they reached a size 1 cm² in average diameter and preserved in RNA later at −20° C. In order to determine the effect of mutations in the Her2/neu protein on the escape of these tumors, genomic DNA was extracted using a genomic DNA isolation kit, and sequenced.

Effect of ADXS31-164 on Regulatory T Cells in Spleens and Tumors

Mice were implanted subcutaneously (s.c.) with 1×10⁶ NT-2 cells. On days 7, 14 and 21, they were immunized with 1×10⁸ CFUs of ADXS31-164, LmddA-control or left naïve. Tumors and spleens were extracted on day 28 and tested for the presence of CD3⁺/CD4⁺/FoxP3⁺ Tregs by FACS analysis. Briefly, splenocytes were isolated by homogenizing the spleens between two glass slides in C-RPMI medium. Tumors were minced using a sterile razor blade and digested with a buffer containing DNase (12 U/ml), and collagenase (2 mg/ml) in PBS. After 60 min incubation at RT with agitation, cells were separated by vigorous pipetting. Red blood cells were lysed by RBC lysis buffer followed by several washes with complete RPMI-1640 medium containing 10% FBS. After filtration through a nylon mesh, tumor cells and splenocytes were resuspended in FACS buffer (2% FBS/PBS) and stained with anti-CD3-PerCP-Cy5.5, CD4-FITC, CD25-APC antibodies followed by permeabilization and staining with anti-Foxp3-PE. Flow cytometry analysis was performed using 4-color FACS calibur (BD) and data were analyzed using cell quest software (BD).

Statistical Analysis

The log-rank Chi-Squared test was used for survival data and student's t-test for the CTL and ELISA assays, which were done in triplicates. A p-value of less than 0.05 (marked as *) was considered statistically significant in these analyzes. All statistical analysis was done with either Prism software, V.4.0a (2006) or SPSS software, V.15.0 (2006). For all FVB/N rat Her2/neu transgenic studies we used 8-14 mice per group, for all wild-type FVB/N studies we used at least 8 mice per group unless otherwise stated. All studies were repeated at least once except for the long term tumor study in Her2/neu transgenic mouse model.

Example 1

Generation of *L. Monocytogenes* Strains that Secrete LLO Fragments Fused to Her-2 Fragments: Construction of ADXS31-164

Construction of the chimeric Her2/neu gene (ChHer2) was described previously. Briefly, ChHer2 gene was generated by direct fusion of two extracellular (aa 40-170 and aa 359-433) and one intracellular fragment (aa 678-808) of the Her2/neu protein by SOEing PCR method. The chimeric protein harbors most of the known human MHC class I epitopes of the protein. ChHer2 gene was excised from the plasmid, pAdv138 (which was used to construct Lm-LLO-ChHer2) and cloned into LmddA shuttle plasmid, resulting in the plasmid pAdv164 (FIG. 1A). There are two major differences between these two plasmid backbones. 1) Whereas pAdv138 uses the chloramphenicol resistance marker (cat) for in vitro selection of recombinant bacteria, pAdv164 harbors the D-alanine racemase gene (dal) from *bacillus subtilis*, which uses a metabolic complementation pathway for in vitro selection and in vivo plasmid retention in LmddA strain which lacks the dal-dat genes. This vaccine platform was designed and developed to address FDA concerns about the antibiotic resistance of the engineered *Listeria* vaccine strains. 2) Unlike pAdv138, pAdv164 does not harbor a copy of the prfA gene in the plasmid (see sequence below and FIG. 1A), as this is not necessary for in vivo complementation of the Lmdd strain. The LmddA vaccine strain also lacks the actA gene (responsible for the intracellular movement and cell-to-cell spread of *Listeria*) so the recombinant vaccine strains derived from this backbone are 100 times less virulent than those derived from the Lmdd, its parent strain. LmddA-based vaccines are also cleared much faster (in less than 48 hours) than the Lmdd-based vaccines from the spleens of the immunized mice. The expression and secretion of the fusion protein tLLO-ChHer2 from this strain was comparable to that of the Lm-LLO-ChHer2 in TCA precipitated cell culture supernatants after 8 hours of in vitro growth (FIG. 1B) as a band of ~104 KD was detected by an anti-LLO antibody using Western Blot analysis. The *Listeria* backbone strain expressing only tLLO was used as negative control.

pAdv164 sequence (7075 base pairs) (see FIG. 1):

(SEQ ID NO: 53)
cggagtgtatactggcttactatgttggcactgatgagggtgtcagtgaa gtgcttcatgtggcaggagaaaaaaggctgcaccggtgcgtcagcagaat atgtgatacaggatatattccgcttcctcgctcactgactcgctacgctc -continued ggtcgttcgactgcggcgagcggaaatggcttacgaacggggcggagatt
tcctggaagatgccaggaagatacttaacagggaagtgagagggccgcgg
caaagccgttttttccataggctccgcccccctgacaagcatcacgaaatc
tgacgctcaaatcagtggtggcgaaacccgacaggactataaagatacca
ggcgtttccccctggcggctccctcgtgcgctctcctgttcctgcctttc
ggtttaccggtgtcattccgctgttatggccgcgtttgtctcattccacg
cctgacactcagttccgggtaggcagttcgctccaagctggactgtatgc
acgaaccccccgttcagtccgaccgctgcgccttatccggtaactatcgt
cttgagtccaacccggaaagacatgcaaaagcaccactggcagcagccac
tggtaattgatttagaggagttagtcttgaagtcatgcgccggttaaggc
taaactgaaaggacaagttttggtgactgcgctcctccaagccagttacc
tcggacaaagagttggtagctcagagaaccttcgaaaaaccgccctgcaa
ggcggttttttcgttttcagagcaagagattacgcgcagaccaaaacgat
ctcaagaagatcatcttattaatcagataaaatatttctagccctccttt
gattagtatattcctatcttaaagttacttttatgtggaggcattaacat
ttgttaatgacgtcaaaaggatagcaagactagaataaagctataaagca
agcatataatattgcgtttcatctttagaagcgaatttcgccaatattat
aattatcaaaagaggggtggcaaacggtatttggcattattaggttaa
aaaatgtagaaggagagtgaaacccatgaaaaaaataatgctagttttta
ttacacttatattagttagtctaccaattgcgcaacaaactgaagcaaag
gatgcatctgcattcaataaagaaaattcaatttcatccatggcaccacc
agcatctccgcctgcaagtcctaagacgccaatcgaaaagaaacacgcgg
atgaaatcgataagtatatacaaggattggattacaataaaaacaatgta
ttagtataccacggagatgcagtgacaaatgtgccgccaagaaaaggtta
caaagatggaaatgaatatattgttgtggagaaaaagaagaaatccatca
atcaaaataatgcagacattcaagttgtgaatgcaatttcgagcctaacc
tatccaggtgctctcgtaaaagcgaattcggaattagtagaaaatcaacc
agatgttctccctgtaaaacgtgattcattaacactcagcattgatttgc
caggtatgactaatcaagcaataaaatagttgtaaaaaatgccactaaa
tcaaacgttaacaacgcagtaaatacattagtggaaagatggaatgaaaa
atatgctcaagcttatccaaatgtaagtgcaaaaattgattatgatgacg
aaatggcttacagtgaatcacaattaattgcgaaatttggtacagcattt
aaagctgtaaataatagcttgaatgtaaacttcggcgcaatcagtgaagg
gaaaatgcaagaagaagtcattagttttaaacaaatttactataacgtga
atgttaatgaacctacaagaccttccagatttttcggcaaagctgttact
aaagagcagttgcaagcgcttggagtgaatgcagaaaatcctcctgcata
tatctcaagtgtggcgtatggccgtcaagtttatttgaaattatcaacta
attcccatagtactaaagtaaaagctgctttgatgctgccgtaagcggaa
aatctgtctcaggtgatgtagaactaacaaatatcatcaaaaattcttcc
ttcaaagccgtaatttacggaggttccgcaaaagatgaagttcaaatcat
cgacggcaacctcggagacttacgcgatattttgaaaaaaggcgctactt -continued ttaatcgagaaacaccaggagttcccattgcttatacaacaaacttccta
aaagacaatgaattagctgttattaaaaacaactcagaatatattgaaac
aacttcaaaagcttatacagatggaaaaattaacatcgatcactctggag
gatacgttgctcaattcaacattttcttgggatgaagtaaattatgatctc
gagacccacctggacatgctccgccacctctaccagggctgccaggtggt
gcagggaaacctggaactcacctacctgcccaccaatgccagcctgtcct
tcctgcaggatatccaggaggtgcagggctacgtgctcatcgctcacaac
caagtgaggcaggtcccactgcagaggctgcggattgtgcgaggcaccca
gctctttgaggacaactatgccctggccgtgctagacaatggagacccgc
tgaacaataccaccccctgtcacagggtgcctcccagggaggcctgcgggag
ctgcagcttcgaagcctcacagagatcttgaaaggagggggtcttgatcca
gcggaaccccagctctgctaccaggacacgattttgtggaagaatatcc
aggagtttgctggctgcaagaagatctttgggagcctggcatttctgccg
gagagctttgatggggacccagcctccaacactgccccgctccagccaga
gcagctccaagtgtttgagactctggaagagatcacaggttacctataca
tctcagcatggccggacgcctgcctgacctcagcgtcttccagaacctg
caagtaatccggggacgaattctgcacaatggcgcctactcgctgaccct
gcaagggctgggcatcagctggctggggctgcgctcactgagggaactgg
gcagtggactggccctcatccaccataacacccacctctgcttcgtgcac
acggtgccctgggaccagctctttcggaacccgcaccaagctctgctcca
cactgccaaccggccagaggacgagtgtgtgggcgagggcctggcctgcc
accagctgtgcgcccgagggcagcagaagatccggaagtacacgatgcgg
agactgctgcaggaaacggagctggtggagccgctgacacctagcggagc
gatgcccaaccaggcgcagatgcggatcctgaaagagacggagctgagga
aggtgaaggtgcttggatctggcgcttttggcacagtctacaagggcatc
tggatccctgatggggagaatgtgaaaattccagtggccatcaaagtgtt
gagggaaaacacatcccccaaagccaacaaagaaatcttagacgaagcat
acgtgatggctggtgtgggctccccatatgtctcccgccttctgggcatc
tgcctgacatccacggtgcagctggtgacacagcttatgccctatggctg
cctcttagactaatctagacccgggccactaactcaacgctagtagtgga
tttaatcccaaatgagccaacagaaccagaaccagaaacagaacaagtaa
cattggagttagaaatggaagaagaaaaaagcaatgatttcgtgtgaata
atgcacgaaatcattgcttatttttttaaaaagcgatatactagatataa
cgaaacaacgaactgaataaagaatacaaaaaaagagccacgaccagtta
aagcctgagaaactttaactgcgagccttaattgattaccaccaatcaat
taaagaagtcgagacccaaaatttggtaaagtatttaattactttattaa
tcagatacttaaatatctgtaaacccattatatcgggttttttgagggat
ttcaagtctttaagaagataccaggcaatcaattaagaaaaacttagttg
attgccttttttgttgtgattcaactttgatcgtagcttctaactaatta
attttcgtaagaaaggagaacagctgaatgaatatccctttttgttgtaga -continued
```
aactgtgcttcatgacggcttgttaaagtacaaatttaaaaatagtaaaa
ttcgctcaatcactaccaagccaggtaaaagtaaaggggctattttgcg
tatcgctcaaaaaaagcatgattggcggacgtggcgttgttctgacttc
cgaagaagcgattcacgaaaatcaagatacatttacgcattggacaccaa
acgtttatcgttatggtacgtatgcagacgaaaaccgttcatacactaaa
ggacattctgaaaacaatttaagacaaatcaataccttctttattgattt
tgatattcacacggaaaagaaactatttcagcaagcgatattttaacaa
cagctattgatttaggttttatgcctacgttaattatcaaatctgataaa
ggttatcaagcatattttgttttagaaacgccagtctatgtgacttcaaa
atcagaatttaaatctgtcaaagcagccaaaataatctcgcaaaatatcc
gagaatattttggaaagtctttgccagttgatctaacgtgcaatcatttt
gggattgctcgtataccaagaacggacaatgtagaattttttgatcccaa
ttaccgttattcttcaaagaatggcaagattggtctttcaaacaaacag
ataataagggctttactcgttcaagtctaacggttttaagcggtacagaa
ggcaaaaacaagtagatgaacctggtttaatctcttattgcacgaaac
gaaattttcaggagaaagggtttagtagggcgcaatagcgttatgttta
ccctctcttagcctactttagttcaggctattcaatcgaaacgtgcgaa
tataatatgtttgagtttaataatcgattagatcaacccttagaagaaaa
agaagtaatcaaattgttagaagtgcctattcagaaaactatcaagggg
ctaatagggaatacattaccattctttgcaaagctttgggtatcaagtgat
ttaaccagtaaagatttatttgtccgtcaagggtggtttaaattcaagaa
aaaaagaagcgaacgtcaacgtgttcatttgtcagaatggaaagaagatt
taatggcttatattagcgaaaaagcgatgtatacaagccttatttagcg
acgaccaaaaaagagattagagaagtgctaggcattcctgaacggacatt
agataaattgctgaaggtactgaaggcgaatcaggaaatttttctttaaga
ttaaaccaggaagaaatggtggcattcaacttgctagtgttaaatcattg
ttgctatcgatcattaaattaaaaaaagaagaacgagaaagctatataaa
ggcgctgacagcttcgtttaatttagaacgtacatttattcaagaaactc
taaacaaattggcagaacgccccaaaacggacccacaactcgatttgttt
agctacgatacaggctgaaaataaaacccgcactatgccattacatttat
atctatgatacgtgtttgttttctttgctggctagcttaattgcttata
tttacctgcaataaaggattcttacttccattatactcccattttccaa
aaacatacggggaacacggaacttattgtacaggccacctcatagttaa
tggtttcgagccttcctgcaatctcatccatggaaatatattcatccccc
tgccggcctattaatgtgacttttgtgccggcggatattcctgatccag
ctccaccataaattggtccatgcaaattcggccgcaattttcaggcgtt
ttcccttcacaaggatgtcggtcccttcaattttcggagccagccgtcc
gcatagcctacaggcaccgtcccgatccatgtgtcttttccgctgtgta
ctcggctccgtagctgacgctctcgcctttctgatcagtttgacatgtg
acagtgtcgaatgcagggtaaatgccggacgcagctgaaacggtatctcg
tccgacatgtcagcagacgggcgaaggccatacatgccgatgccgaatct
```

-continued
```
gactgcattaaaaaagcatttttcagccggagtccagcggcgctgttcgc
gcagtggaccattagattctttaacggcagcggagcaatcagctctttaa
agcgctcaaactgcattaagaaatagcctctttcttttcatccgctgtc
gcaaaatgggtaaataccccttgcactttaaacgagggttgcggtcaag
aattgccatcacgttctgaacttcttcctctgttttacaccaagtctgt
tcatccccgtatcgaccttcagatgaaaatgaagagaaccttttcgtg
tggcgggctgcctcctgaagccattcaacagaataacctgttaaggtcac
gtcatactcagcagcgattgccacatactccgggggaaccgcgccaagca
ccaatataggcgccttcaatccctttttagcgcagtgaaatcgcttcatc
caaaatggccacggccaagcatgaagcacctgcgtcaagagcagcctttg
ctgtttctgcatcaccatgcccgtaggcgtttgctttcacaactgccatc
aagtggacatgttcaccgatatgtttttcatattgctgacattttcctt
tatcgcggacaagtcaatttccgcccacgtatctctgtaaaaaggttttg
tgctcatggaaaactcctctcttttttcagaaaatcccagtacgtaatta
agtatttgagaattaattttatattgattaatactaagtttacccagttt
tcacctaaaaaacaaatgatgagataatagctccaaaggctaaagaggac
tataccaactatttgttaattaa
```

Example 2

ADXS31-164 is as Immunogenic as LM-LLO-ChHER2

Immunogenic properties of ADXS31-164 in generating anti-Her2/neu specific cytotoxic T cells were compared to those of the Lm-LLO-ChHer2 vaccine in a standard CTL assay. Both vaccines elicited strong but comparable cytotoxic T cell responses toward Her2/neu antigen expressed by 3T3/neu target cells. Accordingly, mice immunized with a *Listeria* expressing only an intracellular fragment of Her2-fused to LLO showed lower lytic activity than the chimeras which contain more MHC class I epitopes. No CTL activity was detected in naïve animals or mice injected with the irrelevant *Listeria* vaccine (FIG. 2A). ADXS31-164 was also able to stimulate the secretion of IFN-γ by the splenocytes from wild type FVB/N mice (FIG. 2B). This was detected in the culture supernatants of these cells that were co-cultured with mitomycin C treated NT-2 cells, which express high levels of Her2/neu antigen (FIG. 5C).

Proper processing and presentation of the human MHC class I epitopes after immunizations with ADXS31-164 was tested in HLA-A2 mice. Splenocytes from immunized HLA-A2 transgenics were co-incubated for 72 hours with peptides corresponding to mapped HLA-A2 restricted epitopes located at the extracellular (HLYQGCQVV SEQ ID NO: 11 or KIFGSLAFL SEQ ID NO: 12) or intracellular (RLLQETELV SEQ ID NO: 13) domains of the Her2/neu molecule (FIG. 2C). A recombinant ChHer2 protein was used as positive control and an irrelevant peptide or no peptide as negative controls. The data from this experiment show that ADXS31-164 is able to elicit anti-Her2/neu specific immune responses to human epitopes that are located at different domains of the targeted antigen.

Example 3

Figure 3:
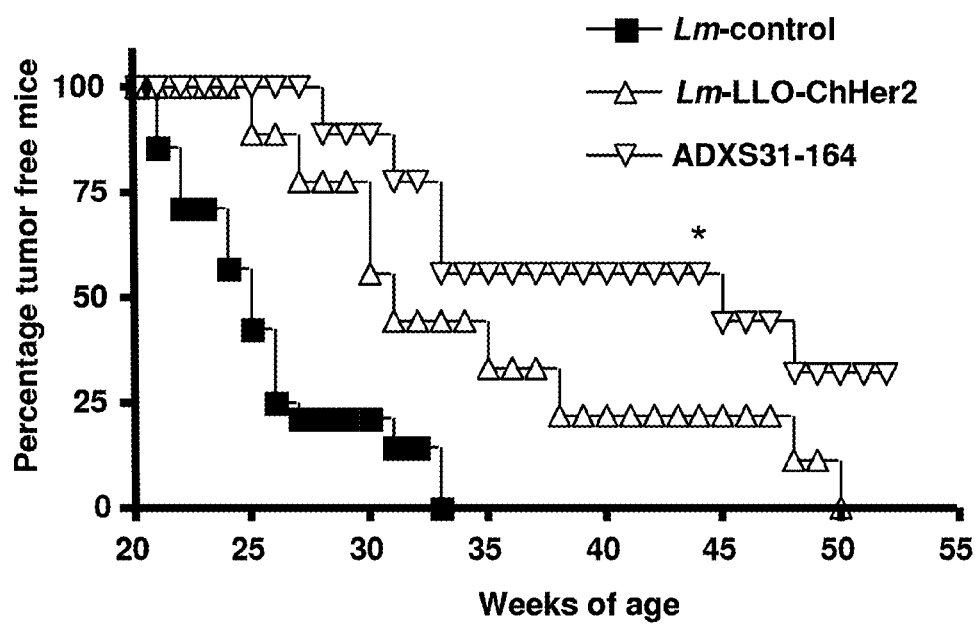
FIG. 3. Tumor Prevention Studies for *Listeria*-ChHer2/neu Vaccines Her2/neu transgenic mice were injected six times with each recombinant *Listeria*-ChHer2 or a control *Listeria* vaccine Immunizations started at 6 weeks of age and continued every three weeks until week 21. Appearance of tumors was monitored on a weekly basis and expressed as percentage of tumor free mice. *p<0.05, N=9 per group.

ADXS31-164 was More Efficacious than LM-LLO-ChHER2 in Preventing the Onset of Spontaneous Mammary Tumors Anti-tumor effects of ADXS31-164 were compared to those of Lm-LLO-ChHer2 in Her2/neu transgenic animals which develop slow growing, spontaneous mammary tumors at 20-25 weeks of age. All animals immunized with the irrelevant Listeria-control vaccine developed breast tumors within weeks 21-25 and were sacrificed before week 33. In contrast, Liseria-Her2/neu recombinant vaccines caused a significant delay in the formation of the mammary tumors. On week 45, more than 50% o ADXS31-164 vaccinated mice (5 out of 9) were still tumor free, as compared to 25% of mice immunized with Lm-LLO-ChHer2. At week 52, 2 out of 8 mice immunized with ADXS31-164 still remained tumor free, whereas all mice from other experimental groups had already succumbed to their disease (FIG. 3). These results indicate that despite being more attenuated, ADXS31-164 is more efficacious than Lm-LLO-ChHer2 in preventing the onset of spontaneous mammary tumors in Her2/neu transgenic animals.

Example 4

Mutations in HER2/NEU Gene Upon Immunization with ADXS31-164

Mutations in the MHC class I epitopes of Her2/neu have been considered responsible for tumor escape upon immunization with small fragment vaccines or trastuzumab (Herceptin), a monoclonal antibody that targets an epitope in the extracellular domain of Her2/neu. To assess this, genomic material was extracted from the escaped tumors in the transgenic animals and sequenced the corresponding fragments of the neu gene in tumors immunized with the chimeric or control vaccines. Mutations were not observed within the Her-2/neu gene of any vaccinated tumor samples suggesting alternative escape mechanisms (data not shown).

Example 5

Figure 4:
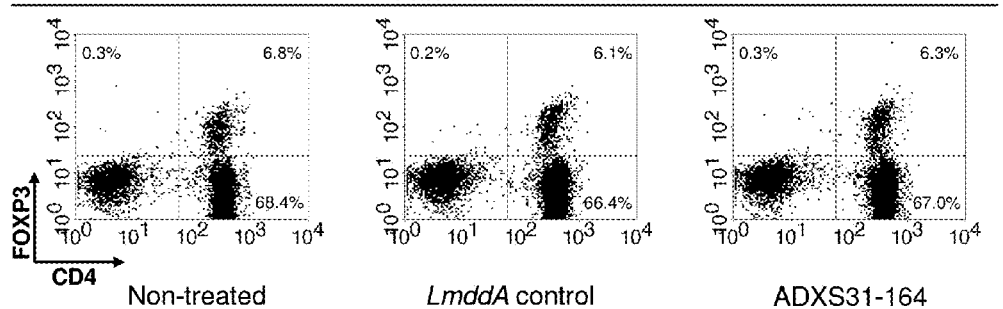
FIG. 4. Effect of immunization with ADXS31-164 on the % of Tregs in Spleens. FVB/N mice were inoculated s.c. with $1 \times 10^6$ NT-2 cells and immunized three times with each vaccine at one week intervals. Spleens were harvested 7 days after the second immunization. After isolation of the immune cells, they were stained for detection of Tregs by anti CD3, CD4, CD25 and FoxP3 antibodies. dot-plots of the Tregs from a representative experiment showing the frequency of $CD25^+/FoxP3^+$ T cells, expressed as percentages of the total $CD3^+$ or $CD3^+CD4^+$ T cells across the different treatment groups.
Figure 4:
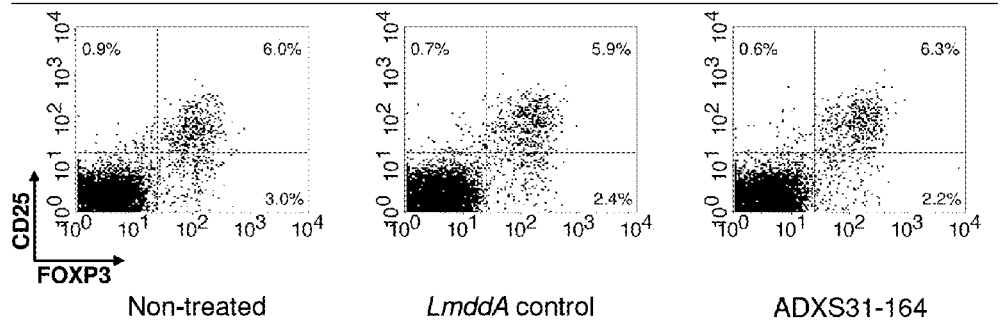

ADXS31-164 Causes a Significant Decrease in Intra-Tumoral T Regulatory Cells To elucidate the effect of ADXS31-164 on the frequency of regulatory T cells in spleens and tumors, mice were implanted with NT-2 tumor cells. Splenocytes and intra-tumoral lymphocytes were isolated after three immunizations and stained for Tregs, which were defined as $CD3^+/CD4^+/CD25^+/FoxP3^+$ cells, although comparable results were obtained with either FoxP3 or CD25 markers when analyzed separately. The results indicated that immunization with ADXS31-164 had no effect on the frequency of Tregs in the spleens, as compared to an irrelevant Listeria vaccine or the naïve animals (See FIG. 4). In contrast, immunization with the Listeria vaccines caused a considerable impact on the presence of Tregs in the tumors (FIG. 5A). Whereas in average 19.0% of all $CD3^+$ T cells in untreated tumors were Tregs, this frequency was reduced to 4.2% for the irrelevant vaccine and 3.4% for ADXS31-164, a 5-fold reduction in the frequency of intra-tumoral Tregs (FIG. 5B). The decrease in the frequency of intra-tumoral Tregs in mice treated with either of the LmddA vaccines could not be attributed to differences in the sizes of the tumors. In a representative experiment, the tumors from mice immunized with ADXS31-164 were significantly smaller [mean diameter (mm)±SD, 6.71±0.43, n=5] than the tumors from untreated mice (8.69±0.98, n=5, p<0.01) or treated with the irrelevant vaccine (8.41±1.47, n=5, p=0.04), whereas comparison of these last two groups showed no statistically significant difference in tumor size (p=0.73). The lower frequency of Tregs in tumors treated with LmddA vaccines resulted in an increased intratumoral CD8/Tregs ratio, suggesting that a more favorable tumor microenvironment can be obtained after immunization with LmddA vaccines. However, only the vaccine expressing the target antigen HER2/neu (ADXS31-164) was able to reduce tumor growth, indicating that the decrease in Tregs has an effect only in the presence on antigen-specific responses in the tumor.

Example 6

No Escape Mutations were Introduced by Listeria Vaccine Expressing HER-2 Chimera Tumor samples of the mice immunized with different vaccines such as Lm-LLO-138, LmddA164 and irrelevant vaccine Lm-LLO-NY were harvested. The DNA was purified from these samples and the DNA fragments corresponding to Her-2/neu regions IC1, EC1 and EC2 were amplified and were sequenced to determine if there were any immune escape mutations. The alignment of sequence from each DNA was performed using CLUSTALW. The results of the analysis indicated that there were no mutations in the DNA sequences harvested from tumors. The detailed analysis of these sequences is shown below.

Alignment of EC2 (975-1029 bp of Her-2-neu)

```
Reference
                                                    (SEQ ID NO:14)
GGTCACAGCTGAGGACGGAACACAGCGTTGTGAGAAATGCAGCAAGCCCTGTGCT Lm-LLO-138-2
GGTCACAGCTGAGGACGGAACACAGCGTTGTGAGAAATGCAGCAAGCCCTGTGCT Lm-LLO-138-3
GGTCACAGCTGAGGACGGAACACAGCGTTGTGAGAAATGCAGCAAGCCCTGTGCT Lm-ddA-164-1
GGTCACAGCTGAGGACGGAACACAGCGTTGTGAGAAATGCAGCAAGCCCTGTGCT LmddA164-2
GGTCACAGCTGAGGACGGAACACAGCGTTGTGAGAAATGCAGCAAGCCCTGTGCT Lm-ddA-164-3
GGTCACAGCTGAGGACGGAACACAGCGTTGTGAGAAATGCAGCAAGCCCTGTGCT
```

-continued

LmddA164-4
GGTCACAGCTGAGGACGGAACACAGCGTTGTGAGAAATGCAGCAAGCCCTGTGCT

Lm-ddA-164-5
GGTCACAGCTGAGGACGGAACACAGCGTTGTGAGAAATGCAGCAAGCCCTGTGCT

LmddA-164-6
GGTCACAGCTGAGGACGGAACACAGCGTTCTGAGAAATGCAGCAAGCCCTGTGCT

Reference
(SEQ ID NO: 15)
CGAGTGTGCTATGGTCTGGGCATGGAGCACCTTCGAGGGGCGAGGGCCATCACCAGTGAC Lm-LLO-138-2
CGAGTGTGCTATGGTCTGGGCATGGAGCACCTTCGAGGGGCGAGGGCCATCACCAGTGAC Lm-LLO-138-3
CGAGTGTGCTATGGTCTGGGCATGGAGCACCTTCGAGGGGCGAGGGCCATCACCAGTGAC Lm-ddA-164-1
CGAGTGTGCTATGGTCTGGGCATGGAGCACCTTCGAGGGGCGAGGGCCATCACCAGTGAC LmddA164-2
CGAGTGTGCTATGGTCTGGGCATGGAGCACCTTCGAGGGGCGAGGGCCATCACCAGTGAC Lm-ddA-164-3
CGAGTGTGCTATGGTCTGGGCATGGAGCACCTTCGAGGGGCGAGGGCCATCACCAGTGAC LmddA164-4
CGAGTGTGCTATGGTCTGGGCATGGAGCACCTTCGAGGGGCGAGGGCCATCACCAGTGAC Lm-ddA-164-5
CGAGTGTGCTATGGTCTGGGCATGGAGCACCTTCGAGGGGCGAGGGCCATCACCAGTGAC LmddA-164-6
CGAGTGTGCTATGGTCTGGGCATGGAGCACCTTCGAGGGGCGAGGGCCATCACCAGTGAC Reference
(SEQ ID NO: 16)
AATGTCCAGGAGTTTGATGGCTGCAAGAAGATCTTTGGGAGCCTGGCATTTTTGCCGGAG Lm-LLO-138-2
AATGTCCAGGAGTTTGATGGCTGCAAGAAGATCTTTGGGAGCCTGGCATTTTTGCCGGAG Lm-LLO-138-3
AATGTCCAGGAGTTTGATGGCTGCAAGAAGATCTTTGGGAGCCTGGCATTTTTGCCGGAG Lm-ddA-164-1
AATGTCCAGGAGTTTGATGGCTGCAAGAAGATCTTTGGGAGCCTGGCATTTTTGCCGGAG LmddA164-2
AATGTCCAGGAGTTTGATGGCTGCAAGAAGATCTTTGGGAGCCTGGCATTTTTGCCGGAG Lm-ddA-164-3
AATGTCCAGGAGTTTGATGGCTGCAAGAAGATCTTTGGGAGCCTGGCATTTTTGCCGGAG LmddA164-4
AATGTCCAGGAGTTTGATGGCTGCAAGAAGATCTTTGGGAGCCTGGCATTTTTGCCGGAG Lm-ddA-164-5
AATGTCCAGGAGTTTGATGGCTGCAAGAAGATCTTTGGGAGCCTGGCATTTTTGCCGGAG LmddA-164-6
AATGTCCAGGAGTTTGATGGCTGCAAGAAGATCTTTGGGAGCCTGGCATTTTTGCCGGAG Reference
(SEQ ID No: 17)
AGCTTTGATGGGGACCCCTCCTCCGGCATTGCTCCGCTGAGGCCTGAGCAGCTCCAAGTG Lm-LLO-138-2
AGCTTTGATGGGGACCCCTCCTCCGGCATTGCTCCGCTGAGGCCTGAGCAGCTCCAAGTG Lm-LLO-138-3
AGCTTTGATGGGGACCCCTCCTCCGGCATTGCTCCGCTGAGGCCTGAGCAGCTCCAAGTG Lm-ddA-164-1
AGCTTTGATGGGGACCCCTCCTCCGGCATTGCTCCGCTGAGGCCTGAGCAGCTCCAAGTG LmddA164-2
AGCTTTGATGGGGACCCCTCCTCCGGCATTGCTCCGCTGAGGCCTGAGCAGCTCCAAGTG -continued

```
Lm-ddA-164-3
AGCTTTGATGGGGACCCCTCCTCCGGCATTGCTCCGCTGAGGCCTGAGCAGCTCCAAGTG

LmddA164-4
AGCTTTGATGGGGACCCCTCCTCCGGCATTGCTCCGCTGAGGCCTGAGCAGCTCCAAGTG

Lm-ddA-164-5
AGCTTTGATGGGGACCCCTCCTCCGGCATTGCTCCGCTGAGGCCTGAGCAGCTCCAAGTG

LmddA-164-6
AGCTTTGATGGGGACCCCTCCTCCGGCATTGCTCCGCTGAGGCCTGAGCAGCTCCAAGTG

Reference
                                                  (SEQ ID NO: 18)
TTCGAAACCCTGGAGGAGATCACAGGTTACCTGTACATCTCAGCATGGCCAGACAGTCTC Lm-LLO-138-2
TTCGAAACCCTGGAGGAGATCACAGGTTACCTGTACATCTCAGCATGGCCAGACAGTCTC Lm-LLO-138-3
TTCGAAACCCTGGAGGAGATCACAGGTTACCTGTACATCTCAGCATGGCCAGACAGTCTC Lm-ddA-164-1
TTCGAAACCCTGGAGGAGATCACAGGTTACCTGTACATCTCAGCATGGCCAGACAGTCTC LmddA164-2
TTCGAAACCCTGGAGGAGATCACAGGTTACCTGTACATCTCAGCATGGCCAGACAGTCTC Lm-ddA-164-3
TTCGAAACCCTGGAGGAGATCACAGGTTACCTGTACATCTCAGCATGGCCAGACAGTCTC LmddA164-4
TTCGAAACCCTGGAGGAGATCACAGGTTACCTGTACATCTCAGCATGGCCAGACAGTCTC Lm-ddA-164-5
TTCGAAACCCTGGAGGAGATCACAGGTTACCTGTACATCTCAGCATGGCCANACAGTCTC LmddA-164-6
TTCGAAACCCTGGAGGAGATCACAGGTTACCTGTACATCTCAGCATGGCCAGACAGTCT Reference
                                                  (SEQ ID NO: 19)
CGTGACCTCAGTGTCTTCCAGAACCTTCGAATCATTCGGGGACGGATTCTCCACGATGGC Lm-LLO-138-2
CGTGACCTCAGTGTCTTCCAGAACCTTCGAATCATTCGGGGACGGATTCTCCACGATGGC Lm-LLO-138-3
CGTGACCTCAGTGTCTTCCAGAACCTTCGAATCATTCGGGGACGGATTCTCCACGATGGC Lm-ddA-164-1
CGTGACCTCAGTGTCTTCCAGAACCTTCGAATCATTCGGGGACGGATTCTCCACGATGGC LmddA164-2
CGTGACCTCAGTGTCTTCCAGAACCTTCGAATCATTCGGGGACGGATTCTCCACGATGGC Lm-ddA-164-3
CGTGACCTCAGTGTCTTCCAGAACCTTCGAATCATTCGGGGACGGATTCTCCACGATGGC LmddA164-4
CGTGACCTCAGTGTCTTCCAAAACCTTCGAATCATTCGGGGACGGATTCTCCACGATGGC Lm-ddA-164-5
CGTGACCTCAGTGTCTTCCAAAACCTTCGAATCATTCGGGGACGGATTCTCCACGATGGC LmddA-164-6
CGTGACCTCAGTGTCTTCCAAAACCTTCGAATCATTCGGGGACGGATTCTCCACGATGGC Reference
                                                  (SEQ ID NO: 20)
GCGTACTCATTGACACTGCAAGGCCTGGGGATCCACTCGCTGGGGCTGCGCTCACTGCGG Lm-LLO-138-2
GCGTACTCATTGACACTGCAAGGCCTGGGGATCCACTCGCTGGGGCTGCGCTCACTGCGG Lm-LLO-138-3
GCGTACTCATTGACACTGCAAGGCCTGGGGATCCACTCGCTGGGGCTGCGCTCACTGCGG Lm-ddA-164-1
GCGTACTCATTGACACTGCAAGGCCTGGGGATCCACTCGCTGGGGCTGCGCTCACTGCGG
```

-continued

LmddA164-3
GCGTACTCATTGACACTGCAAGGCCTGGGGATCCACTCGCTGGGGCTGCGCTCACTGCGG

Lm-ddA-164-5
GCGTACTCATTGACACTGCAAGGCCTGGGGATCCACTCGCTGGGGCTGCGCTCACTGCGG

Lm-ddA-164-6
GCGTACTCATTGACACTGCAAGGCCTGGGGATCCACTCGCTGGGGCTGCGCTCACTGCGG

Reference
(SEQ ID NO: 21)
GAGCTGGGCAGTGGATTGGCTCTGATTCACCGCAACGCCCATCTCTGCTTTGTACACACT Lm-LLO-138-2
GAGCTGGGCAGTGGATTGGCTCTGATTCACCGCAACGCCCATCTCTGCTTTGTACACACT Lm-LLO-138-3
GAGCTGGGCAGTGGATTGGCTCTGATTCACCGCAACGCCCATCTCTGCTTTGTACACACT Lm-ddA-164-1
GAGCTGGGCAGTGGATTGGCTCTGATTCACCGCAACGCCCATCTCTGCTTTGTACACACT LmddA164-3
GAGCTGGGCAGTGGATTGGCTCTGATTCACCGCAACGCCCATCTCTGCTTTGTACACACT Lm-ddA-164-5
GAGCTGGGCAGTGGATTGGCTCTGATTCACCGCAACGCCCATCTCTGCTTTGTACACACT Lm-ddA-164-6
GAGCTGGGCAGTGGATTGGCTCTGATTCACCGCAACGCCCATCTCTGCTTTGTACACACT Reference
(SEQ ID NO: 22)
GTACCTTGGGACCAGCTCTTCCGGAACCCACATCAGGCCCTGCTCCACAGTGGGAACCGG Lm-LLO-138-2
GTACCTTGGGACCAGCTCTTCCGGAACCCACATCAGGCCCTGCTCCACAGTGGGAACCGG Lm-LLO-138-3
GTACCTTGGGACCAGCTCTTCCGGAACCCACATCAGGCCCTGCTCCACAGTGGGAACCGG Lm-ddA-164-1
GTACCTTGGGACCAGCTCTTCCGGAACCCACATCAGGCCCTGCTCCACAGTGGGAACCGG LmddA164-3
GTACCTTGGGACCAGCTCTTCCGGAACCCACATCAGGCCCTGCTCCACAGTGGGAACCGG Lm-ddA-164-5
GTACCTTGGGACCANCTCTTCCGGAACCCACATCAGGCCCTGCTCCACAGTGGGAACCGG Lm-ddA-164-6
GTACCTTGGGACCAGCTCTTCCGGAACCCACATCAGGCCCTGCTCCACAGTGGGAACCGG Reference
(SEQ ID NO: 23)
CCGGAAGAGGATTGTGGTCTCGAGGGCTTGGTCTGTAACTCACTGTGTGCCCACGGGCAC Lm-LLO-138-2
CCGGAAGAGGATTGTGGTCTCGAGGGCTTGGTCTGTAACTCACTGTGTGCCCACGGGCAC Lm-LLO-138-3
CCGGAAGAGGATTGTGGTCTCGAGGGCTTGGTCTGTAACTCACTGTGTGCCCACGGGCAC Lm-ddA-164-1
CCGGAAGAGGATTGTGGTCTCGAGGGCTTGGTCTGTAACTCACTGTGTGCCCACGGGCAC LmddA164-3
CCGGAAGAGGATTGTGGTCTCGAGGGCTTGGTCTGTAACTCACTGTGTGCCCACGGGCAC Lm-ddA-164-6
CCGGAAGAGGATTGTGGTCTCGAGGGCTTGGTCTGTAACTCACTGTGTGCCCACGGGCAC Reference
(SEQ ID NO: 24)
TGCTGGGGGCCAGGGCCCACCCAGTGTGTCAACTGCAGTCATTTCCTTCGGGGCCAGGAG Lm-LLO-138-2
TGCTGGGGGCCAGGGCCCACCCAGTGTGTCAACTGCAGTCATTTCCTTCGGGGCCAGGAG -continued

```
Lm-LLO-138-3
TGCTGGGGGCCAGGGCCCACCCAGTGTGTCAACTGCAGTCATTTCCTTCGGGGCCAGGAG

Lm-ddA-164-1
TGCTGGGGGCCAGGGCCCACCCAGTGTGTCAACTGCAGTCATTTCCTTCGGGGCCAGGAG

LmddA164-3
TGCTGGGGGCCAGGGCCCACCCAGTGTGTCAACTGCAGTCATTTCCTTCGGGGCCAGGAG

Lm-ddA-164-6
TGCTGGGGGCCAGGGCCCACCCA-------------------------------------
```

Alignment of IC1 (2114-3042 bp of Her-2-neu)

```
Reference
                                                      (SEQ ID NO: 25)
CGCCCAGCGGAGCAATGCCCAACCAGGCTCAGATGCGGATCCTAAAAGAGACGGAGC Lm-LLO-NY-2
CGCCCAGCGGAGCAATGCCCAACCAGGCTCAGATGCGGATCCTAAAAGAGACGGAGC Lm-LLO-138-4
CGCCCAGCGGAGCAATGCCCAACCAGGCTCAGATGCGGATCCTAAAAGAGACGGAGC Lm-ddA-164-2
CGCCCAGCGGAGCAATGCCCAACCAGGCTCAGATGCGGATCCTAAAAGAGACGGAGC Lm-ddA-164-3
CGCCCAGCGGAGCAATGCCCAACCAGGCTCAGATGCGGATCCTAAAAGAGACGGAGC Lm-ddA164-6
CGCCCAGCGGAGCAATGCCCAACCAGGCTCAGATGCGGATCCTAAAAGAGACGGAGC Reference
                                                      (SEQ ID NO: 26)
TAAGGAAGGTGAAGGTGCTTGGATCAGGAGCTTTTGGCACTGTCTACAAGGGCATCTGGA Lm-LLO-NY-1
TAAGGAAGGTGAAGGTGCTTGGATCAGGAGCTTTTGGCACTGTCTACAAGGGCATCTGGA Lm-LLO-NY-2
TAAGGAAGGTGAAGGTGCTTGGATCAGGAGCTTTTGGCACTGTCTACAAGGGCATCTGGA Lm-LLO-138-1
TAAGGAAGGTGAACGTGCTTGGATCAGGAGCTTTTGGCACTGTCTACAAGGGCATCTGGA Lm-LLO-138-2
TAAGGAAGGTGAAGGTGCTTGGATCAGGAGCTTTTGGCACTGTCTACAAGGGCATCTGGA Lm-LLO-138-3
TAAGGAAGGTGAAGGTGCTTGGATCAGGAGCTTTTGGCACTGTCTACAAGGGCATCTGGA Lm-LLO-138-4
TAAGGAAGGTGAAGGTGCTTGGATCAGGAGCTTTTGGCACTGTCTACAAGGGCATCTGGA Lm-ddA-164-1
TAAGGAAGGTGAAGGTGCTTGGATCAGGAGCTTTTGGCACTGTCTACAAGGGCATCTGGA Lm-ddA-164-2
TAAGGAAGGTGAAGGTGCTTGGATCAGGAGCTTTTGGCACTGTCTACAAGGGCATCTGGA Lm-ddA-164-3
TAAGGAAGGTGAAGGTGCTTGGATCAGGAGCTTTTGGCACTGTCTACAAGGGCATCTGGA Lm-ddA-164-4
TAAGGAAGGTGAAGGTGCTTGGATCAGGAGCTTTTGGCACTGTCTACAAGGGCATCTGGA Lm-ddA-164-5
TAAGGAAGGTGAAGGTGCTTGGATCAGGAGCTTTTGGCACTGTCTACAAGGGCATCTGGA Lm-ddA164-6
TAAGGAAGGTGAAGGTGCTTGGATCAGGAGCTTTTGGCACTGTCTACAAGGGCATCTGGA
```

-continued

Reference
(SEQ ID NO: 27)
TCCCAGATGGGAGAATGTGAAAATCCCCGTGGCTATCAAGGTGTTGAGAGAAAACACAT Lm-LLO-NY-1
TCCCAGATGGGAGAATGTGAAAATCCCCGTGGCTATCAAGGTGTTGAGAGAAAACACAT Lm-LLO-NY-2
TCCCAGATGGGAGAATGTGAAAATCCCCGTGGCTATCAAGGTGTTGAGAGAAAACACAT Lm-LLO-138-1
TCCCAGATGGGAGAATGTGAAAATCCCCGTGGCTATCAAGGTGTTGAGAGAAAACACAT Lm-LLO-138-2
TCCCAGATGGGAGAATGTGAAAATCCCCGTGGCTATCAAGGTGTTGAGAGAAAACACAT Lm-LLO-138-3
TCCCAGATGGGAGAATGTGAAAATCCCCGTGGCTATCAAGGTGTTGAGAGAAAACACAT Lm-LLO-138-4
TCCCAGATGGGAGAATGTGAAAATCCCCGTGGCTATCAAGGTGTTGAGAGAAAACACAT Lm-ddA-164-1
TCCCAGATGGGAGAATGTGAAAATCCCCGTGGCTATCAAGGTGTTGAGAGAAAACACAT Lm-ddA-164-2
TCCCAGATGGGAGAATGTGAAAATCCCCGTGGCTATCAAGGTGTTGAGAGAAAACACAT Lm-ddA-164-3
TCCCAGATGGGAGAATGTGAAAATCCCCGTGGCTATCAAGGTGTTGAGAGAAAACACAT Lm-ddA-164-4
TCCCAGATGGGAGAATGTGAAAATCCCCGTGGCTATCAAGGTGTTGAGAGAAAACACAT Lm-ddA-164-5
TCCCAGATGGGAGAATGTGAAAATCCCCGTGGCTATCAAGGTGTTGAGAGAAAACACAT Lm-ddA164-6
TCCCAGATGGGAGAATGTGAAAATCCCCGTGGCTATCAAGGTGTTGAGAGAAAACACAT Reference
(SEQ ID NO: 28)
CTCCTAAAGCCAACAAAGAAATTCTAGATGAAGCGTATGTGATGGCTGGTGTGGGTTCTC Lm-LLO-NY-1
CTCCTAAAGCCAACAAAGAAATTCTAGATGAAGCGTATGTGATGGCTGGTGTGGGTTCTC Lm-LLO-NY-2
CTCCTAAAGCCAACAAAGAAATTCTAGATGAAGCGTATGTGATGGCTGGTGTGGGTTCTC Lm-LLO-138-1
CTCCTAAAGCCAACAAAGAAATTCTAGATGAAGCGTATGTGATGGCTGGTGTGGGTTCTC Lm-LLO-138-2
CTCCTAAAGCCAACAAAGAAATTCTAGATGAAGCGTATGTGATGGCTGGTGTGGGTTCTC Lm-LLO-138-3
CTCCTAAAGCCAACAAAGAAATTCTAGATGAAGCGTATGTGATGGCTGGTGTGGGTTCTC lm-LLO-138-4
CTCCTAAAGCCAACAAAGAAATTCTAGATGAAGCGTATGTGATGGCTGGTGTGGGTTCTC Lm-ddA-164-1
CTCCTAAAGCCAACAAAGAAATTCTAGATGAAGCGTATGTGATGGCTGGTGTGGGTTCTC Lm-ddA-164-2
CTCCTAAAGCCAACAAAGAAATTCTAGATGAAGCGTATGTGATGGCTGGTGTGGGTTCTC Lm-ddA-164-3
CTCCTAAAGCCAACAAAGAAATTCTAGATGAAGCGTATGTGATGGCTGGTGTGGGTTCTC Lm-ddA-164-4
CTCCTAAAGCCAACAAAGAAATTCTAGATGAAGCGTATGTGATGGCTGGTGTGGGTTCTC Lm-ddA-164-5
CTCCTAAAGCCAACAAAGAAATTCTAGATGAAGCGTATGTGATGGCTGGTGTGGGTTCTC Lm-ddA164-6
CTCCTAAAGCCAACAAAGAAATTCTAGATGAAGCGTATGTGATGGCTGGTGTGGGTTCTC -continued Reference
(SEQ ID NO: 29)
CGTATGTGTCCCGCCTCCTGGGCATCTGCCTGACATCCACAGTACAGCTGGTGACACAGC Lm-LLO-NY-1
CGTATGTGTCCCGCCTCCTGGGCATCTGCCTGACATCCACAGTACAGCTGGTGACACAGC Lm-LLO-NY-2
CGTATGTGTCCCGCCTCCTGGGCATCTGCCTGACATCCACAGTACAGCTGGTGACACAGC Lm-LLO-138-1
CGTATGTGTCCCGCCTCCTGGGCATCTGCCTGACATCCACAGTACAGCTGGTGACACAGC Lm-LLO-138-2
CGTATGTGTCCCGCCTCCTGGGCATCTGCCTGACATCCACAGTACAGCTGGTGACACAGC Lm-LLO-138-3
CGTATGTGTCCCGCCTCCTGGGCATCTGCCTGACATCCACAGTACAGCTGGTGACACAGC Lm-LLO-138-4
CGTATGTGTCCCGCCTCCTGGGCATCTGCCTGACATCCACAGTACAGCTGGTGACACAGC Lm-ddA-164-1
CGTATGTGTCCCGCCTCCTGGGCATCTGCCTGACATCCACAGTACAGCTGGTGACACAGC Lm-ddA-164-2
CGTATGTGTCCCGCCTCCTGGGCATCTGCCTGACATCCACAGTACAGCTGGTGACACAGC Lm-ddA-164-3
CGTATGTGTCCCGCCTCCTGGGCATCTGCCTGACATCCACAGTACAGCTGGTGACACAGC Lm-ddA-164-4
CGTATGTGTCCCGCCTCCTGGGCATCTGCCTGACATCCACAGTACAGCTGGTGACACAGC Lm-ddA-164-5
CGTATGTGTCCCGCCTCCTGGGCATCTGCCTGACATCCACAGTACAGCTGGTGACACAGC Lm-ddA164-6
CGTATGTGTCCCGCCTCCTGGGCATCTGCCTGACATCCACAGTACAGCTGGTGACACAGC Reference
(SEQ ID NO: 30)
TTATGCCCTACGGCTGCCTTCTGGACCATGTCCGAGAACACCGAGGTCGCCTAGGCTCCC Lm-LLO-NY-1
TTATGCCCTACGGCTGCCTTCTGGACCATGTCCGAGAACACCGAGGTCGCCTAGGCTCCC Lm-LLO-NY-2
TTATGCCCTACGGCTGCCTTCTGGACCATGTCCGAGAACACCGAGGTCGCCTAGGCTCCC Lm-LLO-138-1
TTATGCCCTACGGCTGCCTTCTGGACCATGTCCGAGAACACCGAGGTCGCCTAGGCTCCC Lm-LLO-138-2
TTATGCCCTACGGCTGCCTTCTGGACCATGTCCGAGAACACCGAGGTCGCCTAGGCTCCC Lm-LLO-138-3
TTATGCCCTACGGCTGCCTTCTGGACCATGTCCGAGAACACCGAGGTCGCCTAGGCTCCC Lm-LLO-138-4
TTATGCCCTACGGCTGCCTTCTGGACCATGTCCGAGAACACCGAGGTCGCCTAGGCTCCC Lm-ddA-164-1
TTATGCCCTACGGCTGCCTTCTGGACCATGTCCGAGAACACCGAGGTCGCCTAGGCTCCC Lm-ddA-164-2
TTATGCCCTACGGCTGCCTTCTGGACCATGTCCGAGAACACCGAGGTCGCCTAGGCTCCC Lm-ddA-164-3
TTATGCCCTACGGCTGCCTTCTGGACCATGTCCGAGAACACCGAGGTCGCCTAGGCTCCC Lm-ddA-164-4
TTATGCCCTACGGCTGCCTTCTGGACCATGTCCGAGAACACCGAGGTCGCCTAGGCTCCC Lm-ddA-164-5
TTATGCCCTACGGCTGCCTTCTGGACCATGTCCGAGAACACCGAGGTCGCCTAGGCTCCC Lm-ddA164-6
TTATGCCCTACGGCTGCCTTCTGGACCATGTCCGAGAACACCGAGGTCGCCTAGGCTCCC -continued

```
Reference
                                                    (SEQ ID NO: 31)
AGGACCTGCTCAACTGGTGTGTTCAGATTGCCAAGGGGATGAGCTACCTGGAGGACGTGC Lm-LLO-NY-1
AGGACCTGCTCAACTGGTGTGTTCAGATTGCCAAGGGGATGAGCTACCTGGAGGACGTGC Lm-LLO-NY-2
AGGACCTGCTCAACTGGTGTGTTCAGATTGCCAAGGGGATGAGCTACCTGGAGGACGTGC Lm-LLO-138-1
AGGACCTGCTCAACTGGTGTGTTCAGATTGCCAAGGGGATGAGCTACCTGGAGGACGTGC Lm-LLO-138-2
AGGACCTGCTCAACTGGTGTGTTCAGATTGCCAAGGGGATGAGCTACCTGGAGGACGTGC Lm-LLO-138-3
AGGACCTGCTCAACTGGTGTGTTCAGATTGCCAAGGGGATGAGCTACCTGGAGGACGTGC Lm-LLO-138-4
AGGACCTGCTCAACTGGTGTGTTCAGATTGCCAAGGGGATGAGCTACCTGGAGGACGTGC Lm-ddA-164-1
AGGACCTGCTCAACTGGTGTGTTCAGATTGCCAAGGGGATGAGCTACCTGGAGGACGTGC Lm-ddA-164-2
AGGACCTGCTCAACTGGTGTGTTCAGATTGCCAAGGGGATGAGCTACCTGGAGGACGTGC Lm-ddA-164-3
AGGACCTGCTCAACTGGTGTGTTCAGATTGCCAAGGGGATGAGCTACCTGGAGGACGTGC Lm-ddA-164-4
AGGACCTGCTCAACTGGTGTGTTCAGATTGCCAAGGGGATGAGCTACCTGGAGGACGTGC Lm-ddA-164-5
AGGACCTGCTCAACTGGTGTGTTCAGATTGCCAAGGGGATGAGCTACCTGGAGGACGTGC Lm-ddA164-6
AGGACCTGCTCAACTGGTGTGTTCAGATTGCCAAGGGGATGAGCTACCTGGAGGACGTGC Reference
                                                    (SEQ ID NO: 32)
GGCTTGTACACAGGGACCTGGCTGCCCGGAATGTGCTAGTCAAGAGTCCCAACCACGTCA Lm-LLO-NY-1
GGCTTGTACACAGGGACCTGGCTGCCCGGAATGTGCTAGTCAAGAGTCCCAACCACGTCA Lm-LLO-NY-2
GGCTTGTACACAGGGACCTGGCTGCCCGGAATGTGCTAGTCAAGAGTCCCAACCACGTCA Lm-LLO-138-1
GGCTTGTACACAGGGACCTGGCTGCCCGGAATGTGCTAGTCAAGAGTCCCAACCACGTCA Lm-LLO-138-2
GGCTTGTACACAGGGACCTGGCTGCCCGGAATGTGCTAGTCAAGAGTCCCAACCACGTCA Lm-LLO-138-3
GGCTTGTACACAGGGACCTGGCTGCCCGGAATGTGCTAGTCAAGAGTCCCAACCACGTCA Lm-LLO-138-4
GGCTTGTACACAGGGACCTGGCTGCCCGGAATGTGCTAGTCAAGAGTCCCAACCACGTCA Lm-ddA-164-1
GGCTTGTACACAGGGACCTGGCTGCCCGGAATGTGCTAGTCAAGAGTCCCAACCACGTCA Lm-ddA-164-2
GGCTTGTACACAGGGACCTGGCTGCCCGGAATGTGCTAGTCAAGAGTCCCAACCACGTCA Lm-ddA-164-4
GGCTTGTACACAGGGACCTGGCTGCCCGGAATGTGCTAGTCAAGAGTCCCAACCACGTCA Lm-ddA-164-3
GGCTTGTACACAGGGACCTGGCTGCCCGGAATGTGCTAGTCAAGAGTCCCAACCACGTCA Lm-ddA-164-5
GGCTTGTACACAGGGACCTGGCTGCCCGGAATGTGCTAGTCAAGAGTCCCAACCACGTCA Lm-ddA164-6
GGCTTGTACACAGGGACCTGGCTGCCCGGAATGTGCTAGTCAAGAGTCCCAACCACGTCA
```

-continued

Reference
(SEQ ID NO: 33)
AGATTACAGATTTCGGGCTGGCTCGGCTGCTGGACATTGATGAGACAGAGTACCATGCAG Lm-LLO-NY-1
AGATTACAGATTTCGGGCTGGCTCGGCTGCTGGACATTGATGAGACAGAGTACCATGCAG Lm-LLO-NY-2
AGATTACAGATTTCGGGCTGGCTCGGCTGCTGGACATTGATGAGACAGAGTACCATGCAG Lm-LLO-138-1
AGATTACAGATTTCGGGCTGGCTCGGCTGCTGGACATTGATGAGACAGAGTACCATGCAG Lm-LLO-138-2
AGATTACAGATTTCGGGCTGGCTCGGCTGCTGGACATTGATGAGACAGAGTACCATGCAG Lm-LLO-138-3
AGATTACAGATTTCGGGCTGGCTCGGCTGCTGGACATTGATGAGACAGAGTACCATGCAG Lm-LLO-138-4
AGATTACAGATTTCGGGCTGGCTCGGCTGCTGGACATTGATGAGACAGAGTACCATGCAG Lm-ddA-164-1
AGATTACAGATTTCGGGCTGGCTCGGCTGCTGGACATTGATGAGACAGAGTACCATGCAG Lm-ddA-164-2
AGATTACAGATTTCGGGCTGGCTCGGCTGCTGGACATTGATGAGACAGAGTACCATGCAG Lm-ddA-164-3
AGATTACAGATTTCGGGCTGGCTCGGCTGCTGGACATTGATGAGACAGAGTACCATGCAG Lm-ddA-164-4
AGATTACAGATTTCGGGCTGGCTCGGCTGCTGGACATTGATGAGACAGAGTACCATGCAG Lm-ddA-164-5
AGATTACAGATTTCGGGCTGGCTCGGCTGCTGGACATTGATGAGACAGAGTACCATGCAG Lm-ddA164-6
AGATTACAGATTTCGGGCTGGCTCGGCTGCTGGACATTGATGAGACAGAGTACCATGCAG Reference
(SEQ ID NO: 34)
ATGGGGGCAAGGTGCCCATCAAATGGATGGCATTGGAATCTATTCTCAGACGCCGGTTCA Lm-LLO-NY-1
ATGGGGGCAAGGTGCCCATCAAATGGATGGCATTGGAATCTATTCTCAGACGCCGGTTCA Lm-LLO-NY-2
ATGGGGGCAAGGTGCCCATCAAATGGATGGCATTGGAATCTATTCTCAGACGCCGGTTCA Lm-LLO-138-1
ATGGGGGCAAGGTGCCCATCAAATGGATGGCATTGGAATCTATTCTCAGACGCCGGTTCA Lm-LLO-138-2
ATGGGGGCAAGGTGCCCATCAAATGGATGGCATTGGAATCTATTCTCAGACGCCGGTTCA Lm-LLO-138-3
ATGGGGGCAAGGTGCCCATCAAATGGATGGCATTGGAATCTATTCTCAGACGCCGGTTCA Lm-LLO-138-4
ATGGGGGCAAGGTGCCCATCAAATGGATGGCATTGGAATCTATTCTCAGACGCCGGTTCA Lm-ddA-164-1
ATGGGGGCAAGGTGCCCATCAAATGGATGGCATTGGAATCTATTCTCAGACGCCGGTTCA Lm-ddA-164-2
ATGGGGGCAAGGTGCCCATCAAATGGATGGCATTGGAATCTATTCTCAGACGCCGGTTCA Lm-ddA-164-3
ATGGGGGCAAGGTGCCCATCAAATGGATGGCATTGGAATCTATTCTCAGACGCCGGTTCA Lm-ddA-164-4
ATGGGGGCAAGGTGCCCATCAAATGGATGGCATTGGAATCTATTCTCAGACGCCGGTTCA Lm-ddA-164-5
ATGGGGGCAAGGTGCCCATCAAATGGATGGCATTGGAATCTATTCTCAGACGCCGGTTCA Lm-ddA-164-6
ATGGGGGCAAGGTGCCCATCAAATGGATGGCATTGGAATCTATTCTCAGACGCCGGTTCA -continued Reference
(SEQ ID NO: 35)
CCCATCAGAGTGATGTGTGGAGCTATGGAGTGACTGTGTGGGAGCTGATGACTTTTGGGG Lm-LLO-NY-1
CCCATCAGAGTGATGTGTGGAGCTATGGAGTGACTGTGTGGGAGCTGATGACTTTTGGGG Lm-LLO-NY-2
CCCATCAGAGTGATGTGTGGAGCTATGGAGTGACTGTGTGGGAGCTGATGACTTTTGGGG Lm-LLO-138-1
CCCATCAGAGTGATGTGTGGAGCTATGGAGTGACTGTGTGGGAGCTGATGACTTTTGGGG Lm-LLO-138-2
CCCATCAGAGTGATGTGTGGAGCTATGGAGTGACTGTGTGGGAGCTGATGACTTTTGGGG Lm-LLO-138-3
CCCATCAGAGTGATGTGTGGAGCTATGGAGTGACTGTGTGGGAGCTGATGACTTTTGGGG Lm-LLO-138-4
CCCATCAGAGTGATGTGTGGAGCTATGGAGTGACTGTGTGGGAGCTGATGACTTTTGGGG Lm-ddA-164-1
CCCATCAGAGTGATGTGTGGAGCTATGGAGTGACTGTGTGGGAGCTGATGACTTTTGGGG Lm-ddA-164-2
CCCATCAGAGTGATGTGTGGAGCTATGGAGTGACTGTGTGGGAGCTGATGACTTTTGGGG Lm-ddA-164-3
CCCATCAGAGTGATGTGTGGAGCTATGGAGTGACTGTGTGGGAGCTGATGACTTTTGGGG Lm-ddA-164-4
CCCATCAGAGTGATGTGTGGAGCTATGGAGTGACTGTGTGGGAGCTGATGACTTTTGGGG Lm-ddA-164-5
CCCATCAGAGTGATGTGTGGAGCTATGGAGTGACTGTGTGGGAGCTGATGACTTTTGGGG Lm-ddA164-6
CCCATCAGAGTGATGTGTGGAGCTATGGAGTGACTGTGTGGGAGCTGATGACTTTTGGGG Reference
(SEQ ID NO: 36)
CCAAACCTTACGATGGAATCCCAGCCCGGGAGATCCCTGATTTGCTGGAGAAGGGAGAA Lm-LLO-NY-1
CCAAACCTTACGATGGAATCCCAGCCCGGGAGATCCCTGATTTGCTGGAGAAGGGAGAA Lm-LLO-NY-2
CCAAACCTTACGATGGAATCCCAGCCCGGGAGATCCCTGATTTGCTGGAGAAGGGAGAA Lm-LLO-138-1
CCAAACCTTACGATGGAATCCCAGCCCGGGAGATCCCTGATTTGCTGGAGAAGGGAGAA Lm-LLO-138-3
CCAAACCTTACGATGGAATCCCAGCCCGGGAGATCCCTGATTTGCTGGAGAAGGGAGAA Lm-LLO-138-4
CCAAACCTTACGATGNAATCCCAGCCCGGGAGATCCCTGATTTGCTGGAGAAGGGAGAA Lm-ddA164-6
CCAAACCTTACGATGGAATCCCAGCCCGGGAGATCCCTGATTTGCTGGAGAAGGGAGAA Lm-ddA-164-2
CCAAACCTTACGATGGAATCCCAGCCCGGGAGATCCCTGATTTGCTGGAGAAGGGAGAA Lm-LLO-138-2
CCAAACCTTACGATGGAATCCCAGCCCGGGAGATCCCTGATTTGCTGGAGAAGGGAGAA Lm-ddA-164-3
CCAAACCTTACGATGGAATCCCAGCCCGGGAGATCCCTGATTTGCTGGAGAAGGGAGAA Lm-ddA-164-5
CCAAACCTTACGATGGAATCCCAGCCCGGGAGATCCCTGATTTGCTGGAGAAGGGAGAA Lm-ddA-164-1
CCAAACCTTACGATGGAATCCCAGCCCGGGAGATCCCTGATTTGCTGGAGAAGGGAGAA Lm-ddA-164-4
CCAAACCTTACGATGGAATCCCAGCCCGGGAGATCCCTGATTTGCTGGAGAAGGGAGAA -continued Reference
(SEQ ID NO: 37)
CGCCTACCTCAGCCTCCAATCTGCACCATTGATGTCTACATGATTATGGTCAAATGTT Lm-LLO-NY-1
CGCCTACCTCAGCCTCCAATCTGCACCATTGATGTCTACATGATTATGGTCAAATGTT Lm-LLO-NY-2
CGCCTACCTCAGCCTCCAATCTGCACCATTGATGTCTACATGATTATGGTCAAATGTT Lm-LLO-138-1
CGCCTACCTCAGCCTCCAATCTGCACCATTGATGTCTACATGATTATGGTCAAATGTT Lm-LLO-138-2
CGCCTACCTCAGCCTCCAATCTGCACCATTGATGTCTACATGATTATGGTCAAATGTT Lm-LLO-138-3
CGCCTACCTCAGCCTCCAATCTGCACCATTGATGTCTACATGATTATGGTCAAATGTT Lm-LLO-138-4
CGCCTACCTCAGCCTCCAATCTGCACCATTGATGTCTACATGATTATGGTCAAATGTT Lm-ddA-164-1
CGCCTACCTCAGCCTCCAATCTGCACCATTGATGTCTACATGATTATGGTCAAATGTT Lm-ddA-164-2
CGCCTACCTCAGCCTCCAATCTGCACCATTGATGTCTACATGATTATGGTCAAATGTT Lm-ddA-164-3
CGCCTACCTCAGCCTCCAATCTGCACCATTGATGTCTACATGATTATGGTCAAATGTT Lm-ddA-164-4
CGCCTACCTCAGCCTCCAATCTGCACCATTGATGTCTACATGATTATGGTCAAATGTT Lm-ddA-164-5
CGCCTACCTCAGCCTCCAATCTGCACCATTGATGTCTACATGATTATGGTCAAATGTT Lm-ddA164-6
CGCCTACCTCAGCCTCCAATCTGCACCATTGATGTCTACATGATTATGGTCAAATGTT Reference
(SEQ ID NO: 38)
GGATGATTGACTCTGAATGTCGCCCGAGATTCCGGGAGTTGGTGTCAGAATTTT Lm-LLO-NY-1
GGATGATTGACTCTGAATGTCGCCCGAGATTCCGGGAGTTGGTGTCAGAATTTT Lm-LLO-NY-2
GGATGATTGACTCTGAATGTCGCCCGAGATTCCGGGAGTTGGTGTCAGAATTTT Lm-LLO-138-2
GGATGATTGACTCTGAATGTCCCCCGAGATTCCGGGAGTTGGTGTCAAAATTTT Lm-LLO-138-3
GGATGATTGACTCTGAATGTCGCCCGAGATTCCGGGAGTTGGTGTCAGAATTTT Lm-LLO-138-4
GGATGATTGACTCTGAATGTCGCCCGAGATTCCGGGAGTTGGTGTCAGAATTTT Lm-ddA-164-1
GGATGATTGACTCTGAATGTCGCCCGAGATTCCGGGAGTTGGTGTCAGAATTTT Lm-ddA-164-2
GGATGATTGACTCTGAATGTCGCCCGAGATTCCGGGAGTTGGTGTCAGAATTTT Lm-ddA-164-3
GGATGATTGACTCTGAATGTCGCCCGAGATTCCGGGAGTTGGTGTCAGAATTTT Lm-ddA-164-5
GGATGATTGACTCTGAATGTCGCCCGAGATTCCGGGAGTTGGTGTCAGAATTTT Lm-ddA-164-4
GGATGATTGACTCTGAATGTCGCCCGAGATTCCGGGAGTTGGTGTCAGAATTTT Lm-ddA164-6
GGATGATTGACTCTGAATGTCGCCCGAGATTCCGGGAGTTGGTGTCAGAATTTT

```
Reference
                                                              (SEQ ID NO: 39)
CACGTATGGCGAGGGACCCCCAGCGTTTTGTGGTCATCCAGAACGAGGACTT Lm-LLO-NY-1
CACGTATGGCGAGGGACCCCCAGCGTTTTGTGGTCATCCAGAACGAGGACTT Lm-LLO-NY-2
CACGTATGGCGAGGGACCCCCAGCGTTTTGTGGTCATCCAGAACGAGGACTT Lm-LLO-138-2
CACGTATGGCGAGGGACCCCCAGCGTTTTGTGGTCATCCAGAACGAGGACTT Lm-LLO-138-3
CACGTATGGCGAGGGACCCCCAGCGTTTTGTGGTCATCCAGAACGAGGACTT Lm-LLO-138-4
CACGTATGGCGAGGGACCCCCAGCGTTTTGTGGTCATCCAGAACGAGGACTT Lm-ddA-164-1
CACGTATGGCGAGGGACCCCCAGCGTTTTGTGGTCATCCAGAACGAGGACTT Lm-ddA-164-2
CACGTATGGCGAGGGACCCCCAGCGTTTTGTGGTCATCCAGAACGAGGACTT Lm-ddA-164-3
CACGTATGGCGAGGGACCCCCAGCGTTTTGTGGTCATCCAGAACGAGGACTT Lm-ddA-164-5
CACGTATGGCGAGGGACCCCCAGCGTTTTGTGGTCATCCAGAACGAGGACTT Lm-ddA-164-6
CACGTATGGCGAGGGACCCCCAGCGTTTTGTGGTCATCCAGAACGAGGACTT
```

Alignment of EC1 (399-758 bp of Her-2-neu)

```
Reference
                                                              (SEQ ID NO: 40)
CCCAGGCAGAACCCCAGAGGGGCTGCGGGAGCTGCAGCTTCGAAGTCTCACAGAGATCCT Lm-LLO-138-1
CCCAGGCAGAACCCCAGAGGGGCTGCGGGAGCTGCAGCTTCGAAGTCTCACAGAGATCCT Lm-LLO-138-2
CCCAGGCAGAACCCCAGAGGGGCTGCGGGAGCTGCAGCTTCGAAGTCTCACAGAGATCCT Lm-ddA-164-1
CCCAGGCAGAACCCCAGAGGGGCTGCGGGAGCTGCAGCTTCGAAGTCTCACAGAGATCCT LmddA-164-2
CCCAGGCAGAACCCCAGAGGGGCTGCGGGAGCTGCAGCTTCGAAGTCTCACAGAGATCCT LmddA-164-3
CCCAGGCAGAACCCCAGAGGGGCTGCGGGAGCTGCAGCTTCGAAGTCTCACAGAGATCCT LmddA164-4
CCCAGGCAGAACCCCAGAGGGGCTGCGGGAGCTGCAGCTTCGAAGTCTCACAGAGATCCT Reference
                                                              (SEQ ID NO: 41)
GAAGGGAGGAGTTTTGATCCGTGGGAACCCTCAGCTCTGCTACCAGGACATGGTTTTGTG Lm-LLO-138-1
GAAGGGAGGAGTTTTGATCCGTGGGAACCCTCAGCTCTGCTACCAGGACATGGTTTTGTG Lm-LLO-138-2
GAAGGGAGGAGTTTTGATCCGTGGGAACCCTCAGCTCTGCTACCAGGACATGGTTTTGTG Lm-ddA-164-1
GAAGGGAGGAGTTTTGATCCGTGGGAACCCTCAGCTCTGCTACCAGGACATGGTTTTGTG LmddA-164-2
GAAGGGAGGAGTTTTGATCCGTGGGAACCCTCAGCTCTGCTACCAGGACATGGTTTTGTG LmddA-164-3
GAAGGGAGGAGTTTTGATCCGTGGGAACCCTCAGCTCTGCTACCAGGACATGGTTTTGTG
```

-continued

```
LmddA164-4
GAAGGGAGGAGTTTTGATCCGTGGGAACCCTCAGCTCTGCTACCAGGACATGGTTTTGTG

Reference
                                                     (SEQ ID NO: 42)
CCGGGCCTGTCCACCTTGTGCCCCCGCCTGCAAAGACAATCACTGTTGGGGTGAGAGTCC Lm-LLO-138-1
CCGGGCCTGTCCACCTTGTGCCCCCGCCTGCAAAGACAATCACTGTTGGGGTGAGAGTCC Lm-LLO-138-2
CCGGGCCTGTCCACCTTGTGCCCCCGCCTGCAAAGACAATCACTGTTGGGGTGAGAGTCC Lm-ddA-164-1
CCGGGCCTGTCCACCTTGTGCCCCCGCCTGCAAAGACAATCACTGTTGGGGTGAGAGTCC LmddA-164-2
CCGGGCCTGTCCACCTTGTGCCCCCGCCTGCAAAGACAATCACTGTTGGGGTGAGAGTCC LmddA-164-3
CCGGGCCTGTCCACCTTGTGCCCCCGCCTGCAAAGACAATCACTGTTGGGGTGAGAGTCC LmddA164-4
CCGGGCCTGTCCACCTTGTGCCCCCGCCTGCAAAGACAATCACTGTTGGGGTGAGAGTCC Reference
                                                     (SEQ ID NO: 43)
GGAAGACTGTCAGATCTTGACTGGCACCATCTGTACCAGTGGTTGTGCCCGGTGCAAGGG Lm-LLO-138-1
GGAAGACTGTCAGATCTTGACTGGCACCATCTGTACCAGTGGTTGTGCCCGGTGCAAGGG Lm-LLO-138-2
GGAAGACTGTCAGATCTTGACTGGCACCATCTGTACCAGTGGTTGTGCCCGGTGCAAGGG Lm-ddA-164-1
GGAAGACTGTCAGATCTTGACTGGCACCATCTGTACCAGTGGTTGTGCCCGGTGCAAGGG LmddA-164-2
GGAAGACTGTCAGATCTTGACTGGCACCATCTGTACCAGTGGTTGTGCCCGGTGCAAGGG LmddA-164-3
GGAAGACTGTCAGATCTTGACTGGCACCATCTGTACCAGTGGTTGTGCCCGGTGCAAGGG LmddA164-4
GGAAGACTGTCAGATCTTGACTGGCACCATCTGTACCAGTGGTTGTGCCCGGTGCAAGGG Reference
                                                     (SEQ ID NO: 44)
CCGGCTGCCCACTGACTGCTGCCATGAGCAGTGTGCCGCAGGCTGCACGGGCCCAAGCA Lm-LLO-138-1
CCGGCTGCCCACTGACTGCTGCCATGAGCAGTGTGCCGCAGGCTGCACGGGCCCAAGCA Lm-LLO-138-2
CCGGCTGCCCACTGACTGCTGCCATGAGCAGTGTGCCGCAGGCTGCACGGGCCCAAGCA Lm-ddA-164-1
CCGGCTGCCCACTGACTGCTGCCATGAGCAGTGTGCCGCAGGCTGCACGGGCCCAAGCA LmddA-164-2
CCGGCTGCCCACTGACTGCTGCCATGAGCAGTGTGCCGCAGGCTGCACGGGCCCAAGTA LmddA-164-3
CCGGCTGCCCACTGACTGCTGCCATGAGCAGTGTGCCGCAGGCTGCACGGGCCCAAGTA LmddA164-4
CCGGCTGCCCACTGACTGCTGCCATGAGCAGTGTGCCGCAGGCTGCACGGGCCCAAGTA
```

Example 7

Figure 6:
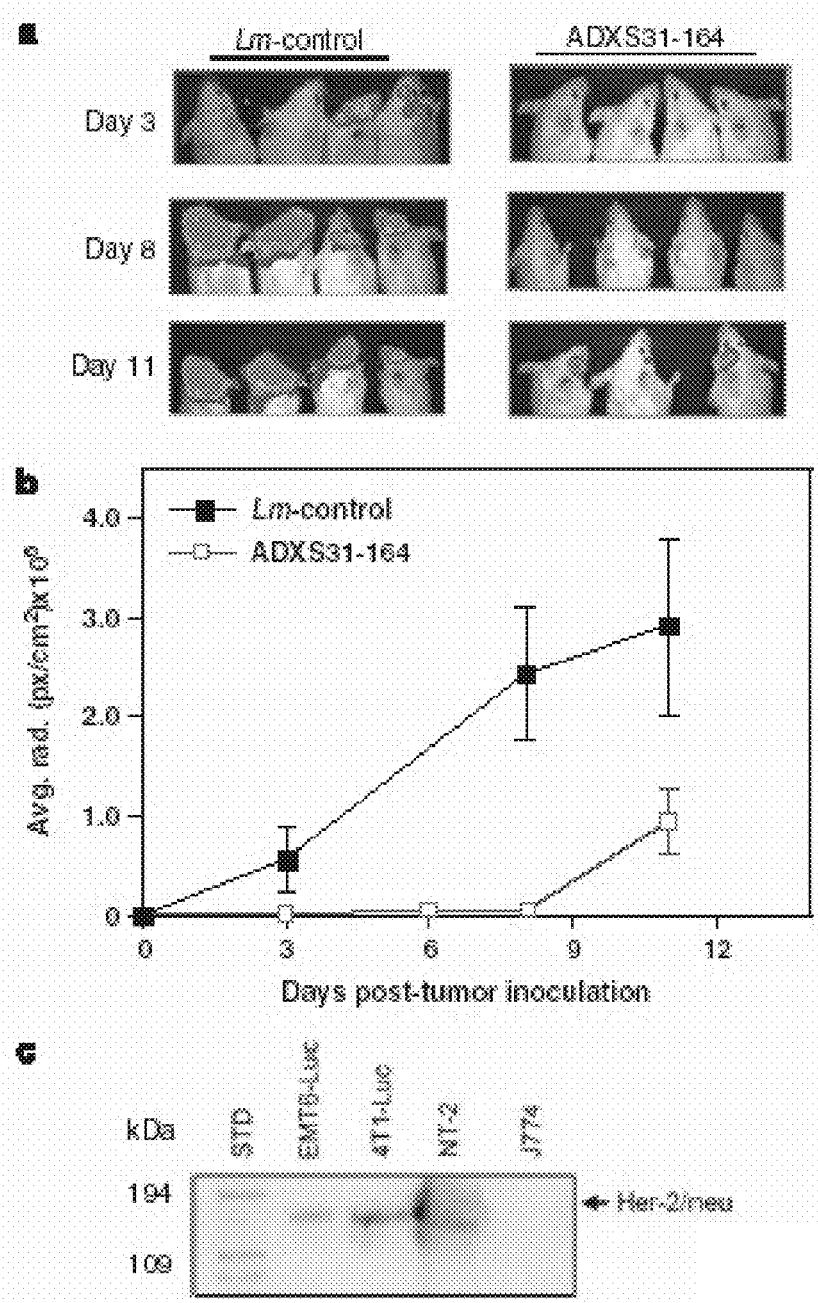
FIG. 6. Vaccination with ADXS31-164 can delay the growth of a breast cancer cell line in the brain. Balb/c mice were immunized thrice with ADXS31-164 or a control *Listeria* vaccine. EMT6-Luc cells (5,000) were injected intracranially in anesthetized mice. (A) Ex vivo imaging of the mice was performed on the indicated days using a Xenogen X-100 CCD camera. (B) Pixel intensity was graphed as number of photons per second per cm2 of surface area; this is shown as average radiance. (C) Expression of Her2/neu by EMT6-Luc cells, 4T1-Luc and NT-2 cell lines was detected by Western blots, using an anti-Her2/neu antibody. J774.A2 cells, a murine macrophage like cell line was used as a negative control.

Peripheral Immunization with ADXS31-164 can Delay the Growth of a Metastatic Breast Cancer Cell Line in the Brain Mice were immunized IP with ADXS31-164 or irrelevant Lm-control vaccines and then implanted intra-cranially with 5,000 EMT6-Luc tumor cells, expressing luciferase and low levels of Her2/neu (FIG. 6C). Tumors were monitored at different times post-inoculation by ex vivo imaging of anesthetized mice. On day 8 post-tumor inoculation tumors were detected in all control animals, but none of the mice in ADXS31-164 group showed any detectable tumors (FIGS. 6A and B). ADXS31-164 could clearly delay the onset of these tumors, as on day 11 post-tumor inoculation all mice in negative control group had already succumbed to their tumors, but all mice in ADXS31-164 group were still alive and only showed small signs of tumor growth. These results strongly suggest that the immune responses obtained with the peripheral administration of ADXS31-164 could possibly reach the central nervous system and that LmddA-based vaccines might have a potential use for treatment of CNS tumors.

Example 8

Treatment of Canine Osteasarcoma by Immunization with ADXS31-164

Canine Osteosarcoma is a cancer of long (leg) bones that is a leading killer of large dogs over the age of 10 years. Standard treatment is amputation immediately after diagnosis, followed by chemotherapy. Invariably, however, the cancer metastasizes to the lungs. With chemotherapy, dogs survive about 18 months compared to 6-12 months, without treatment. The HER2 antigen is believed to be present in up to 50% of osteosarcoma. ADXS31-164 creates an immune attack on cells expressing this antigen and has been developed to treat human breast cancer.

Dogs with a histological diagnosis of osteosarcoma and evidence of expression of HER2/neu by malignant cells are eligible for enrollment.

Canine Osteosarcoma Trial

In the first regiment the limbs are amputated, followed by round of chemotherapy treatment. 3 doses of Her-2 vaccine are subsequently administered with or without a 6 month interval booster.

All dogs will receive 4 weeks of carboplatin therapy. Four weeks after the last carboplatin dose, dogs will receive ADXS-HER2 once every three weeks for a total of 3 doses. Group 1 (3 dogs) receive $1 \times 10^8$ CFU per dose, Group 2 (3 dogs) each receive $5 \times 10^8$ CFU per dose and Group 3 (3 dogs) will receive $1 \times 10^9$ CFU per dose. Additional dogs may be added to a Group to gather more data should if a potentially dose limiting toxicities, be observed. Therefore 9-18 dogs may be treated in the initial study.

In the second regiment, the same as the first regiment is repeated with the exception that only a single dose of vaccine is administered before chemotherapy (1 month before) for a total of 4 doses.

Further, in both regiments a single dose is administered a month after chemotherapy.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating a Her-2/neu-expressing tumor growth or cancer in a non-human animal, the method comprising the step of administering to said non-human animal a recombinant *Listeria* strain having mutations in the D-alanine racemase (Dal) gene and the D-amino acid transferase (Dat) gene, said recombinant *Listeria* strain comprising a nucleic acid encoding a first and a second open reading frame, wherein said first open reading frame encodes a recombinant polypeptide comprising SEQ ID NO: 2 fused to an additional polypeptide, and wherein said second open reading frame encodes a metabolic enzyme that complements said mutations, wherein said Her-2/neu-expressing tumor growth or cancer is osteosarcoma, and wherein said recombinant *Listeria* lacks the actA virulence gene.

2. The method of claim 1, wherein said non-human animal is a dog.

3. The method of claim 1, wherein administering said fusion polypeptide to a subject having said osteosarcoma prevents escape mutations within said tumor or cancer.

4. The method of claim 1, wherein said Her-2/neu chimeric antigen comprises at least 5, 9, 13, 14, or 17 of the mapped human MHC-class I epitopes.

5. The method of claim 1, wherein said nucleic acid molecule is integrated into the *Listeria* genome.

6. The method of claim 1, wherein said nucleic acid molecule is in a plasmid in said recombinant *Listeria* strain.

7. The method of claim 6, wherein said plasmid is stably maintained in said recombinant *Listeria* strain in the absence of antibiotic selection.

8. The method of claim 6, wherein said plasmid does not confer antibiotic resistance upon said recombinant *Listeria*.

9. The method of claim 1, wherein said recombinant *Listeria* strain is attenuated.

10. The method of claim 1, wherein said additional polypeptide is selected from the group consisting of: a) non-hemolytic LLO protein or N-terminal fragment, b) a PEST sequence, or c) an ActA fragment.

11. The method of claim 1, wherein said metabolic enzyme encoded by said second open reading frame is an amino acid metabolism enzyme.

12. The method of claim 11, wherein said amino acid metabolism enzyme encoded by said second open reading frame is an alanine racemase enzyme or a D-amino acid transferase enzyme.

13. The method of claim 1, wherein said nucleic acid molecule further comprises a third open reading frame.

14. The method of claim 13, wherein said third open reading frame encodes a metabolic enzyme, wherein said metabolic enzyme is a D-amino acid transferase enzyme or an alanine racemase enzyme.

15. The method of claim 1, wherein said recombinant *Listeria* strain has been passaged through an animal host.

16. The method of claim 1, further comprising an independent adjuvant.

17. The method of claim 16, wherein said adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

18. The method of claim 1, wherein said osteosarcoma cancer is canine osteosarcoma.

19. A method of preventing a Her-2/neu-expressing tumor growth or cancer in a non-human animal, the method comprising the step of administering to said non-human animal a recombinant *Listeria* having mutations in the D-alanine racemase (Dal) gene and the D-amino acid transferase (Dat) gene, said recombinant *Listeria* comprising a nucleic acid encoding a first and a second open reading frame, wherein said first open reading frame encodes a recombinant polypeptide comprising SEQ ID NO: 2 fused to an additional polypeptide, and wherein said second open reading frame encodes a metabolic enzyme that complements said mutations, wherein said Her-2/neu-expressing tumor growth or cancer is osteosarcoma, and wherein said recombinant *Listeria* lacks the actA virulence gene.

20. The method of claim 19, wherein said non-human animal is a dog.

21. The method of claim 19, wherein administering said fusion polypeptide to a subject having said osteosarcoma prevents escape mutations within said tumor or cancer.

22. The method of claim 19, wherein said Her-2/neu chimeric antigen comprises at least 5, 9, 13, 14, or 17 of the mapped human MHC-class I epitopes.

23. The method of claim 19, wherein said nucleic acid molecule is integrated into the *Listeria* genome.

24. The method of claim 19, wherein said nucleic acid molecule is in a plasmid in said recombinant *Listeria* strain.

25. The method of claim 24, wherein said plasmid is stably maintained in said recombinant *Listeria* strain in the absence of antibiotic selection.

26. The method of claim 24, wherein said plasmid does not confer antibiotic resistance upon said recombinant *Listeria*.

27. The method of claim 19, wherein said recombinant *Listeria* strain is attenuated.

28. The method of claim 19, wherein said additional polypeptide is selected from the group consisting of: a) non-hemolytic LLO protein or N-terminal fragment, b) a PEST sequence, or c) an ActA fragment.

29. The method of claim 19, wherein said metabolic enzyme encoded by said second open reading frame is an amino acid metabolism enzyme.

30. The method of claim 29, wherein said amino acid metabolism enzyme encoded by said second open reading frame is an alanine racemase enzyme or a D-amino acid transferase enzyme.

31. The method of claim 19, wherein said nucleic acid molecule further comprises a third open reading frame.

32. The method claim 31, wherein said third open reading frame encodes a metabolic enzyme, wherein said metabolic enzyme is a D-amino acid transferase enzyme or an alanine racemase enzyme.

33. The method of claim 19, wherein said recombinant *Listeria* strain has been passaged through an animal host.

34. The method of claim 19, further comprising an independent adjuvant.

35. The method of claim 34, wherein said adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

36. The method of claim 19, wherein said osteosarcoma cancer is a canine osteosarcoma.

37. A method of eliciting an enhanced immune response against a Her-2/neu-expressing tumor growth or cancer in a non-human animal, the method comprising the step of administering to said non-human animal a recombinant *Listeria* having mutations in the D-alanine racemase (Dal) gene and the D-amino acid transferase (Dat) gene, said recombinant *Listeria* comprising a nucleic acid encoding a first and a second open reading frame, wherein said first open reading frame encodes a recombinant polypeptide comprising SEQ ID NO: 2 fused to an additional polypeptide, and wherein said second open reading frame encodes a metabolic enzyme that complements said mutations, wherein said Her-2/neu-expressing tumor growth or cancer is osteosarcoma, and wherein said recombinant *Listeria* lacks the actA virulence gene.

38. The method of claim 37, wherein said non-human animal is a dog.

39. The method of claim 37, wherein administering said fusion polypeptide to a subject having said osteosarcoma prevents escape mutations within said tumor or cancer.

40. The method of claim 37, wherein said Her-2/neu chimeric antigen comprises at least 5, 9, 13, 14, or 17 of the mapped human MHC-class I epitopes.

41. The method of claim 37, wherein said nucleic acid molecule is integrated into the *Listeria* genome.

42. The method of claim 37, wherein said nucleic acid molecule is in a plasmid in said recombinant *Listeria* strain.

43. The method of claim 42, wherein said plasmid is stably maintained in said recombinant *Listeria* strain in the absence of antibiotic selection.

44. The method of claim 42, wherein said plasmid does not confer antibiotic resistance upon said recombinant *Listeria*.

45. The method of claim 37, wherein said recombinant *Listeria* strain is attenuated.

46. The method of claim 37, wherein said additional polypeptide is selected from the group consisting of: a) non-hemolytic LLO protein or N-terminal fragment, b) a PEST sequence, or c) an ActA fragment.

47. The method of claim 37, wherein said metabolic enzyme encoded by said second open reading frame is an amino acid metabolism enzyme.

48. The method of claim 47, wherein said amino acid metabolism enzyme encoded by said second open reading frame is an alanine racemase enzyme or a D-amino acid transferase enzyme.

49. The method of claim 37, wherein said nucleic acid molecule further comprises a third open reading frame.

50. The method of claim 49, wherein said third open reading frame encodes a metabolic enzyme, wherein said metabolic enzyme is a D-amino acid transferase enzyme or an alanine racemase enzyme.

51. The method of claim 37, wherein said recombinant *Listeria* strain has been passaged through an animal host.

52. The method of claim 37, further comprising an independent adjuvant.

53. The method of claim 52, wherein said adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

54. The method of claim 37, wherein said osteosarcoma cancer is a canine osteosarcoma.

55. The method of any one of claim 1, 19 or 37, wherein said immune response against said Her-2/neu-expressing tumor comprises an immune response to a subdominant epitope of said Her-2/neu protein.

56. The method of claim 1, wherein said mutations are deletions in the D-alanine racemase and D-amino acid transferase (dal/dat) genes.

57. The method of claim 19, wherein said mutations are deletions in the D-alanine racemase and D-amino acid transferase (dal/dat) genes.

58. The method of claim 37, wherein said mutations are deletions in the D-alanine racemase and D-amino acid transferase (dal/dat) genes.

59. The method of claim 1, wherein said *Listeria* expresses said recombinant polypeptide.

60. The method of claim 19, wherein said *Listeria* expresses said recombinant polypeptide.

61. The method of claim 37, wherein said *Listeria* expresses said recombinant polypeptide.

* * * * *